United States Patent
Salomon et al.

(10) Patent No.: US 12,146,123 B2
(45) Date of Patent: Nov. 19, 2024

(54) ENDONUCLEASE 1 RIBONUCLEASES FOR CLEANING

(71) Applicant: Novozymes A/S, Bagsvaerd (DK)

(72) Inventors: Jesper Salomon, Holte (DK); Dorotea Raventos Segura, Rungsted (DK); Dorota Nissen, Vedbaek (DK); Morten Gjermansen, Greve (DK); Fabian Barrientos, Birkerod (DK)

(73) Assignee: Novozymes A/S, Bagsvaerd (DK)

( * ) Notice: Subject to any disclaimer, the term of this patent is extended or adjusted under 35 U.S.C. 154(b) by 856 days.

(21) Appl. No.: 17/276,317

(22) PCT Filed: Sep. 27, 2019

(86) PCT No.: PCT/EP2019/076222
§ 371 (c)(1),
(2) Date: Mar. 15, 2021

(87) PCT Pub. No.: WO2020/070009
PCT Pub. Date: Apr. 9, 2020

(65) Prior Publication Data
US 2022/0073845 A1   Mar. 10, 2022

(30) Foreign Application Priority Data
Oct. 2, 2018 (EP) .................... 18198206

(51) Int. Cl.
| C11D 3/386 | (2006.01) |
| C12N 9/22 | (2006.01) |
| C12N 15/09 | (2006.01) |
| C12N 15/11 | (2006.01) |
| C12P 21/00 | (2006.01) |
| C12P 21/02 | (2006.01) |

(52) U.S. Cl.
CPC ............ *C11D 3/38636* (2013.01); *C12N 9/22* (2013.01); *C12N 15/09* (2013.01); *C12N 15/11* (2013.01); *C12P 21/00* (2013.01); *C12P 21/02* (2013.01)

(58) Field of Classification Search
CPC .. C11D 3/38636; C11D 3/38681; C12N 9/22; C12N 15/09; C12N 15/11; C12P 21/00; C12P 21/02; C12Y 301/00
See application file for complete search history.

(56) References Cited

U.S. PATENT DOCUMENTS 9,878,004 B2 * 1/2018 Williams ........... A61K 38/1767

FOREIGN PATENT DOCUMENTS

| EP | 3088506 A1 * | 11/2016 | ............... C11D 1/83 |
| WO | 2008/024457 A2 | 2/2008 | |
| WO | 2016/176240 A1 | 11/2016 | |
| WO | 2017/214236 A1 | 12/2017 | |
| WO | WO-2018134386 A1 * | 7/2018 | |

OTHER PUBLICATIONS

Jekel et al., 2013, NCBI Reference Sequence WP_010331769.1.
Nielsen et al., EBI Accession No. BFM66276 (2018).
Nielsen et al., EBI Accession No. BFM66277 (2018).

* cited by examiner

*Primary Examiner* — Nancy J Leith
*Assistant Examiner* — Kyle T Rega
(74) *Attorney, Agent, or Firm* — Elias Lambiris

(57) ABSTRACT

Disclosed are endonuclease 1 ribonuclease polypeptides and cleaning compositions containing the polypeptides. Also disclosed are methods for using the polypeptides and cleaning compositions. Also disclosed are polynucleotides encoding the polypeptides, and vectors and cells containing the polynucleotides.

13 Claims, 2 Drawing Sheets
Specification includes a Sequence Listing.

ENDONUCLEASE 1 RIBONUCLEASES FOR CLEANING

REFERENCE TO A SEQUENCE LISTING

This application contains a Sequence Listing in computer readable form, which is incorporated herein by reference.—The Sequence Listing was created on Sep. 27, 2019, and is named SQListing.txt and is 96,393 in size.

FIELD OF THE INVENTION

This application describes polypeptides with RNase activity, compositions containing the polypeptides, and polynucleotides encoding the polypeptides. Also disclosed are nucleic acid constructs and vectors encoding the polypeptides, and host cells expressing the constructs and vectors, for producing the polypeptides. Methods of using the polypeptides are disclosed.

BACKGROUND

Compositions for cleaning that contain enzymes are known in the art. Generally, the enzymes in the cleaning compositions may remove stains, improve whiteness, and eliminate malodor. The enzymes may degrade or remove molecules like proteins, polysaccharides or fats that may be present in soils and stains. In some instances, these molecules and others may be present in organic stains such as body oils, sweat, sebum, dead cells or biofilms, which are formations of microorganisms within a matrix, the matrix generally composed of an extracellular polymeric substance (EPS), that forms on surfaces. Biofilms are natural habitats for certain microorganisms and, as the microorganisms grow in the biofilms, they secrete molecules like polysaccharides, proteins, lipids, nucleic acids (e.g., DNA and RNA), etc.

New cleaning compositions, including those containing enzymes, and those capable of removing stains, improving whiteness and eliminating malodor continue to be developed.

SUMMARY

We have shown that compositions containing RNases, specifically endonuclease 1 ribonucleases, have cleaning activity on items, including fabrics. Although other enzymes have been shown to be efficacious in removing soils and stains, use of RNases has not been described.

In one aspect, the disclosed invention relates to isolated polypeptides with RNase activity, generally selected from amino acid sequences containing a Pfam PF04231 amino acid domain and having RNase activity. In some examples, the polypeptides have at least 60% sequence identity, or at least 60% sequence identity but less than 100% sequence identity, to one of SEQ ID NOs. 2 and/or 3, 5 and/or 6, 8 and/or 9, or 13 and/or 14. One embodiment relates to an isolated polypeptide with RNase activity, selected from the group consisting of:

an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to one of the groups of SEQ ID NOs. below, or an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99%, but less than 100% sequence identity to one of the groups of SEQ ID NOs. below:
(a) SEQ ID NO: 2 or SEQ ID NO: 3;
(b) SEQ ID NO: 5 or SEQ ID NO: 6;
(c) SEQ ID NO: 8 or SEQ ID NO: 9; and
(d) SEQ ID NO: 13 or SEQ ID NO: 14.

The inventive polypeptides are exclusive of a $Mg^{2+}$-activated ribonuclease from *Bacillus subtilis*, as described in Nakamura, A., et al., 1992. Gene cloning and characterization of a novel extracellular ribonuclease of *Bacillus subtilis*. European Journal of Biochemistry 209, 121-127.

In one aspect, the invention is related to the isolated polypeptides set forth above that are variants. The variants may have one or more amino acid substitutions, deletions, insertions, or combinations thereof. The variants may extensions of amino acids at the N-terminal, C-terminal, or both N- and C-terminal ends of the polypeptides. The extensions may be His- or HQ-tags. In some examples, the variants may have amino acid substitutions and/or deletions outside of PF04231 domains of the polypeptides. One aspect relates to an isolated polypeptide according to the invention, wherein the isolated polypeptide is a variant that has one or more amino acids deleted from the C-terminal end of the polypeptide, with the proviso that the PF04231 domain is intact. One aspect relates to the use of the isolated polypeptide described above and herein for cleaning an item.

In one aspect, the invention is related to compositions that contain any of the polypeptides described above and herein. One aspect relates to a composition, comprising the isolated polypeptides described above and herein, and at least one cleaning composition component and/or detergent adjunct ingredient. The compositions may contain other enzymes, in addition to the polypeptides having RNase activity, including DNases, proteases, amylases, lipases, cutinases, cellulases, endoglucanases, xyloglucanases, pectinases, pectin lyases, xanthanases, peroxidases, haloperoxygenases, catalases and/or mannanases. In some cases, one or more of those additional enzymes may be specifically excluded from the compositions. In some embodiments, one or more of the above-listed enzymes may be specifically excluded from the compositions disclosed herein. One aspect relates to a detergent composition, comprising a polypeptide described above and herein and a detergent adjunct ingredient.

In one aspect, the invention is related to methods of using the polypeptides or compositions described above and herein. The item may be a textile. The methods are generally methods for cleaning the item by exposing the item to the polypeptides or compositions.

One aspect relates to a method for cleaning an item, comprising contacting the item with the composition described above and herein. One aspect relates to a method for laundering an item, comprising:
(a) exposing the item to the composition described above and herein;
(b) completing at least one wash cycle; and
(c) optionally, rinsing the textile.

One aspect relates to the use of the polypeptides or the composition described above and herein for cleaning an item.

In other aspects, the invention is related to polynucleotides encoding the polypeptides described above and herein, nucleic acid constructs or expression vectors comprising the polynucleotides, and recombinant host cells comprising the nucleic acid constructs or expression vectors.

OVERVIEW OF SEQUENCES

Figure 1:
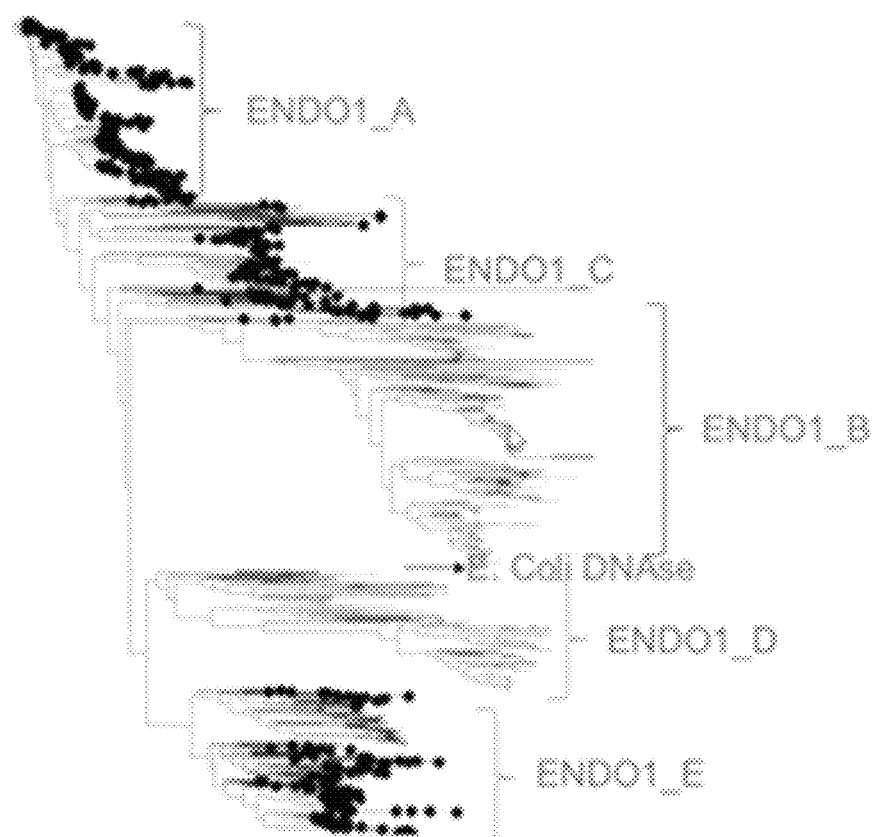
FIG. 1 illustrates the phylogenetic tree that is described in Example 1.

SEQ ID NO: 1 is a DNA sequence from *Bacillus mojavensis* that encodes a full-length polypeptide.

SEQ ID NO: 2 is a full-length polypeptide encoded by SEQ ID NO: 1.

SEQ ID NO: 3 is a mature polypeptide derived from SEQ ID NO: 2.

SEQ ID NO: 4 is a DNA sequence from *Bacillus subtilis* that encodes a full-length polypeptide.

SEQ ID NO: 5 is a full-length polypeptide encoded by SEQ ID NO: 4.

SEQ ID NO: 6 is a mature polypeptide derived from SEQ ID NO: 5.

SEQ ID NO: 7 is a DNA sequence from *Bacillus pumilus* that encodes a full-length polypeptide.

SEQ ID NO: 8 is a full-length polypeptide encoded by SEQ ID NO: 7.

SEQ ID NO: 9 is a mature polypeptide derived from SEQ ID NO: 8.

SEQ ID NO: 10 is a codon-optimized DNA sequence derived from SEQ ID. NO: 7 that encodes a full-length polypeptide.

SEQ ID NO: 11 is a is a full-length polypeptide encoded by SEQ ID NO: 10. This is the same protein as shown in SEQ ID NO: 8.

SEQ ID NO: 12 is a DNA sequence from *Bacillus subtilis* subsp. *spizizenii* that encodes a full-length polypeptide.

SEQ ID NO: 13 is a full-length polypeptide encoded by SEQ ID NO: 12.

SEQ ID NO: 14 is a mature polypeptide derived from SEQ ID NO: 13.

SEQ ID NO: 15 is a codon-optimized DNA sequence derived from SEQ ID. NO: 12 that encodes a full-length polypeptide.

SEQ ID NO: 16 is a full-length polypeptide encoded by SEQ ID NO: 15. This is the same protein as shown in SEQ ID NO: 13.

SEQ ID NO: 17 is a DNA sequence from *Saccharopolyspora hirsuta* that encodes a full-length polypeptide.

SEQ ID NO: 18 is a full-length polypeptide encoded by SEQ ID NO: 17.

SEQ ID NO: 19 is a mature polypeptide derived from SEQ ID NO: 18.

SEQ ID NO: 20 is a DNA sequence from *Bacillus licheniformis* that encodes a full-length polypeptide.

SEQ ID NO: 21 is a full-length polypeptide encoded by SEQ ID NO: 20.

SEQ ID NO: 22 is a mature polypeptide derived from SEQ ID NO: 21.

SEQ ID NO: 23 is a DNA sequence from *Streptomyces thermocarboxydus* that encodes a full-length polypeptide.

SEQ ID NO: 24 is a full-length polypeptide encoded by SEQ ID NO: 23.

SEQ ID NO: 25 is a mature polypeptide derived from SEQ ID NO: 24.

SEQ ID NO: 26 is a DNA sequence from *Bacillus licheniformis* that encodes a full-length polypeptide.

SEQ ID NO: 27 is a full-length polypeptide encoded by SEQ ID NO: 26.

SEQ ID NO: 28 is a mature polypeptide derived from SEQ ID NO: 27.

SEQ ID NO: 29 is a DNA sequence from *Saccharopolyspora gregorii* that encodes a full-length polypeptide.

SEQ ID NO: 30 is a full-length polypeptide encoded by SEQ ID NO: 29.

SEQ ID NO: 31 is a mature polypeptide derived from SEQ ID NO: 30.

SEQ ID NO: 32 is an amino acid motif found in some endonuclease 1 ribonuclease polypeptides.

SEQ ID NO: 33 is an amino acid motif found in some endonuclease 1 ribonuclease polypeptides.

SEQ ID NO: 34 is an amino acid motif found in some endonuclease 1 ribonuclease polypeptides.

SEQ ID NO: 35 is an amino acid motif found in some endonuclease 1 ribonuclease polypeptides.

SEQ ID NO: 36 is secretion signal amino acid sequence from *Bacillus clausii*.

Definitions

The term "allelic variant" means any of two or more alternative forms of a gene occupying the same chromosomal locus. Allelic variation may arise naturally through mutation and may result in polymorphism within populations. These genetic changes, if within a polypeptide-coding sequence, may be silent (no change in the encoded polypeptide) or may encode polypeptides having altered amino acid sequences. An allelic variant of a polypeptide is a polypeptide encoded by an allelic variant of a gene.

The term "biofilm" means a film produced by any group of microorganisms in which cells stick to each other or stick to a surface, such as a textile, dishware, hard surface or another kind of surface. These adherent cells are frequently embedded within a self-produced matrix of extracellular polymeric substance (EPS). Biofilm EPS is a polymeric conglomeration, generally composed of extracellular macromolecules, for example, DNA, proteins, and polysaccharides. Biofilms may form on living or non-living surfaces. The microbial cells growing in a biofilm may be physiologically distinct from planktonic cells of the same organism, which, by contrast, are single-cells that may float or swim in a liquid medium. Bacteria living in a biofilm may have different properties from planktonic bacteria of the same species, as the dense and protected environment of the film allows them to cooperate and interact in various ways. One benefit of this environment for the microorganisms is increased resistance to detergents and antibiotics, as the dense extracellular matrix and the outer layer of cells protect the interior of the community.

The term "cDNA" means a DNA molecule that can be prepared by reverse transcription from a mature, spliced mRNA molecule obtained from a eukaryotic or prokaryotic cell. cDNA lacks intron sequences that may be present in the corresponding genomic DNA. The initial, primary RNA transcript is a precursor to mRNA that is processed through a series of steps, including splicing, before appearing as mature spliced mRNA.

The term "coding sequence" means a polynucleotide which directly specifies the amino acid sequence of a polypeptide. The boundaries of the coding sequence are generally determined by an open reading frame, which begins with a start codon such as ATG, GTG, or TTG and ends with a stop codon such as TAA, TAG, or TGA. The coding sequence may be a genomic DNA, cDNA, synthetic DNA, or a combination thereof.

The term "control sequences" means nucleic acid sequences necessary for expression of a polynucleotide encoding a mature polypeptide of the present invention. Each control sequence may be native (i.e., from the same gene) or foreign (i.e., from a different gene) to the polynucleotide encoding the polypeptide or native or foreign to each other. Such control sequences include, but are not limited to, a leader, polyadenylation sequence, propeptide sequence, promoter, signal peptide sequence, and transcription terminator. At a minimum, the control sequences include a promoter, and transcriptional and translational stop signals. The control sequences may be provided with linkers for the purpose of introducing specific restriction sites facilitating ligation of the control sequences with the coding region of the polynucleotide encoding a polypeptide.

The term "deep cleaning" means, in this context disruption, reduction or removal of organic components such as polysaccharides, proteins, RNA, DNA, soil or other components present in organic matter such as biofilm. In some examples, reducing or removing biofilms from textiles/fabrics is deep cleaning.

The term "detergent adjunct ingredient" refers to ingredients different from the RNases of this invention. The precise nature of these additional adjunct components, and levels of incorporation thereof, will depend on the physical form of the composition and the nature of the operation for which it is to be used. Suitable adjunct materials include, but are not limited to the components described below such as surfactants, builders, flocculating aids, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric huing agents, anti-foaming agents, dispersants, processing aids, and/or pigments.

The term "cleaning component" includes any component (which is not water) useful in laundry and dish wash, including hand dish wash compositions and includes but are not limited to surfactants, builders, flocculating aids, chelating agents, dye transfer inhibitors, enzymes, enzyme stabilizers, enzyme inhibitors, catalytic materials, bleach activators, hydrogen peroxide, sources of hydrogen peroxide, preformed peracids, polymeric agents, clay soil removal/anti-redeposition agents, brighteners, suds suppressors, dyes, perfumes, structure elasticizing agents, fabric softeners, carriers, hydrotropes, builders and co-builders, fabric hueing agents, anti-foaming agents, dispersants, processing aids, and/or pigments. The choice of cleaning components may include, for textile care, the consideration of the type of textile to be cleaned, the type and/or degree of soiling, the temperature at which cleaning is to take place. The term "detergent composition" or "cleaning composition" refers to compositions that find use in the removal of undesired compounds from items to be cleaned, such as textiles. The terms "detergent compositions" and "cleaning compositions" are used interchangeably in the present application. The cleaning e.g. detergent composition may be used to, e.g., clean textiles for both household cleaning and industrial cleaning. The terms encompass any materials/compounds selected for the particular type of cleaning composition desired and the form of the product (e.g., liquid, gel, powder, granulate, paste, or spray compositions) and include, but are not limited to, cleaning e.g. detergent compositions such as liquid and/or solid laundry detergents and fine fabric detergents; fabric fresheners; fabric softeners; and textile and laundry pre-spotters/pretreatment. In addition to containing the enzyme of the invention, the cleaning e.g. detergent formulation may contain one or more additional enzymes (such as proteases, amylases, lipases, cutinases, cellulases, endoglucanases, xyloglucanases, pectinases, pectin lyases, xanthanases, peroxidases, haloperoxygenases, catalases and mannanases, or any mixture thereof), and/or detergent adjunct ingredients such as surfactants, builders, chelators or chelating agents, bleach systems or bleach components, polymers, fabric conditioners, foam boosters, suds suppressors, dyes, perfume, tannish inhibitors, optical brighteners, bactericides, fungicides, soil suspending agents, anti-corrosion agents, enzyme inhibitors or stabilizers, enzyme activators, transferase(s), hydrolytic enzymes, oxido reductases, bluing agents and fluorescent dyes, antioxidants, and solubilizers.

The term "endonuclease 1 ribonuclease" refers to polypeptides that contain a Pfam PF04231 domain and have RNase activity. Information related to the amino acid domain referred to as Pfam PF04231 is found elsewhere in this disclosure and here: pfam.xfam.org/family/PF04231. Other domains may additionally be present in the endonuclease 1 ribonucleases.

The term "expression" includes any step involved in the production of a polypeptide including, but not limited to, transcription, post-transcriptional modification, translation, post-translational modification, and secretion.

The term "expression vector" means a linear or circular DNA molecule that comprises a polynucleotide encoding a polypeptide and is operably linked to control sequences that provide for its expression.

A "His-tag" refers to a polyhistidine tag typically comprising at least 6 histidine residues, that may be added to the N- or C-terminal. His-tags are known in the art for use in e.g. protein purification but may also be used for improving solubility at low pH values. Similarly, an "HQ-tag", i.e. a histidine-glutamine tag, may also be used for purification as is known in the art.

The term "host cell" means any cell type that is susceptible to transformation, transfection, transduction, or the like with a nucleic acid construct or expression vector comprising a polynucleotide of the present invention. The term "host cell" encompasses any progeny of a parent cell that is not identical to the parent cell due to mutations that occur during replication.

The term "immature polypeptide" means a polypeptide that is not in its final form following translation. For example, an immature polypeptide may undergo post-translation modifications, such as N-terminal processing, C-terminal truncation, glycosylation, phosphorylation, etc., before it is considered a mature polypeptide. Herein, an immature polypeptide may be referred to as a full-length polypeptide.

The term "isolated" means a substance in a form or environment that does not occur in nature. Non-limiting examples of isolated substances include (1) any non-naturally occurring substance, (2) any substance including, but not limited to, any enzyme, variant, nucleic acid, protein, peptide or cofactor, that is at least partially removed from one or more or all of the naturally occurring constituents with which it is associated in nature; (3) any substance modified by the hand of man relative to that substance found in nature; or (4) any substance modified by increasing the amount of the substance relative to other components with which it is naturally associated (e.g., recombinant production in a host cell; multiple copies of a gene encoding the substance; and use of a stronger promoter than the promoter naturally associated with the gene encoding the substance). An isolated substance may be present in a fermentation broth sample; e.g. a host cell may be genetically modified to express the polypeptide of the invention. The fermentation broth from that host cell will comprise the isolated polypeptide.

The term "laundering" relates to both household laundering and industrial laundering and means the process of treating textiles with a solution containing a cleaning or detergent composition of the present invention. The laundering process can for example be carried out using e.g. a household or an industrial washing machine or can be carried out by hand (i.e., manually).

The term "laundry" generally refers to household (e.g., clothes, towels, sheets, and the like) or industrial fabric items that are soiled (e.g., have less than optimal whiteness; produce a malodor).

By the term "malodor" is meant an odor which is not desired on clean items. The cleaned item should smell fresh and clean, without malodors adhered to the item. One example of malodor is compounds with an unpleasant smell which may be produced by microorganisms and trapped within a biofilm or stick to the "glue" of a biofilm. Other examples of unpleasant smells are sweat or body odor adhered to an item which has been in contact with a human or animal. Other examples of malodor are odors from spices which stick to items, for example curry or other exotic spices with a strong smell.

The term "mature polypeptide" means a polypeptide in its final form following translation and any post-translational modifications, such as N-terminal processing, C-terminal truncation, glycosylation, phosphorylation, etc.

It is known in the art that a host cell may produce a mixture of two of more different mature polypeptides (i.e., with a different C-terminal and/or N-terminal amino acid) expressed by the same polynucleotide. It is also known in the art that different host cells process polypeptides differently, and thus, one host cell expressing a polynucleotide may produce a different mature polypeptide (e.g., having a different C-terminal and/or N-terminal amino acid) as compared to another host cell expressing the same polynucleotide.

The term "mature polypeptide coding sequence" means a polynucleotide that encodes a mature polypeptide having RNase activity.

The term "microorganism" generally means small organisms that are visible through a microscope. Microorganisms often exist as single cells or as colonies of cells. Some microorganisms may be multicellular. Microorganisms include prokaryotic (e.g., bacteria and archaea) and eurkaryotic (e.g., some fungi, algae, protozoa) organisms. Herein, viruses may be considered microorganisms.

The term "naturally occurring" generally means existing in nature, without human intervention. More specifically, "naturally occurring" encompasses things that are not patentable in the United States under Section 101 of Title 35 of the United States Code. In some examples, the polypeptides disclosed herein may be naturally occurring. In some examples, the polypeptides disclosed herein may not be naturally occurring.

The term "nucleic acid construct" means a nucleic acid molecule, either single- or double-stranded, which is isolated from a naturally occurring gene or is modified to contain segments of nucleic acids in a manner that would not otherwise exist in nature or which is synthetic, which comprises one or more control sequences.

The term "operably linked" means a configuration in which a control sequence is placed at an appropriate position relative to the coding sequence of a polynucleotide such that the control sequence directs expression of the coding sequence.

The relatedness between two amino acid sequences or between two nucleotide sequences is described by the parameter "sequence identity".

For purposes of the present invention, the sequence identity between two amino acid sequences is determined using the Needleman-Wunsch algorithm (Needleman and Wunsch, 1970, J. Mol. Biol. 48: 443-453) as implemented in the Needle program of the EMBOSS package (EMBOSS: The European Molecular Biology Open Software Suite, Rice et al., 2000, Trends Genet. 16: 276-277), preferably version 5.0.0 or later. The parameters used are gap open penalty of 10, gap extension penalty of 0.5, and the EBLOSUM62 (EMBOSS version of BLOSUM62) substitution matrix. The output of Needle labeled "longest identity" (obtained using the –nobrief option) is used as the percent identity and is calculated as follows:

$$(\text{Identical Residues} \times 100)/(\text{Length of Alignment} - \text{Total Number of Gaps in Alignment}).$$

The term "RNase" is an abbreviation of the term ribonuclease, which means a nuclease having RNase activity that catalyzes degradation of RNA into smaller components. Ribonucleases can be divided into endoribonucleases and exoribonucleases. In some embodiments of the present invention the ribonucleases may have endoribonuclease activity, exoribonuclease activity, or endoribonuclease and exoribonuclease activity. For purposes of the present invention, RNase activity is determined according to procedures described in the Examples. Generally, the RNases disclosed herein are polypeptides and are enzymes. In one aspect, the polypeptides of the present invention have at least 20%, e.g., at least 40%, at least 50%, at least 60%, at least 70%, at least 80%, at least 90%, at least 95%, or at least 100% of the RNase activity of any of the mature polypeptides shown in SEQ ID NOs: 3, 6, 9, or 14. Assays that measure RNase activity generally measure degradation of RNA into smaller components.

Generally, the RNases that are the subject of this application are endonuclease 1 ribonucleases. Endonuclease 1 ribonucleases are generally defined by the presence of an amino acid domain described as Pfam PF04231. In addition, other domains may be present in the endonuclease 1 ribonucleases.

The term "textile" means cloth or fabric.

The term "variant" means a polypeptide having RNase activity comprising an alteration, i.e., a substitution, insertion, and/or deletion, at one or more (e.g., several) positions. A substitution means replacement of the amino acid occupying a position with a different amino acid; a deletion means removal of the amino acid occupying a position; and an insertion means adding an amino acid adjacent to and immediately following the amino acid occupying a position.

The term "whiteness" refers to the property or quality of being white. Generally, whiteness of a textile may correlate with its cleanliness. Deep cleaning of a soiled item may increase the whiteness of the item.

Nomenclature

For purposes of this disclosure, the nomenclature [E/Q] or simply [EQ] means that the amino acid at this position may be a glutamic acid (Glu, E) or a glutamine (Gln, Q). Likewise, the nomenclature [V/G/A/I] or [VGAI] means that the amino acid at this position may be a valine (Val, V), glycine (Gly, G), alanine (Ala, A) or isoleucine (Ile, 1), and so forth for other combinations as described herein. Unless otherwise limited further, the amino acid X is defined such that it may be any of the 20 natural amino acids.

RNases

The RNases disclosed herein are endonuclease 1 ribonucleases. Generally, in this disclosure, endonuclease 1 ribonucleases contain a PFAM PF04231 amino acid domain and have RNase activity. In some examples, the endonuclease 1 ribonucleases contain one or more of the amino acid motifs that are described in Example 3 herein.

The PFAM protein family database is a resource of the European Bioinformatics Institute (EMBL-EBI) (pfam.xfam.org/). The PFAM PF04231 domain is an amino acid domain. For PFAM domains/families, including PF04231, a group of protein sequences called seeds were chosen to define the family. For PF04231, the seeds used to define the family and create a seed alignment are shown here: pfam.xfam.org/family/PF04231/alignment/seed/html. The seed alignment was used to construct a profile hidden Markov model (HMM) using HMMER3 software (hmmer.org/) (Accelerated profile HMM searches. S. R. Eddy. PLOS Comp. Biol., 7:e1002195, 2011). An HMM profile for PF04231 is here: pfam.xfam.org/family/PF04231/hmm. The HMM file can be opened using HMMER3. This HMM profile was used to search other protein sequences, with all matches scoring greater than or equal to a curated threshold (called the gathering threshold) considered as members of the PF04231 family (pfam.xfam.org/family/PF04231#tabview=tab6). These members were subsequently aligned to the profile HMM to generate a full alignment.

The molecules disclosed herein have RNase activity. RNase activity is generally determined using assays that measure degradation of RNA into smaller components. Example assays are known in the art. Some example assays are described in the Examples of this disclosure.

Endonuclease 1 ribonucleases may come from many different organisms. Endonuclease 1 ribonucleases may come from prokaryotes, archaea or eukaryotes. In some examples, endonuclease 1 ribonucleases originate from microbes. In some examples, endonuclease 1 ribonucleases may come from fungi. In some examples, endonuclease 1 ribonucleases may come from bacteria. The origins of many known polypeptides that contain PF04231 domains can be found at: pfam.xfam.org/family/PF04231 #tabview=tab7.

One example of a polypeptide containing the PFAM PF04231 domain and having RNase activity is the $Mg^{2+}$-activated ribonuclease from *Bacillus subtilis* that has been described (Nakamura, A., et al., 1992. Gene cloning and characterization of a novel extracellular ribonuclease of *Bacillus subtilis*. European Journal of Biochemistry 209, 121-127).

The group of polypeptides according to the invention containing Pfam PF04231 domain also comprise the amino acid sequence NREH (SEQ ID NO: 32). This conservative domain is characteristic for the RNases e.g. endonuclease 1 ribonucleases and allow for grouping of RNases having same structural and functional characteristics, such as wash performance, biofilm reduction capabilities, deep cleaning effects etc. The polypeptides comprising the NREH (SEQ ID NO: 32) sequence could be separated into further sub-clusters. One sub-cluster comprise the amino acid sequence D[AEQ]DP (SEQ ID NO: 33). These polypeptides are here defined as being members of the DADP clade (D[AEQ]DP; SEQ ID NO: 33). This clade encompasses polypeptides present in the ENDO1 A and ENDO1 C branches of the phylogenetic tree. Such RNase polypeptides sharing the same conservative sequence also share some functional features and in general the more motives and the further branched in the phylogenetic tree the more functional relationship the polypeptides e.g. RNases share. The RNase polypeptides that are members of the DADP clade (D[AEQ]DP; SEQ ID NO: 33) maybe be separated into further sub-clusters. One sub-cluster comprise the amino acid sequence TDEDP (SEQ ID NO: 34). These polypeptides are here defined as being members of the TDED clade (TDEDP; SEQ ID NO: 34). This clade encompasses polypeptides present in the ENDO1 A branch of the phylogenetic tree. RNase polypeptides that were members of the TDED clade (TDEDP; SEQ ID NO: 34) could be further separated into sub-clusters. Some of these RNase polypeptides contained the amino acid sequence SHG. Some polypeptides in the TDED clade (TDEDP; SEQ ID NO: 34) comprised the amino acid sequence NREHVWA (SEQ ID NO: 35).

One embodiment of the invention relates to a RNase, preferably an endonuclease 1 ribonucleases, comprising the amino acid sequence NREH (SEQ ID NO: 32).

One embodiment of the invention relates to a RNase, preferably an endonuclease 1 ribonucleases, comprising the amino acid sequence D[AEQ]DP (SEQ ID NO: 33).

One embodiment of the invention relates to a RNase, preferably an endonuclease 1 ribonucleases, comprising the amino acid sequence TDEDP (SEQ ID NO: 34).

One embodiment of the invention relates to a RNase, preferably an endonuclease 1 ribonucleases, comprising the amino acid sequence SHG.

One embodiment of the invention relates to a RNase, preferably an endonuclease 1 ribonucleases, comprising the amino acid sequence NREHVWA (SEQ ID NO: 35).

One embodiment of the invention relates to an isolated polypeptide having RNase activity and additionally comprises at least one of the amino acid sequences NREH (SEQ ID NO: 32), D[AEQ]DP (SEQ ID NO: 33), TDEDP (SEQ ID NO: 34), SHG and/or NREHVWA (SEQ ID NO: 35).

One embodiment of the invention relates to a RNase, preferably an endonuclease 1 ribonucleases, comprising the amino acid sequence(s) NREH (SEQ ID NO: 32) and/or the amino acid sequence D[AEQ]DP (SEQ ID NO: 33).

One embodiment of the invention relates to a RNase, preferably an endonuclease 1 ribonucleases, comprising the amino acid sequence(s) NREH (SEQ ID NO: 32), D[AEQ]DP (SEQ ID NO: 33) and/or the amino acid sequence TDEDP (SEQ ID NO: 34).

One embodiment of the invention relates to a RNase, preferably an endonuclease 1 ribonucleases, comprising the amino acid sequence(s) NREH (SEQ ID NO: 32), D[AEQ]DP (SEQ ID NO: 33), TDEDP (SEQ ID NO: 34) and/or the amino acid sequence SHG.

One embodiment of the invention relates to a RNase, preferably an endonuclease 1 ribonucleases, comprising the amino acid sequence(s) NREH (SEQ ID NO: 32), D[AEQ]DP (SEQ ID NO: 33), TDEDP (SEQ ID NO: 34), SHG and/or the amino acid sequence NREHVWA (SEQ ID NO: 35).

In one aspect, the polypeptides disclosed herein are immature endonuclease 1 ribonucleases. Specifically, disclosed herein are:

SEQ ID NO: 2 is a full-length endonuclease 1 ribonuclease from *Bacillus mojavensis*. The region of this polypeptide which contains the domain identifying the polypeptide as an endonuclease 1 ribonuclease includes approximate amino acids 47-255 of SEQ ID NO: 2. SEQ ID NO: 3 is amino acids 1-262 of SEQ ID NO: 2.

SEQ ID NO: 5 is a full-length endonuclease 1 ribonuclease from *Bacillus subtilis*. The region of this polypeptide which contains the domain identifying the polypeptide as an endonuclease 1 ribonuclease includes approximate amino acids 44-253 of SEQ ID NO: 5. SEQ ID NO: 6 is amino acids 1-260 of SEQ ID NO: 5.

SEQ ID NO: 8 is a full-length endonuclease 1 ribonuclease from *Bacillus pumilus*. The region of this polypeptide which contains the domain identifying the polypeptide as an endonuclease 1 ribonuclease includes approximate amino acids 47-255 of SEQ ID NO: 8. SEQ ID NO: 9 is amino acids 1-262 of SEQ ID NO: 8.

SEQ ID NO: 11 is the same as SEQ ID NO: 8.

SEQ ID NO: 13 is a full-length endonuclease 1 ribonuclease from *Bacillus subtilis* subsp. *spizizenii*. The region of this polypeptide which contains the domain identifying the polypeptide as an endonuclease 1 ribonuclease includes approximate amino acids 46-255 of SEQ ID NO: 13. SEQ ID NO: 14 is amino acids 1-262 of SEQ ID NO: 13.

SEQ ID NO: 16 is the same as SEQ ID NO: 13.

SEQ ID NO: 18 is a full-length endonuclease 1 ribonuclease from *Saccharopolyspora hirsuta*. The region of this polypeptide which contains the domain identifying the polypeptide as an endonuclease 1 ribonuclease includes approximate amino acids 14-224 of SEQ ID NO: 18. SEQ ID NO: 19 is amino acids 1-230 of SEQ ID NO: 18.

SEQ ID NO: 21 is a full-length endonuclease 1 ribonuclease from *Bacillus licheniformis*. The region of this polypeptide which contains the domain identifying the polypeptide as an endonuclease 1 ribonuclease includes approximate amino acids 27-236 of SEQ ID NO: 21. SEQ ID NO: 22 is amino acids 1-248 of SEQ ID NO: 21.

SEQ ID NO: 24 is a full-length endonuclease 1 ribonuclease from *Streptomyces thermocarboxydus*. The region of this polypeptide which contains the domain identifying the polypeptide as an endonuclease 1 ribonuclease includes approximate amino acids 23-232 of SEQ ID NO: 24. SEQ ID NO: 25 is amino acids 1-238 of SEQ ID NO: 24.

SEQ ID NO: 27 is a full-length endonuclease 1 ribonuclease from *Bacillus licheniformis*. The region of this polypeptide which contains the domain identifying the polypeptide as an endonuclease 1 ribonuclease includes approximate amino acids 27-236 of SEQ ID NO: 27. SEQ ID NO: 28 is amino acids 1-248 of SEQ ID NO: 27.

SEQ ID NO: 30 is a full-length endonuclease 1 ribonuclease from *Saccharopolyspora gregorii*. The region of this polypeptide which contains the domain identifying the polypeptide as an endonuclease 1 ribonuclease includes approximate amino acids 26-235 of SEQ ID NO: 30. SEQ ID NO: 31 is amino acids 1-242 of SEQ ID NO: 30.

In one aspect, the polypeptides disclosed herein are mature endonuclease 1 ribonucleases polypeptides. Specifically disclosed herein are:

In one aspect, the mature polypeptide is amino acids 1 to 262 of SEQ ID NO: 3. Amino acids −26 to −1 of SEQ ID NO: 2 is the signal peptide. The mature polypeptide is also shown in SEQ ID NO: 3.

In one aspect, the mature polypeptide is amino acids 1 to 260 of SEQ ID NO: 6. Amino acids −28 to −1 of SEQ ID NO: 5 is the signal peptide. The mature polypeptide is also shown in SEQ ID NO: 6.

In one aspect, the mature polypeptide is amino acids 1 to 262 of SEQ ID NO: 9. Amino acids −26 to −1 of SEQ ID NO: 8 is the signal peptide. The mature polypeptide is also shown in SEQ ID NO: 9.

In one aspect, the mature polypeptide is amino acids 1 to 262 of SEQ ID NO: 14. Amino acids −26 to −1 of SEQ ID NO: 13 is the signal peptide. The mature polypeptide is also shown in SEQ ID NO: 14.

In one aspect, the mature polypeptide is amino acids 1 to 230 of SEQ ID NO: 19. Amino acids −27 to −1 of SEQ ID NO: 18 is the signal peptide. The mature polypeptide is also shown in SEQ ID NO: 19.

In one aspect, the mature polypeptide is amino acids 1 to 248 of SEQ ID NO: 22. Amino acids −25 to −1 of SEQ ID NO: 21 is the signal peptide. The mature polypeptide is also shown in SEQ ID NO: 22.

In one aspect, the mature polypeptide is amino acids 1 to 238 of SEQ ID NO: 25. Amino acids −35 to −1 of SEQ ID NO: 24 is the signal peptide. The mature polypeptide is also shown in SEQ ID NO: 25.

In one aspect, the mature polypeptide is amino acids 1 to 248 of SEQ ID NO: 28. Amino acids −25 to −1 of SEQ ID NO: 27 is the signal peptide. The mature polypeptide is also shown in SEQ ID NO: 28.

In one aspect, the mature polypeptide is amino acids 1 to 242 of SEQ ID NO: 31. Amino acids −27 to −1 of SEQ ID NO: 30 is the signal peptide. The mature polypeptide is also shown in SEQ ID NO: 31.

In one aspect, the mature polypeptide is amino acids 1 to 262 of SEQ ID NO: 3.

In one aspect, the mature polypeptide is amino acids 1 to 260 of SEQ ID NO: 6.

In one aspect, the mature polypeptide is amino acids 1 to 262 of SEQ ID NO: 9.

In one aspect, the mature polypeptide is amino acids 1 to 262 of SEQ ID NO: 14.

In one aspect, the mature polypeptide is amino acids 1 to 230 of SEQ ID NO: 19.

In one aspect, the mature polypeptide is amino acids 1 to 248 of SEQ ID NO: 22.

In one aspect, the mature polypeptide is amino acids 1 to 238 of SEQ ID NO: 25.

In one aspect, the mature polypeptide is amino acids 1 to 248 of SEQ ID NO: 28.

In one aspect, the mature polypeptide is amino acids 1 to 242 of SEQ ID NO: 31.

In some embodiments, the invention may be peptides comprising or consisting of an amino acid sequence having sequence identity to any of the above mature polypeptides of at least 60%, at least 61%, at least 62%, at least 63%, at least 64%, at least 65%, at least 66%, at least 67%, at least 68%, at least 69%, at least 70%, at least 71%, at least 72%, at least 73%, at least 74%, at least 75%, at least 76%, at least 77%, at least 78%, at least 79%, at least 80%, at least 81%, at least 82%, at least 83%, at least 84%, at least 85%, at least 86%, at least 87%, at least 88%, at least 89%, at least 90%, at least 91%, at least 92%, at least 93%, at least 94%, at least 95%, at least 96%, at least 97%, at least 98%, at least 99%, or 100%.

In some embodiments, the invention may be polypeptides comprising or consisting of an amino acid sequence with identity to any of the above mature polypeptides of less than 100%, but at least as much sequence identity as set forth in one of the instances above (i.e., 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98% or 99%).

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 3.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 6.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 9.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 14.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 19.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 22.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 25.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 28.

In some embodiments, the invention relates to a polypeptide comprising an amino acid sequence having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity to SEQ ID NO: 31. In some embodiments, the invention may be polypeptides that comprise or consist of allelic variants of any of the mature amino acid sequences set forth above, or fragments thereof that have RNase activity.

In some embodiments, the polypeptide may comprise or consist of any of the mature amino acid sequences set forth above; comprise or consist of one of those amino acid sequences and an N-terminal and/or C-terminal His-tag and/or HQ-tag; comprise or consist of one of those amino acid sequences and an N-terminal and/or C-terminal extension of between 1 and 10 amino acids; or a fragment thereof having RNase activity, and having at least 50%, at least 60%, at least 70%, at least 75%, at least 80%, at least 85%, at least 90%, at least 95%, at least 96%, at least 97%, at least 98% or at least 99% of the length of one of those amino acid sequences.

In some embodiments, the invention may relate to variants of any of the mature polypeptides set forth above, comprising a substitution, deletion, and/or insertion at one or more (e.g., several) positions. In some embodiments, the number of amino acid substitutions, deletions and/or insertions is up to 10, e.g., 1, 2, 3, 4, 5, 6, 7, 8, 9, or 10.

Some of the changes in amino acid sequences of the inventive endonuclease 1 ribonucleases, as compared to the amino acid sequences set forth in the Sequence Listing that is a part of this patent application (e.g., when the inventive polypeptide is not 100% identical to one of amino acid sequences set forth in the Sequence Listing), may be described as set forth below.

The amino acid changes may be of a minor nature, like conservative amino acid substitutions or insertions that do not significantly affect the folding and/or activity of the protein; small deletions, typically of 1-30 amino acids; small amino- or carboxyl-terminal extensions, like an amino-terminal methionine residue; a small linker peptide of up to 20-25 residues; or a small extension that facilitates purification by changing net charge or another function, such as a poly-histidine tract, an antigenic epitope or a binding domain.

Examples of conservative substitutions are within the groups of basic amino acids (arginine, lysine and histidine), acidic amino acids (glutamic acid and aspartic acid), polar amino acids (glutamine and asparagine), hydrophobic amino acids (leucine, isoleucine and valine), aromatic amino acids (phenylalanine, tryptophan and tyrosine), and small amino acids (glycine, alanine, serine, threonine and methionine).

Essential amino acids in a polypeptide may be defined as amino acids that cannot be substituted or deleted without loss of RNase activity. These amino acids can be identified according to procedures known in the art, such as site-directed mutagenesis or alanine-scanning mutagenesis. In the latter technique, single alanine mutations are introduced at every residue in the molecule, and the resultant molecules are tested for RNase activity to identify amino acid residues that are critical to the activity of the molecule. Generally, these amino acids can be identified by substituting or deleting them, and then testing the substituted/deletion molecule for RNase activity. These methods are well known in the art. Amino acids that, when deleted or substituted, result in loss of some, but not all RNase activity may exist in the polypeptides.

The active site of the enzyme or other biological interaction can be determined by physical analysis of structure, as determined by such techniques as nuclear magnetic resonance, crystallography, electron diffraction, or photoaffinity labeling, in conjunction with mutation of putative contact site amino acids. The identity of essential amino acids can also be inferred from an alignment with a related polypeptide.

Single or multiple amino acid substitutions, deletions, and/or insertions can be made and tested using known methods of mutagenesis, recombination, and/or shuffling, followed by a relevant screening procedure. Other methods that can be used include error-prone PCR, phage display, and region-directed mutagenesis.

Mutagenesis/shuffling methods can be combined with high-throughput, automated screening methods to detect activity of cloned, mutagenized polypeptides expressed by host cells.

Mutagenized DNA molecules that encode active polypeptides can be recovered from the host cells and rapidly sequenced using standard methods in the art. These methods allow the rapid determination of the importance of individual amino acid residues in a polypeptide.

The polypeptide may be a hybrid polypeptide in which a region of one polypeptide is fused at the N-terminus or the C-terminus of a region of another polypeptide.

The polypeptide may be a fusion polypeptide or cleavable fusion polypeptide in which another polypeptide is fused at the N-terminus or the C-terminus of the polypeptide of the present invention. A fusion polypeptide is produced by fusing a polynucleotide encoding another polypeptide to a polynucleotide of the present invention. Techniques for producing fusion polypeptides are known in the art and include ligating the coding sequences encoding the polypeptides so that they are in frame and that expression of the fusion polypeptide is under control of the same promoter(s) and terminator. Fusion polypeptides may also be constructed using intein technology in which fusion polypeptides are created post-translationally.

A fusion polypeptide can further comprise a cleavage site between the two polypeptides. Upon secretion of the fusion protein, the site is cleaved releasing the two polypeptides.

Sources of Polypeptides Having RNase Activity

A polypeptide having endonuclease 1 ribonuclease activity may be obtained from any organism. In some examples, the endonuclease 1 ribonucleases are obtained from microorganisms. The microorganisms may be from any genus. In some examples, the endonuclease 1 ribonucleases may be obtained from fungi or bacteria. Herein, the disclosed polynucleotides encoding endonuclease 1 ribonucleases polypeptides were obtained from the microorganisms set forth below. In other words, these microorganisms may be considered natural hosts for the RNases. The RNases may be obtained from other microorganisms, however. In some examples, the endonuclease 1 ribonucleases may be obtained from organisms into which a polynucleotide encoding the RNase has been inserted (e.g., a recombinant organism). Other organisms may be a source for endonuclease 1 ribonucleases.

In one aspect, the polynucleotides and/or polypeptides disclosed herein may be obtained from any living organism. In one aspect, the polynucleotides and/or polypeptides disclosed herein may be obtained from eukaryotes. In one aspect, the polynucleotides and/or polypeptides disclosed herein may be obtained from archaea. In one aspect, the polynucleotides and/or polypeptides disclosed herein may be obtained from prokaryotes. In one aspect, the polynucleotides and/or polypeptides disclosed herein may be obtained from Gram-positive bacteria. In one aspect, the polynucleotides and/or polypeptides disclosed herein may be obtained from Gram-negative bacteria.

In one aspect, the polynucleotides and/or polypeptides disclosed herein may be obtained from organisms of the genera *Bacillus, Saccharopolyspora* or *Streptomyces*. In one aspect, the polynucleotides and/or polypeptides disclosed herein may be obtained from *Bacillus mojavensis, Bacillus subtilis, Bacillus pumilus, Bacillus subtilis* subsp. *spizizenii,* *Saccharopolyspora hirsuta, Bacillus licheniformis, Streptomyces thermocarboxydus* or *Saccharopolyspora gregorii*.

It will be understood that for the aforementioned species, the invention encompasses both the perfect and imperfect states, and other taxonomic equivalents, e.g., anamorphs, regardless of the species name by which they are known. Those skilled in the art will readily recognize the identity of appropriate equivalents.

Strains of these species are readily accessible to the public in a number of culture collections, such as the American Type Culture Collection (ATCC), Deutsche Sammlung von Mikroorganismen und Zellkulturen GmbH (DSMZ), Centraalbureau Voor Schimmelcultures (CBS), and Agricultural Research Service Patent Culture Collection, Northern Regional Research Center (NRRL).

The polypeptide may be identified and obtained from other sources including microorganisms isolated from nature (e.g., soil, composts, water, etc.) or DNA samples obtained directly from natural materials (e.g., soil, composts, water, etc.) using the above-mentioned probes. Techniques for isolating microorganisms and DNA directly from natural habitats are well known in the art. A polynucleotide encoding the polypeptide may then be obtained by similarly screening a genomic DNA or cDNA library of another microorganism or mixed DNA sample. Once a polynucleotide encoding a polypeptide has been detected with the probe(s), the polynucleotide can be isolated or cloned by utilizing techniques that are known to those of ordinary skill in the art.

Compositions Containing RNases

The invention relates to compositions, preferably cleaning compositions, comprising an endonuclease 1 ribonuclease of the present invention in combination with one or more additional components.

Compositions for Cleaning

Generally, the endonuclease 1 RNase-containing compositions disclosed herein, and methods of using the compositions, are useful for cleaning. In some instances, the compositions may be useful for deep cleaning of items that contain organic stains such as body soil (e.g., sebum, sweat, dead cells, cell debris) and/or biofilms. In some instances, the compositions are useful for stain/soil removal, improving whiteness, prevention/reduction/removal of malodor, and/or for prevention or reduction of soil redeposition. There are no descriptions in the prior art that RNases have cleaning activity against such stains. However:

WO 2004/041988 (US 2005/0079594) discloses methods for removing biofilms using solutions containing combinations of enzymes, one which may be RNases;

WO 2006/031554 discloses methods for preventing, removing, reducing or disrupting a biofilm using alpha-amylases, which may be combined with other enzymes, including RNases;

WO 2008/153805 discloses detergents that may contain enzymes. Among many enzymes, RNases are disclosed.

In all the above disclosures, RNases are disclosed as part of laundry lists on enzymes that might be included in compositions. No effect of, or results from, use of RNases are described. No specific RNases are disclosed in those disclosures, for use in the methods or compositions that are disclosed therein.

One embodiment of the invention relates to a composition preferably a cleaning composition, such as a laundry composition, comprising an endonuclease 1 ribonuclease and at least one cleaning component. The cleaning component is preferably selected from the group consisting of: surfactants, builders, bleach components and polymers. One embodiment of the invention relates to a composition preferably a cleaning composition, such as a laundry composition, comprising a RNase, preferably an endonuclease 1 ribonuclease, wherein the RNase comprising one, two, three, four or all five amino acid sequences NREH (SEQ ID NO: 32), D[AEQ]DP (SEQ ID NO: 33), TDEDP (SEQ ID NO: 34), SHG and/or NREHVWA (SEQ ID NO: 35) and at least one cleaning component. The cleaning component is preferably selected from the group consisting of: surfactants, builders, bleach components and polymers.

One embodiment of the invention relates to a composition comprising:
 a) at least 0.001 ppm, such as at least 0.01 ppm or at least 0.1 ppm, of at least one polypeptide having RNase activity, preferably an endonuclease 1 ribonuclease, selected from the group consisting of: SEQ ID NO: 3, SEQ ID NO: 6, SEQ ID NO: 9, SEQ ID NO: 14, SEQ ID NO: 19, SEQ ID NO: 22, SEQ ID NO: 25, SEQ ID NO: 28 and SEQ ID NO: 31, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto; and
 b) at least one detergent adjunct ingredient.

One preferred embodiment of the invention relates to a composition comprising:
 a) at least 0.001 ppm, such as at least 0.01 ppm or at least 0.1 ppm, of at least one polypeptide having RNase activity, wherein the RNase is selected from the group consisting of: SEQ ID NO: 3, SEQ ID NO: 6, SEQ ID NO: 9 and SEQ ID NO: 14, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity thereto; and
 b) at least one detergent adjunct ingredient.

One preferred embodiment of the invention relates to a cleaning composition, preferably a laundry composition, comprising:
 a) at least 0.001 ppm, such as at least 0.01 ppm or at least 0.1 ppm of at least one polypeptide comprising a RNase, preferably an endonuclease 1 ribonuclease, wherein the RNase comprising one, two, three, four or all five amino acid sequences NREH (SEQ ID NO: 32), D[AEQ]DP (SEQ ID NO: 33), TDEDP (SEQ ID NO: 34), SHG and/or NREHVWA (SEQ ID NO: 35); and
 b) at least one cleaning component preferably selected from the group consisting of: surfactants, builders, bleach components, polymers, dispersing agents and additional enzymes.

One embodiment of the invention relates to a cleaning composition comprising:
 a) at least 0.001 ppm, including at least 0.01 ppm or at least 0.1 ppm, of at least one polypeptide having RNase activity, preferably an endonuclease 1, selected from the group consisting of: SEQ ID NO: 3, SEQ ID NO: 6, SEQ ID NO: 9, SEQ ID NO: 14, SEQ ID NO: 19, SEQ ID NO: 22, SEQ ID NO: 25, SEQ ID NO: 28 and SEQ ID NO: 31, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity hereto;
 b) at least one cleaning composition component, preferably selected from the group consisting of: surfactants, builders, bleach components, polymers, dispersing agents and additional enzymes.

One embodiment of the invention relates to a cleaning composition comprising:
 a) at least 0.001 ppm, including at least 0.01 ppm or at least 0.1 ppm, of at least one polypeptide having RNase activity, preferably an endonuclease 1, wherein the RNase is selected from the group consisting of: SEQ ID NO: 3, SEQ ID NO: 6, SEQ ID NO: 9 and SEQ ID NO: 14, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity hereto;
 b) at least one cleaning composition component, preferably selected from the group consisting of: surfactants, builders, bleach components, polymers, dispersing agents and additional enzymes.

The choice of cleaning components may include, for textile care, the consideration of the type of textile to be cleaned, the type and/or degree of soiling, the temperature at which cleaning is to take place, and the formulation of the detergent product. Although components mentioned below are categorized by general header according to a particular functionality, this is not to be construed as a limitation, as a component may comprise additional functionalities as will be appreciated by the skilled artisan.

In addition to an RNase, in some embodiments, the inventive compositions may contain a detergent/cleaning composition component and or a detergent adjunct ingredient. Examples of some of these are described below. The choice of additional components e.g. cleaning components is within the skill of the artisan and includes conventional ingredients, including the exemplary non-limiting components set forth below.

Surfactants

The cleaning e.g. detergent composition may comprise one or more surfactants, which may be anionic and/or cationic and/or non-ionic and/or semi-polar and/or zwitterionic, or a mixture thereof. In a particular embodiment, the detergent composition includes a mixture of one or more nonionic surfactants and one or more anionic surfactants. The surfactant(s) is typically present at a level of from about 0.1% to 60% by weight, such as about 1% to about 40%, or about 3% to about 20%, or about 3% to about 10%. The surfactant(s) is chosen based on the desired cleaning application, and may include any conventional surfactant(s) known in the art.

When included therein, the detergent will usually contain from about 1% to about 40% by weight of an anionic surfactant, such as from about 5% to about 30%, including from about 5% to about 15%, or from about 15% to about 20%, or from about 20% to about 25% of an anionic surfactant. Non-limiting examples of anionic surfactants include sulfates and sulfonates, in particular, linear alkylbenzenesulfonates (LAS), isomers of LAS, branched alkylbenzenesulfonates (BABS), phenylalkanesulfonates, alpha-olefinsulfonates (AOS), olefin sulfonates, alkene sulfonates, alkane-2,3-diylbis(sulfates), hydroxyalkanesulfonates and disulfonates, alkyl sulfates (AS) such as sodium dodecyl sulfate (SDS), fatty alcohol sulfates (FAS), primary alcohol sulfates (PAS), alcohol ethersulfates (AES or AEOS or FES, also known as alcohol ethoxysulfates or fatty alcohol ether sulfates), secondary alkanesulfonates (SAS), paraffin sulfonates (PS), ester sulfonates, sulfonated fatty acid glycerol esters, alpha-sulfo fatty acid methyl esters (alpha-SFMe or SES) including methyl ester sulfonate (MES), alkyl- or alkenylsuccinic acid, dodecenyl/tetradecenyl succinic acid (DTSA), fatty acid derivatives of amino acids, diesters and monoesters of sulfo-succinic acid or salt of fatty acids (soap), and combinations thereof.

When included therein the detergent will usually contain from about 1% to about 40% by weigh of a cationic surfactant, for example from about 0.5% to about 30%, in particular from about 1% to about 20%, from about 3% to about 10%, such as from about 3% to about 5%, from about 8% to about 12% or from about 10% to about 12%. Non-limiting examples of cationic surfactants include alkyldimethylethanolamine quat (ADMEAQ), cetyltrimethylammonium bromide (CTAB), dimethyldistearylammonium chloride (DSDMAC), and alkylbenzyldimethylammonium, alkyl quaternary ammonium compounds, alkoxylated quaternary ammonium (AQA) compounds, ester quats, and combinations thereof.

When included therein the detergent will usually contain from about 0.2% to about 40% by weight of a nonionic surfactant, for example from about 0.5% to about 30%, in particular from about 1% to about 20%, from about 3% to about 10%, such as from about 3% to about 5%, from about 8% to about 12%, or from about 10% to about 12%. Non-limiting examples of nonionic surfactants include alcohol ethoxylates (AE or AEO), alcohol propoxylates, propoxylated fatty alcohols (PFA), alkoxylated fatty acid alkyl esters, such as ethoxylated and/or propoxylated fatty acid alkyl esters, alkylphenol ethoxylates (APE), nonylphenol ethoxylates (NPE), alkylpolyglycosides (APG), alkoxylated amines, fatty acid monoethanolamides (FAM), fatty acid diethanolamides (FADA), ethoxylated fatty acid monoethanolamides (EFAM), propoxylated fatty acid monoethanolamides (PFAM), polyhydroxyalkyl fatty acid amides, or N-acyl N-alkyl derivatives of glucosamine (glucamides, GA, or fatty acid glucamides, FAGA), as well as products available under the trade names SPAN® and TWEEN®, and combinations thereof.

When included therein the detergent will usually contain from about 0.1% to about 10% by weight of a semipolar surfactant. Non-limiting examples of semipolar surfactants include amine oxides (AO) such as alkyldimethylamineoxide, N-(coco alkyl)-N,N-dimethylamine oxide and N-(tallow-alkyl)-N,N-bis(2-hydroxyethyl)amine oxide, and combinations thereof.

When included therein the detergent will usually contain from about 0.1% to about 10% by weight of a zwitterionic surfactant. Non-limiting examples of zwitterionic surfactants include betaines such as alkyldimethylbetaines, sulfobetaines, and combinations thereof.

In some embodiments, any of the above surfactants may be excluded from the compositions disclosed herein.

Builders and Co-Builders

The cleaning e.g. detergent composition may contain about 0-65% by weight, such as about 5% to about 50% of a detergent builder or co-builder, or a mixture thereof. In a dish wash detergent, the level of builder is typically 40-65%, particularly 50-65%. The builder and/or co-builder may particularly be a chelating agent that forms water-soluble complexes with Ca and Mg. Any builder and/or co-builder known in the art for use in cleaning detergents may be utilized. Non-limiting examples of builders include zeolites, diphosphates (pyrophosphates), triphosphates such as sodium triphosphate (STP or STPP), carbonates such as sodium carbonate, soluble silicates such as sodium metasilicate, layered silicates (e.g., SKS-6 from Hoechst), ethanolamines such as 2-aminoethan-1-ol (MEA), diethanolamine (DEA, also known as 2,2'-iminodiethan-1-ol), triethanolamine (TEA, also known as 2,2',2"-nitrilotriethan-1-ol), and (carboxymethyl)inulin (CMI), and combinations thereof.

The detergent composition may also contain 0-50% by weight, such as about 5% to about 30%, of a detergent co-builder. The detergent composition may include a co-builder alone, or in combination with a builder, for example a zeolite builder. Non-limiting examples of co-builders include homopolymers of polyacrylates or copolymers thereof, such as poly(acrylic acid) (PAA) or copoly(acrylic acid/maleic acid) (PAA/PMA). Further non-limiting examples include citrate, chelators such as aminocarboxylates, aminopolycarboxylates and phosphonates, and alkyl- or alkenylsuccinic acid. Additional specific examples include 2,2',2"-nitrilotriacetic acid (NTA), ethylenediaminetetraacetic acid (EDTA), diethylenetriaminepentaacetic acid (DTPA), iminodisuccinic acid (IDS), ethylenediamine-N,N'-disuccinic acid (EDDS), methylglycinediacetic acid (MGDA), glutamic acid-N,N-diacetic acid (GLDA), 1-hydroxyethane-1,1-diphosphonic acid (HEDP), ethylenediaminetetra(methylenephosphonic acid) (EDTMPA), diethylenetriaminepentakis (methylenephosphonic acid) (DTMPA or DTPMPA), N-(2-hydroxyethyl)iminodiacetic acid (EDG), aspartic acid-N-monoacetic acid (ASMA), aspartic acid-N,N-diacetic acid (ASDA), aspartic acid-N-monopropionic acid (ASMP), iminodisuccinic acid (IDA), N-(2-sulfomethyl)-aspartic acid (SMAS), N-(2-sulfoethyl)-aspartic acid (SEAS), N-(2-sulfomethyl)-glutamic acid (SMGL), N-(2-sulfoethyl)-glutamic acid (SEGL), N-methyliminodiacetic acid (MIDA), α-alanine-N,N-diacetic acid (α-ALDA), serine-N,N-diacetic acid (SEDA), isoserine-N,N-diacetic acid (ISDA), phenylalanine-N,N-diacetic acid (PHDA), anthranilic acid-N,N-diacetic acid (ANDA), sulfanilic acid-N,N-diacetic acid (SLDA), taurine-N,N-diacetic acid (TUDA) and sulfomethyl-N,N-diacetic acid (SMDA), N-(2-hydroxyethyl)ethylenediamine-N,N',N"-triacetic acid (HEDTA), diethanolglycine (DEG), diethylenetriamine penta(methylenephosphonic acid) (DTPMP), aminotris(methylenephosphonic acid) (ATMP), and combinations and salts thereof.

In some embodiments, any of the above builders and/or co-builders may be excluded from the compositions disclosed herein.

Bleaching Systems

The cleaning e.g. detergent composition may contain 0-30% by weight, such as about 1% to about 20%, of a bleaching system. Any bleaching system comprising components known in the art for use in cleaning detergents may be utilized. Suitable bleaching system components include sources of hydrogen peroxide; sources of peracids; and bleach catalysts or boosters.

Sources of Hydrogen Peroxide:

Suitable sources of hydrogen peroxide are inorganic persalts, including alkali metal salts such as sodium percarbonate and sodium perborates (usually mono- or tetrahydrate), and hydrogen peroxide-urea (1/1).

Sources of Peracids:

Peracids may be (a) incorporated directly as preformed peracids or (b) formed in situ in the wash liquor from hydrogen peroxide and a bleach activator (perhydrolysis) or (c) formed in situ in the wash liquor from hydrogen peroxide and a perhydrolase and a suitable substrate for the latter, e.g., an ester.
  a) Suitable preformed peracids include, but are not limited to, peroxycarboxylic acids such as peroxybenzoic acid and its ring-substituted derivatives, peroxy-α-naphthoic acid, peroxyphthalic acid, peroxylauric acid, peroxystearic acid, ε-phthalimidoperoxycaproic acid [phthalimidoperoxyhexanoic acid (PAP)], and o-carboxybenzamidoperoxycaproic acid; aliphatic and aromatic diperoxydicarboxylic acids such as diperoxydodecanedioic acid, diperoxyazelaic acid, diperoxysebacic acid, diperoxybrassylic acid, 2-decyldiperoxybutanedioic acid, and diperoxyphthalic, -isophthalic and -terephthalic acids; perimidic acids; peroxymonosulfuric acid; peroxydisulfuric acid; peroxyphosphoric acid; peroxysilicic acid; and mixtures of said compounds. It is understood that the peracids mentioned may in some cases be best added as suitable salts, such as alkali metal salts (e.g., Oxone®) or alkaline earth-metal salts.
  b) Suitable bleach activators include those belonging to the class of esters, amides, imides, nitriles or anhydrides and, where applicable, salts thereof. Suitable examples are tetraacetylethylenediamine (TAED), sodium 4-[(3,5,5-trimethylhexanoyl)oxy]benzene-1-sulfonate (ISONOBS), sodium 4-(dodecanoyloxy)benzene-1-sulfonate (LOBS), sodium 4-(decanoyloxy)benzene-1-sulfonate, 4-(decanoyloxy)benzoic acid (DOBA), sodium 4-(nonanoyloxy)benzene-1-sulfonate (NOBS), and/or those disclosed in WO98/17767. A particular family of bleach activators of interest was disclosed in EP624154 and particularly preferred in that family is acetyl triethyl citrate (ATC). ATC or a short chain triglyceride like triacetin has the advantage that they are environmentally friendly. Furthermore, acetyl triethyl citrate and triacetin have good hydrolytical stability in the product upon storage and are efficient bleach activators. Finally, ATC is multifunctional, as the citrate released in the perhydrolysis reaction may function as a builder.

In some embodiments, any of the above components may be excluded from the compositions disclosed herein.

Bleach Catalysts and Boosters

The bleaching system may also include a bleach catalyst or booster.

Some non-limiting examples of bleach catalysts that may be used in the compositions of the present invention include manganese oxalate, manganese acetate, manganese-collagen, cobalt-amine catalysts and manganese triazacyclononane (MnTACN) catalysts; particularly preferred are complexes of manganese with 1,4,7-trimethyl-1,4,7-triazacyclononane (Me3-TACN) or 1,2,4,7-tetramethyl-1,4,7-triazacyclononane (Me4-TACN), in particular Me3-TACN, such as the dinuclear manganese complex [(Me3-TACN)Mn(O)3Mn(Me3-TACN)](PF6)2, and [2,2',2''-nitrilotris(ethane-1,2-diylazanylylidene-κN-methanylylidene)triphenolato-κ3O]manganese(II). The bleach catalysts may also be other metal compounds, such as iron or cobalt complexes.

In some embodiments, where a source of a peracid is included, an organic bleach catalyst or bleach booster may be used having one of the following formulae:

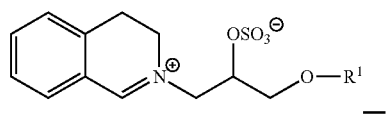

(i)

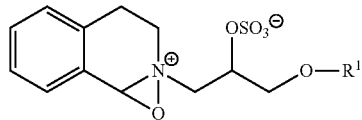

(ii)

or (iii) and mixtures thereof; wherein each R1 is independently a branched alkyl group containing from 9 to 24 carbons or linear alkyl group containing from 11 to 24 carbons, preferably each R1 is independently a branched alkyl group containing from 9 to 18 carbons or linear alkyl group containing from 11 to 18 carbons, more preferably each R1 is independently selected from the group consisting of 2-propylheptyl, 2-butyloctyl, 2-pentylnonyl, 2-hexyldecyl, dodecyl, tetradecyl, hexadecyl, octadecyl, isononyl, isodecyl, isotridecyl and isopentadecyl.

Other exemplary bleaching systems are described in the art. Suitable photobleaches may for example be sulfonated zinc or aluminium phthalocyanines.

In some embodiments, any of the above bleach catalysts and/or boosters may be excluded from the compositions disclosed herein.

Metal Care Agents

Metal care agents may prevent or reduce the tarnishing, corrosion or oxidation of metals, including aluminium, stainless steel and non-ferrous metals, such as silver and copper. Suitable examples include one or more of the following:
  (a) benzatriazoles, including benzotriazole or bis-benzotriazole and substituted derivatives thereof. Benzotriazole derivatives are those compounds in which the available substitution sites on the aromatic ring are partially or completely substituted. Suitable substituents include linear or branch-chain C1-C20-alkyl groups (e.g., C1-C20-alkyl groups) and hydroxyl, thio, phenyl or halogen such as fluorine, chlorine, bromine and iodine.
  (b) metal salts and complexes chosen from the group consisting of zinc, manganese, titanium, zirconium, hafnium, vanadium, cobalt, gallium and cerium salts and/or complexes, the metals being in one of the oxidation states II, Ill, IV, V or VI. In one aspect, suitable metal salts and/or metal complexes may be chosen from the group consisting of Mn(II) sulphate, Mn(II) citrate, Mn(II) stearate, Mn(II) acetylacetonate, K^TiF6 (e.g., K2TiF6), K^ZrF6 (e.g., K2ZrF6), CoSO4, Co(NOs)2 and Ce(NOs)3, zinc salts, for example zinc sulphate, hydrozincite or zinc acetate;
  (c) silicates, including sodium or potassium silicate, sodium disilicate, sodium metasilicate, crystalline phyllosilicate and mixtures thereof.

Further suitable organic and inorganic redox-active substances that act as silver/copper corrosion inhibitors are disclosed in the art. Preferably the composition of the invention comprises from 0.1 to 5% by weight of the composition of a metal care agent, preferably the metal care agent is a zinc salt.

In some embodiments, any of the above metal care agents may be excluded from the compositions disclosed herein.

Hydrotropes

The cleaning e.g. detergent composition may contain 0-10% by weight, for example 0-5% by weight, such as about 0.5 to about 5%, or about 3% to about 5%, of a hydrotrope. Any hydrotrope known in the art for use in detergents may be utilized. Non-limiting examples of hydrotropes include sodium benzenesulfonate, sodium p-toluene sulfonate (STS), sodium xylene sulfonate (SXS), sodium cumene sulfonate (SCS), sodium cymene sulfonate, amine oxides, alcohols and polyglycolethers, sodium hydroxynaphthoate, sodium hydroxynaphthalene sulfonate, sodium ethylhexyl sulfate, and combinations thereof.

In some embodiments, any of the above hydrotropes may be excluded from the compositions disclosed herein.

Polymers

The cleaning e.g. detergent composition may contain 0-10% by weight, such as 0.5-5%, 2-5%, 0.5-2% or 0.2-1% of a polymer. Any polymer known in the art for use in detergents may be utilized. The polymer may function as a co-builder as mentioned above, or may provide antiredeposition, fiber protection, soil release, dye transfer inhibition, grease cleaning and/or anti-foaming properties. Some polymers may have more than one of the above-mentioned properties and/or more than one of the below-mentioned motifs. Exemplary polymers include (carboxymethyl)cellulose (CMC), poly(vinyl alcohol) (PVA), poly(vinylpyrrolidone) (PVP), poly(ethyleneglycol) or poly(ethylene oxide) (PEG), ethoxylated poly(ethyleneimine), carboxymethyl inulin (CMI), and polycarboxylates such as PAA, PAA/PMA, poly-aspartic acid, and lauryl methacrylate/acrylic acid copolymers, hydrophobically modified CMC (HM-CMC) and silicones, copolymers of terephthalic acid and oligomeric glycols, copolymers of poly(ethylene terephthalate) and poly(oxyethene terephthalate) (PET-POET), PVP, poly(vinylimidazole) (PVI), poly(vinylpyridine-N-oxide) (PVPO or PVPNO) and polyvinylpyrrolidone-vinylimidazole (PVPVI). Suitable examples include PVP-K15, PVP-K30, ChromaBond S-400, ChromaBond S-403E and Chromabond S-100 from Ashland Aqualon, and Sokalan® HP 165, Sokalan® HP 50 (Dispersing agent), Sokalan® HP 53 (Dispersing agent), Sokalan® HP 59 (Dispersing agent), Sokalan® HP 56 (dye transfer inhibitor), Sokalan® HP 66 K (dye transfer inhibitor) from BASF. Further exemplary polymers include sulfonated polycarboxylates, polyethylene oxide and polypropylene oxide (PEO-PPO) and diquaternium ethoxy sulfate. Other exemplary polymers are disclosed in, e.g., WO 2006/130575. Salts of the above-mentioned polymers are also contemplated. Particularly preferred polymer is ethoxylated homopolymer Sokalan® HP 20 from BASF, which helps to prevent redeposition of soil in the wash liquor.

In some embodiments, any of the above polymers may be excluded from the compositions disclosed herein.

Fabric Hueing Agents

The cleaning e.g. detergent compositions of the present invention may also include fabric hueing agents such as dyes or pigments, which when formulated in detergent compositions can deposit onto a fabric when said fabric is contacted with a wash liquor comprising said detergent compositions and thus altering the tint of said fabric through absorption/reflection of visible light. Fluorescent whitening agents emit at least some visible light. In contrast, fabric hueing agents alter the tint of a surface as they absorb at least a portion of the visible light spectrum. Suitable fabric hueing agents include dyes and dye-clay conjugates, and may also include pigments. Suitable dyes include small molecule dyes and polymeric dyes. Suitable small molecule dyes include small molecule dyes selected from the group consisting of dyes falling into the Colour Index (C.I.) classifications of Direct Blue, Direct Red, Direct Violet, Acid Blue, Acid Red, Acid Violet, Basic Blue, Basic Violet and Basic Red, or mixtures thereof. The detergent composition preferably comprises from about 0.00003 wt % to about 0.2 wt %, from about 0.00008 wt % to about 0.05 wt %, or even from about 0.0001 wt % to about 0.04 wt % fabric hueing agent. The composition may comprise from 0.0001 wt % to 0.2 wt % fabric hueing agent, this may be especially preferred when the composition is in the form of a unit dose pouch. Other suitable hueing agents are described in the art.

In some embodiments, any of the above fabric hueing agents may be excluded from the compositions disclosed herein.

Enzymes

The detergent additive as well as the cleaning e.g. detergent composition may comprise one or more additional enzymes such as at least one lipase, cutinase, amylase, carbohydrase, cellulase, pectinase, mannanase, arabinase, galactanase, xylanase, oxidase, e.g., laccase, and/or peroxidase.

In general, the properties of the selected enzyme(s) should be compatible with the selected detergent, (i.e., pH-optimum, compatibility with other enzymatic and non-enzymatic ingredients, etc.), and the enzyme(s) should be present in effective amounts. In some embodiments, one or more of the above-listed enzymes may be specifically excluded from the compositions disclosed herein.

Examples of additional enzymes are described below.

Cellulases

Suitable cellulases include those of bacterial or fungal origin. Chemically modified or protein engineered mutants are included. Suitable cellulases include cellulases from the genera *Bacillus, Pseudomonas, Humicola, Fusarium, Thielavia, Acremonium*, e.g., the fungal cellulases produced from *Humicola insolens, Myceliophthora thermophila* and *Fusarium oxysporum.*

Especially suitable cellulases are the alkaline or neutral cellulases having colour care benefits.

Other cellulases are endo-beta-1,4-glucanase enzyme having a sequence of at least 97% identity to the amino acid sequence of position 1 to position 773 of SEQ ID NO:2 of WO 2002/099091 or a family 44 xyloglucanase, which a xyloglucanase enzyme having a sequence of at least 60% identity to positions 40-559 of SEQ ID NO: 2 of WO 2001/062903.

Commercially available cellulases include Celluzyme™, and Carezyme™ (Novozymes A/S), Carezyme Premium™ (Novozymes A/S), Celluclean™ (Novozymes A/S), Celluclean Classic™ (Novozymes A/S), Cellusoft™ (Novozymes A/S), Whitezyme™ (Novozymes A/S), Clazinase™, Puradax HA™ (Genencor International Inc.), and KAC-500(B)™ (Kao Corporation).

In some embodiments, one or more cellulases may be excluded from the compositions disclosed herein.

Mannanases

Suitable mannanases include those of bacterial or fungal origin. Chemically or genetically modified mutants are included. The mannanase may be an alkaline mannanase of Family 5 or 26. It may be a wild-type from *Bacillus* or *Humicola*, particularly *B. agaradhaerens, B. licheniformis, B. halodurans, B. clausii*, or *H. insolens*. A commercially available mannanase is Mannaway (Novozymes A/S).

In some embodiments, one or more mannanases may be excluded from the compositions disclosed herein.

Peroxidases/Oxidases

A suitable peroxidase includes a peroxidase enzyme comprised by the enzyme classification EC 1.11.1.7, as set out by the Nomenclature Committee of the International Union of Biochemistry and Molecular Biology (IUBMB), or any fragment derived therefrom, exhibiting peroxidase activity.

Suitable peroxidases/oxidases include those of plant, bacterial or fungal origin. Chemically modified or protein engineered mutants are included. Examples of useful peroxidases include peroxidases from *Coprinus*, e.g., from *C. cinereus*, and variants thereof. Commercially available peroxidases include Guardzyme™ (Novozymes A/S).

A suitable peroxidase includes a haloperoxidase enzyme, such as chloroperoxidase, bromoperoxidase and compounds exhibiting chloroperoxidase or bromoperoxidase activity. Haloperoxidases are classified according to their specificity for halide ions. Chloroperoxidases (E.C. 1.11.1.10) catalyze formation of hypochlorite from chloride ions. Preferably, the haloperoxidase is a vanadium haloperoxidase, i.e., a vanadate-containing haloperoxidase. Haloperoxidases have been isolated from many different fungi, in particular from the fungus group dematiaceous hyphomycetes, such as Caldariomyces, e.g., *C. fumago, Alternaria, Curvularia*, e.g., *C. verruculosa* and *C. inaequalis, Drechslera, Ulocladium* and *Botrytis*.

Haloperoxidases have also been isolated from bacteria such as *Pseudomonas*, e.g., *P. pyrrocinia* and *Streptomyces*, e.g., *S. aureofaciens*.

A suitable oxidase includes in particular, any laccase enzyme comprised by the enzyme classification EC 1.10.3.2, or any fragment derived therefrom exhibiting laccase activity, or a compound exhibiting a similar activity, such as a catechol oxidase (EC 1.10.3.1), an o-aminophenol oxidase (EC 1.10.3.4), or a bilirubin oxidase (EC 1.3.3.5). Preferred laccase enzymes are enzymes of microbial origin. The enzymes may be derived from plants, bacteria or fungi (including filamentous fungi and yeasts). Suitable examples from fungi include a laccase derivable from a strain of *Aspergillus, Neurospora*, e.g., *N. crassa, Podospora, Botrytis, Collybia, Fomes, Lentinus, Pleurotus, Trametes*, e.g., *T. villosa* and *T. versicolor, Rhizoctonia*, e.g., *R. solani, Coprinopsis*, e.g., *C. cinerea, C. comatus, C. friesii*, and *C. plicatilis, Psathyrella*, e.g., *P. condelleana, Panaeolus*, e.g., *P. papilionaceus, Myceliophthora*, e.g., *M. thermophila, Schytalidium*, e.g., *S. thermophilum, Polyporus*, e.g., *P. pinsitus, Phlebia*, e.g., *P. radiata*, or *Coriolus*, e.g., *C. hirsutus*. Suitable examples from bacteria include a laccase derivable from a strain of *Bacillus*. A laccase derived from *Coprinopsis* or *Myceliophthora* is preferred; in particular, a laccase derived from *Coprinopsis cinerea*; or from *Myceliophthora thermophila*.

In some embodiments, one or more peroxidases and/or oxidases may be excluded from the compositions disclosed herein.

Lipases and Cutinases

Suitable lipases and cutinases include those of bacterial or fungal origin. Chemically modified or protein engineered mutant enzymes are included. Examples include lipase from *Thermomyces*, e.g. from T. *lanuginosus* (previously named *Humicola lanuginosa*), cutinase from *Humicola*, e.g. *H. insolens*, lipase from strains of *Pseudomonas* (some of these now renamed to *Burkholderia*), e.g., *P. alcaligenes* or *P. pseudoalcaligenes, P. cepacia*, P. sp. strain SD705, *P. wisconsinensis*, GDSL-type *Streptomyces* lipases, cutinase from *Magnaporthe grisea*, cutinase from *Pseudomonas mendocina*, lipase from *Thermobifida fusca, Geobacillus stearothermophilus* lipase, lipase from *Bacillus subtilis*, and lipase from *Streptomyces griseus* and *S. pristinaespiralis*.

Other examples are lipase variants that are described in the art.

Preferred commercial lipase products include Lipolase™, Lipex™; Lipolex™ and Lipoclean™ (Novozymes A/S), Lumafast (originally from Genencor) and Lipomax (originally from Gist-Brocades).

Still other examples are lipases sometimes referred to as acyltransferases or perhydrolases, e.g. acyltransferases with homology to *Candida antarctica* lipase A, acyltransferase from *Mycobacterium smegmatis*, perhydrolases from the CE 7 family, and variants of the *M. smegmatis* perhydrolase, in particular the S54V variant used in the commercial product Gentle Power Bleach from Huntsman Textile Effects Pte Ltd.

In some embodiments, one or more lipases and/or cutinases may be excluded from the compositions disclosed herein.

Amylases

Suitable amylases include alpha-amylases and/or a glucoamylases and may be of bacterial or fungal origin. Chemically modified or protein engineered mutants are included. Amylases include, for example, alpha-amylases obtained from *Bacillus*, e.g., a special strain of *Bacillus licheniformis*, described in more detail in GB 1,296,839.

Suitable amylases include amylases having SEQ ID NO: 2 in WO 1995/010603 or variants having 90% sequence identity to SEQ ID NO: 3 thereof. Preferred variants are described in WO 1994/002597, WO 1994/018314, WO 1997/043424 and SEQ ID NO: 4 of WO 1999/019467, such as variants with substitutions in one or more of the following positions: 15, 23, 105, 106, 124, 128, 133, 154, 156, 178, 179, 181, 188, 190, 197, 201, 202, 207, 208, 209, 211, 243, 264, 304, 305, 391, 408, and 444.

Different suitable amylases include amylases having SEQ ID NO: 6 in WO 2002/010355 or variants thereof having 90% sequence identity to SEQ ID NO: 6. Preferred variants of SEQ ID NO: 6 are those having a deletion in positions 181 and 182 and a substitution in position 193.

Other amylases which are suitable are hybrid alpha-amylase comprising residues 1-33 of the alpha-amylase derived from *B. amyloliquefaciens* shown in SEQ ID NO: 6 of WO 2006/066594 and residues 36-483 of the *B. licheniformis* alpha-amylase shown in SEQ ID NO: 4 of WO 2006/066594 or variants having 90% sequence identity thereof. Preferred variants of this hybrid alpha-amylase are those having a substitution, a deletion or an insertion in one of more of the following positions: G48, T49, G107, H156, A181, N190, M197, I201, A209 and Q264. Most preferred variants of the hybrid alpha-amylase comprising residues 1-33 of the alpha-amylase derived from *B. amyloliquefaciens* shown in SEQ ID NO: 6 of WO 2006/066594 and residues 36-483 of SEQ ID NO: 4 are those having the substitutions:

M197T;

H156Y+A181T+N190F+A209V+Q264S; or

G48A+T491+G107A+H156Y+A181T+N190F+I201F+ A209V+Q264S.

Further amylases which are suitable are amylases having SEQ ID NO: 6 in WO 1999/019467 or variants thereof having 90% sequence identity to SEQ ID NO: 6. Preferred variants of SEQ ID NO: 6 are those having a substitution, a deletion or an insertion in one or more of the following positions: R181, G182, H183, G184, N195, I206, E212, E216 and K269. Particularly preferred amylases are those having deletion in positions R181 and G182, or positions H183 and G184.

Additional amylases which can be used are those having SEQ ID NO: 1, SEQ ID NO: 3, SEQ ID NO: 2 or SEQ ID NO: 7 of WO 1996/023873 or variants thereof having 90% sequence identity to SEQ ID NO: 1, SEQ ID NO: 2, SEQ ID NO: 3 or SEQ ID NO: 7. Preferred variants of SEQ ID NO: 1, SEQ ID NO: 2, SEQ ID NO: 3 or SEQ ID NO: 7 are those having a substitution, a deletion or an insertion in one or more of the following positions: 140, 181, 182, 183, 184, 195, 206, 212, 243, 260, 269, 304 and 476, using SEQ ID 2 of WO 96/023873 for numbering. More preferred variants are those having a deletion in two positions selected from 181, 182, 183 and 184, such as 181 and 182, 182 and 183, or positions 183 and 184. Most preferred amylase variants of SEQ ID NO: 1, SEQ ID NO: 2 or SEQ ID NO: 7 are those having a deletion in positions 183 and 184 and a substitution in one or more of positions 140, 195, 206, 243, 260, 304 and 476.

Other amylases which can be used are amylases having SEQ ID NO: 2 of WO 2008/153815, SEQ ID NO: 10 in WO 2001/066712 or variants thereof having 90% sequence identity to SEQ ID NO: 2 of WO 2008/153815 or 90% sequence identity to SEQ ID NO: 10 in WO 2001/066712. Preferred variants of SEQ ID NO: 10 in WO 2001/066712 are those having a substitution, a deletion or an insertion in one of more of the following positions: 176, 177, 178, 179, 190, 201, 207, 211 and 264.

Further suitable amylases are amylases having SEQ ID NO: 2 of WO 2009/061380 or variants having 90% sequence identity to SEQ ID NO: 2 thereof. Preferred variants of SEQ ID NO: 2 are those having a truncation of the C-terminus and/or a substitution, a deletion or an insertion in one of more of the following positions: Q87, Q98, S125, N128, T131, T165, K178, R180, S181, T182, G183, M201, F202, N225, S243, N272, N282, Y305, R309, D319, Q320, Q359, K444 and G475. More preferred variants of SEQ ID NO: 2 are those having the substitution in one of more of the following positions: Q87E,R, Q98R, S125A, N128C, T131I, T165I, K178L, T182G, M201L, F202Y, N225E,R, N272E, R, S243Q,A,E,D, Y305R, R309A, Q320R, Q359E, K444E and G475K and/or deletion in position R180 and/or S181 or of T182 and/or G183. Most preferred amylase variants of SEQ ID NO: 2 are those having the substitutions:

N128C+K178L+T182G+Y305R+G475K;
N128C+K178L+T182G+F202Y+Y305R+D319T+ G475K;
S125A+N128C+K178L+T182G+Y305R+G475K; or
S125A+N128C+T131I+T165I+K178L+T182G+ Y305R+G475K wherein the variants are C-terminally truncated and optionally further comprises a substitution at position 243 and/or a deletion at position 180 and/or position 181.

Further suitable amylases are amylases having SEQ ID NO: 1 of WO 2013/184577 or variants having 90% sequence identity to SEQ ID NO: 1 thereof. Preferred variants of SEQ ID NO: 1 are those having a substitution, a deletion or an insertion in one of more of the following positions: K176, R178, G179, T180, G181, E187, N192, M199, I203, S241, R458, T459, D460, G476 and G477. More preferred variants of SEQ ID NO: 1 are those having the substitution in one of more of the following positions: K176L, E187P, N192FYH, M199L, I203YF, S241QADN, R458N, T459S, D460T, G476K and G477K and/or deletion in position R178 and/or S179 or of T180 and/or G181. Most preferred amylase variants of SEQ ID NO: 1 are those having the substitutions:

E187P+I203Y+G476K
E187P+I203Y+R458N+T459S+D460T+G476K wherein the variants optionally further comprise a substitution at position 241 and/or a deletion at position 178 and/or position 179.

Further suitable amylases are amylases having SEQ ID NO: 1 of WO 2010/104675 or variants having 90% sequence identity to SEQ ID NO: 1 thereof. Preferred variants of SEQ ID NO: 1 are those having a substitution, a deletion or an insertion in one of more of the following positions: N21, D97, V128 K177, R179, S180, I181, G182, M200, L204, E242, G477 and G478. More preferred variants of SEQ ID NO: 1 are those having the substitution in one of more of the following positions: N21D, D97N, V128I K177L, M200L, L204YF, E242QA, G477K and G478K and/or deletion in position R179 and/or S180 or of I181 and/or G182. Most preferred amylase variants of SEQ ID NO: 1 are those having the substitutions:

N21 D+D97N+V128I wherein the variants optionally further comprise a substitution at position 200 and/or a deletion at position 180 and/or position 181.

Other suitable amylases are the alpha-amylase having SEQ ID NO: 12 in WO 2001/066712 or a variant having at least 90% sequence identity to SEQ ID NO: 12. Preferred amylase variants are those having a substitution, a deletion or an insertion in one of more of the following positions of SEQ ID NO: 12 in WO 2001/066712: R28, R118, N174; R181, G182, D183, G184, G186, W189, N195, M202, Y298, N299, K302, S303, N306, R310, N314; R320, H324, E345, Y396, R400, W439, R444, N445, K446, Q449, R458, N471, N484. Particular preferred amylases include variants having a deletion of D183 and G184 and having the substitutions R118K, N195F, R320K and R458K, and a variant additionally having substitutions in one or more position selected from the group: M9, G149, G182, G186, M202, T257, Y295, N299, M323, E345 and A339, most preferred a variant that additionally has substitutions in all these positions.

Other examples are amylase variants such as those described in WO 2011/098531, WO 2013/001078 and WO 2013/001087.

Commercially available amylases are Duramyl™, Termamyl™, Fungamyl™, Stainzyme™, Stainzyme Plus™, Natalase™, Liquozyme X and BAN™ (from Novozymes A/S), and Rapidase™, Purastar™/Effectenz™, Powerase, Preferenz S1000, Preferenz S100 and Preferenz S110 (from Genencor International Inc./DuPont).

In some embodiments, one or more amylases may be excluded from the compositions disclosed herein.

Proteases

Suitable proteases include those of bacterial, fungal, plant, viral or animal origin e.g. vegetable or microbial origin. Microbial origin is preferred. Chemically modified or protein engineered mutants are included. It may be an alkaline protease, such as a serine protease or a metalloprotease. A serine protease may for example be of the S1 family, such as trypsin, or the S8 family such as subtilisin. A metalloproteases protease may for example be a thermolysin from e.g. family M4 or other metalloprotease such as those from M5, M7 or M8 families.

The term "subtilases" refers to a sub-group of serine protease according to Siezen et al., Protein Engng. 4 (1991) 719-737 and Siezen et al. Protein Science 6 (1997) 501-523. Serine proteases are a subgroup of proteases characterized by having a serine in the active site, which forms a covalent adduct with the substrate. The subtilases may be divided into 6 sub-divisions, i.e. the Subtilisin family, the Thermitase family, the Proteinase K family, the Lantibiotic peptidase family, the Kexin family and the Pyrolysin family.

Examples of subtilases are those derived from *Bacillus* such as *Bacillus lentus, B. alkalophilus, B. subtilis, B.*

*amyloliquefaciens, Bacillus pumilus* and *Bacillus gibsonii*, and subtilisin *lentus*, subtilisin Novo, subtilisin Carlsberg, *Bacillus licheniformis*, subtilisin BPN', subtilisin 309, subtilisin 147 and subtilisin 168 and protease PD138 described in (WO 1993/018140). Other useful proteases may be those described in WO 1992/175177, WO 2001/016285, WO 2002/026024 and WO 2002/016547. Examples of trypsin-like proteases are trypsin (e.g. of porcine or bovine origin) and the *Fusarium* protease, and the chymotrypsin proteases derived from Cellumonas.

A further preferred protease is the alkaline protease from *Bacillus lentus* DSM 5483, and variants thereof.

Examples of metalloproteases are the neutral metalloprotease, such as those derived from *Bacillus amyloliquefaciens*.

Examples of useful proteases are the variants described in: WO 1992/019729, WO 1996/034946, WO 98/20115, WO 98/20116, WO 99/011768, WO 01/44452, WO 03/006602, WO 04/03186, WO 04/041979, WO 07/006305, WO 11/036263, WO 11/036264, especially the variants with substitutions in one or more of the following positions: 3, 4, 9, 15, 24, 27, 42, 55, 59, 60, 66, 74, 85, 96, 97, 98, 99, 100, 101, 102, 104, 116, 118, 121, 126, 127, 128, 154, 156, 157, 158, 161, 164, 176, 179, 182, 185, 188, 189, 193, 198, 199, 200, 203, 206, 211, 212, 216, 218, 226, 229, 230, 239, 246, 255, 256, 268 and 269 wherein the positions correspond to the positions of the *Bacillus lentus* protease shown in SEQ ID NO 1 of WO 2016/001449. More preferred the subtilase variants may comprise one of more of the following mutations: S3T, V41, S9R, S9E, A15T, S24G, S24R, K27R, N42R, S55P, G59E, G59D, N60D, N60E, V66A, N74D, N85S, N85R, G96S, G96A, S97G, S97D, S97A, S97SD, S99E, S99D, S99G, S99M, S99N, S99R, S99H, S101A, V102I, V102Y, V102N, S104A, G116V, G116R, H118D, H118N, N120S, S126L, P127Q, S128A, S154D, A156E, G157D, G157P, S158E, Y161A, R164S, Q176E, N179E, S182E, Q185N, A188P, G189E, V193M, N198D, V199I, Y203W, S206G, L211Q, L211 D, N212D, N212S, M216S, A226V, K229L, Q230H, Q239R, N246K, N255W, N255D, N255E, L256E, L256D T268A, R269H.

The protease variants are preferably variants of the *Bacillus lentus* protease (Savinase®) shown in SEQ ID NO 1 of WO 2016/001449, the *Bacillus amyloliquefaciens* protease (BPN') shown in SEQ ID NO 2 of WO2016/001449. The protease variants preferably have at least 80% sequence identity to SEQ ID NO 1 or SEQ ID NO 2 of WO 2016/001449.

A protease variant comprising a substitution at one or more positions corresponding to positions 171, 173, 175, 179, or 180 of SEQ ID NO: 1 of WO2004/067737, wherein said protease variant has a sequence identity of at least 75% but less than 100% to SEQ ID NO: 1 of WO 2004/067737.

Suitable commercially available protease enzymes include those sold under the trade names Alcalase®, Duralase™, Durazym™, Relase®, Relase® Ultra, Savinase®, Savinase® Ultra, Primase®, Polarzyme®, Kannase®, Liquanase®, Liquanase® Ultra, Ovozyme®, Coronase®, Coronase® Ultra, Blaze®, Blaze Evity® 100T, Blaze Evity® 125T, Blaze Evity® 150T, Neutrase®, Everlase® and Esperase® (Novozymes A/S), those sold under the tradename Maxatase®, Maxacal®, Maxapem®, Purafect Ox®, Purafect OxP®, Puramax®, FN2®, FN3®, FN4®, Excellase®, Excellenz P1000™, Excellenz P1250™, Eraser®, Preferenz P100™, Purafect Prime®, Preferenz P110™, Effectenz P1000™, Purafect®™, Effectenz P1050™, Purafect Ox®™, Effectenz P2000™, Purafast®, Properase®, Opticlean® and Optimase® (Danisco/DuPont), Axapem™ (Gist-Brocases N.V.), BLAP (sequence shown in FIG. 29 of U.S. Pat. No. 5,352,604) and variants hereof (Henkel AG) and KAP (*Bacillus alkalophilus* subtilisin) from Kao.

In some embodiments, one or more proteases may be excluded from the compositions disclosed herein.

Dispersants

The detergent compositions of the present invention can also contain dispersants. In particular, powdered detergents may comprise dispersants. Suitable water-soluble organic materials include the homo- or co-polymeric acids or their salts, in which the polycarboxylic acid comprises at least two carboxyl radicals separated from each other by not more than two carbon atoms. Suitable dispersants are for example described in Powdered Detergents, Surfactant science series volume 71, Marcel Dekker.

In some embodiments, any of the above dispersants may be excluded from the compositions disclosed herein.

Dye Transfer Inhibiting Agents

The cleaning e.g. detergent compositions of the present invention may also include one or more dye transfer inhibiting agents. Suitable polymeric dye transfer inhibiting agents include, but are not limited to, polyvinylpyrrolidone polymers, polyamine N-oxide polymers, copolymers of N-vinylpyrrolidone and N-vinylimidazole, polyvinyloxazolidones and polyvinylimidazoles or mixtures thereof. When present in a subject composition, the dye transfer inhibiting agents may be present at levels from about 0.0001% to about 10%, from about 0.01% to about 5% or even from about 0.1% to about 3% by weight of the composition.

In some embodiments, any of the above dye transfer inhibiting agents may be excluded from the compositions disclosed herein.

Fluorescent Whitening Agent

The cleaning e.g. detergent compositions of the present invention will preferably also contain additional components that may tint articles being cleaned, such as fluorescent whitening agent or optical brighteners. Where present the brightener is preferably at a level of about 0.01% to about 0.5%. Any fluorescent whitening agent suitable for use in a laundry detergent composition may be used in the composition of the present invention. The most commonly used fluorescent whitening agents are those belonging to the classes of diaminostilbene-sulfonic acid derivatives, diarylpyrazoline derivatives and bisphenyl-distyryl derivatives. Examples of the diaminostilbene-sulfonic acid derivative type of fluorescent whitening agents include the sodium salts of: 4,4'-bis-(2-diethanolamino-4-anilino-s-triazin-6-ylamino) stilbene-2,2'-disulfonate, 4,4'-bis-(2,4-dianilino-s-triazin-6-ylamino) stilbene-2.2'-disulfonate, 4,4'-bis-(2-anilino-4-(N-methyl-N-2-hydroxy-ethylamino)-s-triazin-6-ylamino) stilbene-2,2'-disulfonate, 4,4'-bis-(4-phenyl-1,2,3-triazol-2-yl)stilbene-2,2'-disulfonate and sodium 5-(2H-naphtho[1,2-d][1,2,3]triazol-2-yl)-2-[(E)-2-phenylvinyl]benzenesulfonate. Preferred fluorescent whitening agents are Tinopal DMS and Tinopal CBS available from Ciba-Geigy AG, Basel, Switzerland. Tinopal DMS is the disodium salt of 4,4'-bis-(2-morpholino-4-anilino-s-triazin-6-ylamino) stilbene-2,2'-disulfonate. Tinopal CBS is the disodium salt of 2,2'-bis-(phenyl-styryl)-disulfonate. Also preferred are fluorescent whitening agents is the commercially available Parawhite KX, supplied by Paramount Minerals and Chemicals, Mumbai, India. Other fluorescers suitable for use in the invention include the 1-3-diaryl pyrazolines and the 7-alkylaminocoumarins. Suitable fluorescent brightener levels include lower levels of from about 0.01, from 0.05, from about 0.1 or even from about 0.2 wt % to upper levels of 0.5 or even 0.75 wt %.

In some embodiments, any of the above fluorescent whitening agents or optical brighteners may be excluded from the compositions disclosed herein.

Soil Release Polymers

The cleaning e.g. detergent compositions of the present invention may also include one or more soil release polymers which aid the removal of soils from fabrics such as cotton and polyester based fabrics, in particular the removal of hydrophobic soils from polyester based fabrics. The soil release polymers may for example be nonionic or anionic terephthalte based polymers, polyvinyl caprolactam and related copolymers, vinyl graft copolymers, or polyester polyamides. Another type of soil release polymers are amphiphilic alkoxylated grease cleaning polymers comprising a core structure and a plurality of alkoxylate groups attached to that core structure. The core structure may comprise a polyalkylenimine structure or a polyalkanolamine structure. Furthermore, random graft co-polymers are suitable soil release polymers. Suitable graft co-polymers are described in more detail in the prior art. Suitable polyethylene glycol polymers include random graft co-polymers comprising: (i) hydrophilic backbone comprising polyethylene glycol; and (ii) side chain(s) selected from the group consisting of: C4-C25 alkyl group, polypropylene, polybutylene, vinyl ester of a saturated C1-C6 mono-carboxylic acid, CI-C 6 alkyl ester of acrylic or methacrylic acid, and mixtures thereof. Suitable polyethylene glycol polymers have a polyethylene glycol backbone with random grafted polyvinyl acetate side chains. The average molecular weight of the polyethylene glycol backbone can be in the range of from 2,000 Da to 20,000 Da, or from 4,000 Da to 8,000 Da. The molecular weight ratio of the polyethylene glycol backbone to the polyvinyl acetate side chains can be in the range of from 1:1 to 1:5, or from 1:1.2 to 1:2. The average number of graft sites per ethylene oxide units can be less than 1, or less than 0.8, the average number of graft sites per ethylene oxide units can be in the range of from 0.5 to 0.9, or the average number of graft sites per ethylene oxide units can be in the range of from 0.1 to 0.5, or from 0.2 to 0.4. A suitable polyethylene glycol polymer is Sokalan® HP22. Other soil release polymers are substituted polysaccharide structures especially substituted cellulosic structures such as modified cellulose derivaities. Suitable cellulosic polymers include cellulose, cellulose ethers, cellulose esters, cellulose amides and mixtures thereof. Suitable cellulosic polymers include anionically modified cellulose, nonionically modified cellulose, cationically modified cellulose, zwitterionically modified cellulose, and mixtures thereof. Suitable cellulosic polymers include methyl cellulose, carboxy methyl cellulose, ethyl cellulose, hydroxyl ethyl cellulose, hydroxyl propyl methyl cellulose, ester carboxy methyl cellulose, and mixtures thereof.

In some embodiments, any of the above soil release polymers may be excluded from the compositions disclosed herein.

Anti-Redeposition Agents

The cleaning e.g. detergent compositions of the present invention may also include one or more anti-redeposition agents such as carboxymethylcellulose (CMC), polyvinyl alcohol (PVA), polyvinylpyrrolidone (PVP), polyoxyethylene and/or polyethyleneglycol (PEG), homopolymers of acrylic acid, copolymers of acrylic acid and maleic acid, and ethoxylated polyethyleneimines. The cellulose based polymers described under soil release polymers above may also function as anti-redeposition agents.

In some embodiments, any of the above anti-redeposition agents may be excluded from the compositions disclosed herein.

Rheology Modifiers

The cleaning e.g. detergent compositions of the present invention may also include one or more rheology modifiers, structurants or thickeners, as distinct from viscosity reducing agents. The rheology modifiers are selected from the group consisting of non-polymeric crystalline, hydroxyfunctional materials, polymeric rheology modifiers which impart shear thinning characteristics to the aqueous liquid matrix of a liquid detergent composition. The rheology and viscosity of the detergent can be modified and adjusted by methods known in the art.

In some embodiments, any of the above rheology modifiers may be excluded from the compositions disclosed herein.

Other Components

Other suitable cleaning composition components include, but are not limited to, anti-shrink agents, anti-wrinkling agents, bactericides, binders, carriers, dyes, enzyme stabilizers, fabric softeners, fillers, foam regulators, hydrotropes, perfumes, pigments, sod suppressors, solvents, and structurants for liquid detergents and/or structure elasticizing agents. In some embodiments, any of the above components may be excluded from the compositions disclosed herein.

Methods and Uses Comprising RNases

The RNases of the invention e.g. an endonuclease 1 ribonuclease, may be formulated into cleaning and detergent composition which may be applied ion laundry and dish wash processes. The RNases of the invention effectively reduced stains such as sebum, sweat, dead cell material, biofilm EPS and other organic material comprising RNA. In particular substances as biofilm stick to the surface of e.g. textiles and act as a "glue" for dirt and other substances which attached to the surface. This may result on malodor generation and/or increased redeposition effect, where dirt released in e.g. wash, and which is thus present in the washing liquid redeposit back to e.g. the textile.

Thus, one embodiment of the invention relates to the use of a cleaning composition according to the invention for:
  i. preventing, reducing or removing stickiness of the item;
  ii. preventing, reducing or removing biofilm or biofilm components from the item;
  iii. reducing or removing stains comprises pel from the item;
  iv. preventing, reducing or removing redeposition of soil during cleaning of the item;
  v. preventing, reducing or removing adherence of soil to the item;
  vi. maintaining or improving whiteness of the item; or
  vii. preventing, reducing or removing malodor from the item,
wherein the item is a textile, a hard surface or a dish ware.

One embodiment of the invention relates to the use of a RNase comprising one, two, three, four or all five amino acid sequences NREH (SEQ ID NO: 32), D[AEQ]DP (SEQ ID NO: 33), TDEDP (SEQ ID NO: 34), SHG and/or NREHVWA (SEQ ID NO: 35) or a cleaning composition comprising the RNase and at least one cleaning component for:
  i. preventing, reducing or removing stickiness of the item;
  ii. preventing, reducing or removing biofilm or biofilm components from the item;
  iii. reducing or removing stains comprises pel from the item;

iv. preventing, reducing or removing redeposition of soil during cleaning of the item;
v. preventing, reducing or removing adherence of soil to the item;
vi. maintaining or improving whiteness of the item; or
vii. preventing, reducing or removing malodor from the item,
wherein the item is a textile, a hard surface or a dish ware.

One embodiment of the invention relates to the use of a polypeptide having RNase activity comprising an amino acids sequence selected from the group consisting of: SEQ ID NO: 3, SEQ ID NO: 6, SEQ ID NO: 9, SEQ ID NO: 14, SEQ ID NO: 19, SEQ ID NO: 22, SEQ ID NO: 25, SEQ ID NO: 28 and SEQ ID NO: 31, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity hereto or a cleaning composition comprising the RNase and at least one cleaning component for:
  i. preventing, reducing or removing stickiness of the item;
  ii. preventing, reducing or removing biofilm or biofilm components from the item;
  iii. reducing or removing stains comprises pel from the item;
  iv. preventing, reducing or removing redeposition of soil during cleaning of the item;
  v. preventing, reducing or removing adherence of soil to the item;
  vi. maintaining or improving whiteness of the item; or
  vii. preventing, reducing or removing malodor from the item,
wherein the item is a textile, a hard surface or a dish ware.

The invention also relates to methods e.g. laundry compositions comprising RNases e.g. endonuclease 1 ribonucleases. Such methods include laundry and dish wash method, but also industrial and medical cleaning methods.

One embodiment of the invention relates to a method for laundering an item, comprising:
  (a) exposing the item to the composition comprising a RNase according the invention;
  (b) completing at least one wash cycle; and
  (c) optionally, rinsing the textile.

One embodiment of the invention relates to a method for laundering an item, comprising:
  (a) exposing the item to the composition comprising a RNase comprising one, two, three, four or all five amino acid sequences NREH (SEQ ID NO: 32), D[AEQ]DP (SEQ ID NO: 33), TDEDP (SEQ ID NO: 34), SHG and/or NREHVWA (SEQ ID NO: 35);
  (b) completing at least one wash cycle; and
  (c) optionally, rinsing the textile.

One embodiment of the invention relates to a method for laundering an item, comprising:
  (a) exposing the item to the composition comprising a polypeptide having RNase activity comprising an amino acids sequence selected from the group consisting of: SEQ ID NO: 3, SEQ ID NO: 6, SEQ ID NO: 9, SEQ ID NO: 14, SEQ ID NO: 19, SEQ ID NO: 22, SEQ ID NO: 25, SEQ ID NO: 28 and SEQ ID NO: 31, and polypeptides having at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% sequence identity hereto;
  (b) completing at least one wash cycle; and
  (c) optionally, rinsing the textile.

Polynucleotides

The present invention also relates to polynucleotides encoding a polypeptide of the present invention, as described herein. In one embodiment, the polynucleotide encoding the polypeptide of the present invention has been isolated.

In one embodiment, the present invention relates to a polynucleotide encoding a polypeptide having RNase activity, wherein the polynucleotide has a sequence identity to the mature polypeptide coding sequence of SEQ ID NO: 1, 4, 7, 10, 12 or 15 of at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 94%, 96%, 97%, 98%, 99% or 100%. In some embodiments, the polynucleotide has a sequence identity of at least any of the above values but is less than 100% identical to any of the SEQ ID NOs. listed above.

In one embodiment, the present invention relates to a polynucleotide encoding a polypeptide having RNase activity, wherein the polynucleotide has a sequence identity to the mature polypeptide coding sequence of SEQ ID NO: 17, 20, 23, 26 or 29 of at least 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 94%, 96%, 97%, 98%, 99% or 100%. In some embodiments, the polynucleotide has a sequence identity of at least any of the above values but is less than 100% identical to any of the SEQ ID NOs. listed above.

The polynucleotides encode polypeptides that have RNase activity. The polynucleotide may have been isolated.

The techniques used to isolate or clone a polynucleotide are known in the art and include isolation from genomic DNA or cDNA, or a combination thereof. The cloning of the polynucleotides from genomic DNA can be affected, e.g., by using the well-known polymerase chain reaction (PCR) or antibody screening of expression libraries to detect cloned DNA fragments with shared structural features. Other nucleic acid amplification procedures such as ligase chain reaction (LCR), ligation activated transcription (LAT) and polynucleotide-based amplification (NASBA) may be used.

Modification of a polynucleotide encoding a polypeptide of the present invention may be necessary for synthesizing polypeptides substantially similar to the polypeptide. The term "substantially similar" to the polypeptide refers to non-naturally occurring forms of the polypeptide.

In one aspect, the mature polypeptide coding sequence is nucleotides 79-864 of SEQ ID NO: 1, and nucleotides 1 to 78 of SEQ ID NO: 1 encode a signal peptide.

In one aspect, the mature polypeptide coding sequence is nucleotides 85-864 of SEQ ID NO: 4, and nucleotides 1 to 84 of SEQ ID NO: 4 encode a signal peptide.

In one aspect, the mature polypeptide coding sequence is nucleotides 79-864 of SEQ ID NO: 7, and nucleotides 1 to 78 of SEQ ID NO: 7 encode a signal peptide.

In one aspect, the mature polypeptide coding sequence is nucleotides 79-864 of SEQ ID NO: 10, and nucleotides 1 to 78 of SEQ ID NO: 10 encode a signal peptide.

In one aspect, the mature polypeptide coding sequence is nucleotides 79-864 of SEQ ID NO: 12, and nucleotides 1 to 78 of SEQ ID NO: 12 encode a signal peptide.

In one aspect, the mature polypeptide coding sequence is nucleotides 79-864 of SEQ ID NO: 15, and nucleotides 1 to 78 of SEQ ID NO: 15 encode a signal peptide.

In one aspect, the mature polypeptide coding sequence is nucleotides 82-771 of SEQ ID NO: 17, and nucleotides 1 to 81 of SEQ ID NO: 17 encode a signal peptide.

In one aspect, the mature polypeptide coding sequence is nucleotides 76-819 of SEQ ID NO: 20, and nucleotides 1 to 75 of SEQ ID NO: 20 encode a signal peptide.

In one aspect, the mature polypeptide coding sequence is nucleotides 106-819 of SEQ ID NO: 23, and nucleotides 1 to 105 of SEQ ID NO: 23 encode a signal peptide.

In one aspect, the mature polypeptide coding sequence is nucleotides 76-819 of SEQ ID NO: 26, and nucleotides 1 to 75 of SEQ ID NO: 26 encode a signal peptide.

In one aspect, the mature polypeptide coding sequence is nucleotides 82-807 of SEQ ID NO: 29, and nucleotides 1 to 81 of SEQ ID NO: 29 encode a signal peptide.

Nucleic Acid Constructs

The present invention also relates to nucleic acid constructs comprising a polynucleotide of the present invention operably linked to one or more control sequences that direct the expression of the coding sequence in a suitable host cell under conditions compatible with the control sequences.

The polynucleotide may be manipulated in a variety of ways to provide for expression of the polypeptide. Manipulation of the polynucleotide prior to its insertion into a vector may be desirable or necessary depending on the expression vector. The techniques for modifying polynucleotides utilizing recombinant DNA methods are well known in the art.

The control sequence may be a promoter, a polynucleotide that is recognized by a host cell for expression of a polynucleotide encoding a polypeptide of the present invention. The promoter contains transcriptional control sequences that mediate the expression of the polypeptide. The promoter may be any polynucleotide that shows transcriptional activity in the host cell including variant, truncated, and hybrid promoters, and may be obtained from genes encoding extracellular or intracellular polypeptides either homologous or heterologous to the host cell.

Examples of suitable promoters for directing transcription of the nucleic acid constructs of the present invention in a bacterial host cell are the promoters obtained from the *Bacillus amyloliquefaciens* alpha-amylase gene (amyQ), *Bacillus licheniformis* alpha-amylase gene (amyL), *Bacillus licheniformis* penicillinase gene (penP), *Bacillus stearothermophilus* maltogenic amylase gene (amyM), *Bacillus subtilis* levansucrase gene (sacB), *Bacillus subtilis* xylA and xylB genes, *Bacillus thuringiensis* cryIIIA gene, *E. coli* lac operon, *E. coli* trc promoter, *Streptomyces coelicolor* agarase gene (dagA), and prokaryotic beta-lactamase gene, as well as the tac promoter.

Examples of suitable promoters for directing transcription of the nucleic acid constructs of the present invention in a filamentous fungal host cell are promoters obtained from the genes for *Aspergillus nidulans* acetamidase, *Aspergillus niger* neutral alpha-amylase, *Aspergillus niger* acid stable alpha-amylase, *Aspergillus niger* or *Aspergillus awamori* glucoamylase (glaA), *Aspergillus oryzae* TAKA amylase, *Aspergillus oryzae* alkaline protease, *Aspergillus oryzae* triose phosphate isomerase, *Fusarium oxysporum* trypsin-like protease, *Fusarium venenatum* amyloglucosidase, *Fusarium venenatum* Daria, *Fusarium venenatum* Quinn, *Rhizomucor miehei* lipase, *Rhizomucor miehei* aspartic proteinase, *Trichoderma reesei* beta-glucosidase, *Trichoderma reesei* cellobiohydrolase 1, *Trichoderma reesei* cellobiohydrolase ll, *Trichoderma reesei* endoglucanase 1, *Trichoderma reesei* endoglucanase II, *Trichoderma reesei* endoglucanase II, *Trichoderma reesei* endoglucanase V, *Trichoderma reesei* xylanase 1, *Trichoderma reesei* xylanase ll, *Trichoderma reesei* xylanase lll, *Trichoderma reesei* beta-xylosidase, and *Trichoderma reesei* translation elongation factor, as well as the NA2-tpi promoter (a modified promoter from an 30 *Aspergillus* neutral alpha-amylase gene in which the untranslated leader has been replaced by an untranslated leader from an *Aspergillus* triose phosphate isomerase gene; non-limiting examples include modified promoters from an *Aspergillus niger* neutral alpha-amylase gene in which the untranslated leader has been replaced by an untranslated leader from an *Aspergillus nidulans* or *Aspergillus oryzae* triose phosphate isomerase gene); and variant, truncated, and hybrid promoters thereof.

In a yeast host, useful promoters are obtained from the genes for *Saccharomyces cerevisiae* enolase (ENO-1), *Saccharomyces cerevisiae* galactokinase (GAL1), *Saccharomyces cerevisiae* alcohol dehydrogenase/glyceraldehyde-3-phosphate dehydrogenase (ADH1, ADH2/GAP), *Saccharomyces cerevisiae* triose phosphate isomerase (TPI), *Saccharomyces cerevisiae* metallothionein (CUP1), and *Saccharomyces cerevisiae* 3-phosphoglycerate kinase.

The control sequence may also be a transcription terminator, which is recognized by a host cell to terminate transcription. The terminator is operably linked to the 3'-terminus of the polynucleotide encoding the polypeptide. Any terminator that is functional in the host cell may be used in the present invention.

Preferred terminators for bacterial host cells are obtained from the genes for *Bacillus clausii* alkaline protease (aprH), *Bacillus licheniformis* alpha-amylase (amyL), and *Escherichia coli* ribosomal RNA (rrnB).

Preferred terminators for filamentous fungal host cells are obtained from the genes for *Aspergillus nidulans* acetamidase, *Aspergillus nidulans* anthranilate synthase, *Aspergillus niger* glucoamylase, *Aspergillus niger* alpha-glucosidase, *Aspergillus oryzae* TAKA amylase, *Fusarium oxysporum* trypsin-like protease, *Trichoderma reesei* beta-glucosidase, *Trichoderma reesei* cellobiohydrolase I, *Trichoderma reesei* cellobiohydrolase II, *Trichoderma reesei* endoglucanase I, *Trichoderma reesei* endoglucanase II, *Trichoderma reesei* endoglucanase lll, *Trichoderma reesei* endoglucanase V, *Trichoderma reesei* xylanase I, *Trichoderma reesei* xylanase II, *Trichoderma reesei* xylanase lll, *Trichoderma reesei* beta-xylosidase, and *Trichoderma reesei* translation elongation factor.

Preferred terminators for yeast host cells are obtained from the genes for *Saccharomyces cerevisiae* enolase, *Saccharomyces cerevisiae* cytochrome C (CYC1), and *Saccharomyces cerevisiae* glyceraldehyde-3-phosphate dehydrogenase.

The control sequence may also be an mRNA stabilizer region downstream of a promoter and upstream of the coding sequence of a gene which increases expression of the gene.

Examples of suitable mRNA stabilizer regions are obtained from a *Bacillus thuringiensis* cryIIIA gene (WO 94/25612) and a *Bacillus subtilis* SP82 gene.

The control sequence may also be a leader, a nontranslated region of an mRNA that is important for translation by the host cell. The leader is operably linked to the 5'-terminus of the polynucleotide encoding the polypeptide. Any leader that is functional in the host cell may be used.

Preferred leaders for filamentous fungal host cells are obtained from the genes for *Aspergillus oryzae* TAKA amylase and *Aspergillus nidulans* triose phosphate isomerase.

Suitable leaders for yeast host cells are obtained from the genes for *Saccharomyces cerevisiae* enolase (ENO-1), *Saccharomyces cerevisiae 3-phosphoglycerate kinase, Saccharomyces cerevisiae alpha-factor, and Saccharomyces cerevisiae alcohol dehydrogenase/glyceraldehyde-3-phosphate dehydrogenase (ADH2/GAP).

The control sequence may also be a polyadenylation sequence, a sequence operably linked to the 3'-terminus of the polynucleotide and, when transcribed, is recognized by the host cell as a signal to add polyadenosine residues to transcribed mRNA. Any polyadenylation sequence that is functional in the host cell may be used.

Preferred polyadenylation sequences for filamentous fungal host cells are obtained from the genes for Aspergillus nidulans anthranilate synthase, Aspergillus niger glucoamylase, Aspergillus niger alpha-glucosidase Aspergillus oryzae TAKA amylase, and Fusarium oxysporum trypsin-like protease.

Useful polyadenylation sequences for yeast host cells are known in the art.

The control sequence may also be a signal peptide coding region that encodes a signal peptide linked to the N-terminus of a polypeptide and directs the polypeptide into the cell's secretory pathway. The 5'-end of the coding sequence of the polynucleotide may inherently contain a signal peptide coding sequence naturally linked in translation reading frame with the segment of the coding sequence that encodes the polypeptide. Alternatively, the 5'-end of the coding sequence may contain a signal peptide coding sequence that is foreign to the coding sequence. A foreign signal peptide coding sequence may be required where the coding sequence does not naturally contain a signal peptide coding sequence. Alternatively, a foreign signal peptide coding sequence may simply replace the natural signal peptide coding sequence in order to enhance secretion of the polypeptide. However, any signal peptide coding sequence that directs the expressed polypeptide into the secretory pathway of a host cell may be used.

Effective signal peptide coding sequences for bacterial host cells are the signal peptide coding sequences obtained from the genes for Bacillus NCIB 11837 maltogenic amylase, Bacillus licheniformis subtilisin, Bacillus licheniformis beta-lactamase, Bacillus stearothermophilus alpha-amylase, Bacillus stearothermophilus neutral proteases (nprT, nprS, nprM), and Bacillus subtilis prsA.

Effective signal peptide coding sequences for filamentous fungal host cells are the signal peptide coding sequences obtained from the genes for Aspergillus niger neutral amylase, Aspergillus niger glucoamylase, Aspergillus oryzae TAKA amylase, Humicola insolens cellulase, Humicola insolens endoglucanase V, Humicola lanuginosa lipase, and Rhizomucor miehei aspartic proteinase.

Useful signal peptides for yeast host cells are obtained from the genes for Saccharomyces cerevisiae alpha-factor and Saccharomyces cerevisiae invertase.

The control sequence may also be a propeptide coding sequence that encodes a propeptide positioned at the N-terminus of a polypeptide. The resultant polypeptide is known as a proenzyme or propolypeptide (or a zymogen in some cases). A propolypeptide is generally inactive and can be converted to an active polypeptide by catalytic or autocatalytic cleavage of the propeptide from the propolypeptide. The propeptide coding sequence may be obtained from the genes for Bacillus subtilis alkaline protease (aprE), Bacillus subtilis neutral protease (nprT), Myceliophthora thermophila laccase, Rhizomucor miehei aspartic proteinase, and Saccharomyces cerevisiae alpha-factor.

Where both signal peptide and propeptide sequences are present, the propeptide sequence is positioned next to the N-terminus of a polypeptide and the signal peptide sequence is positioned next to the N-terminus of the propeptide sequence.

It may also be desirable to add regulatory sequences that regulate expression of the polypeptide relative to the growth of the host cell. Examples of regulatory sequences are those that cause expression of the gene to be turned on or off in response to a chemical or physical stimulus, including the presence of a regulatory compound. Regulatory sequences in prokaryotic systems include the lac, tac, and trp operator systems. In yeast, the ADH2 system or GAL1 system may be used. In filamentous fungi, the Aspergillus niger glucoamylase promoter, Aspergillus oryzae TAKA alpha-amylase promoter, and Aspergillus oryzae glucoamylase promoter, Trichoderma reesei cellobiohydrolase I promoter, and Trichoderma reesei cellobiohydrolase II promoter may be used. Other examples of regulatory sequences are those that allow for gene amplification. In eukaryotic systems, these regulatory sequences include the dihydrofolate reductase gene that is amplified in the presence of methotrexate, and the metallothionein genes that are amplified with heavy metals. In these cases, the polynucleotide encoding the polypeptide would be operably linked to the regulatory sequence.

Expression Vectors

The present invention also relates to recombinant expression vectors comprising a polynucleotide of the present invention, a promoter, and transcriptional and translational stop signals. The various nucleotide and control sequences may be joined together to produce a recombinant expression vector that may include one or more convenient restriction sites to allow for insertion or substitution of the polynucleotide encoding the polypeptide at such sites. Alternatively, the polynucleotide may be expressed by inserting the polynucleotide or a nucleic acid construct comprising the polynucleotide into an appropriate vector for expression. In creating the expression vector, the coding sequence is located in the vector so that the coding sequence is operably linked with the appropriate control sequences for expression.

The recombinant expression vector may be any vector (e.g., a plasmid or virus) that can be conveniently subjected to recombinant DNA procedures and can bring about expression of the polynucleotide. The choice of the vector will typically depend on the compatibility of the vector with the host cell into which the vector is to be introduced. The vector may be a linear or closed circular plasmid.

The vector may be an autonomously replicating vector, i.e., a vector that exists as an extrachromosomal entity, the replication of which is independent of chromosomal replication, e.g., a plasmid, an extrachromosomal element, a minichromosome, or an artificial chromosome. The vector may contain any means for assuring self-replication. Alternatively, the vector may be one that, when introduced into the host cell, is integrated into the genome and replicated together with the chromosome(s) into which it has been integrated. Furthermore, a single vector or plasmid or two or more vectors or plasmids that together contain the total DNA to be introduced into the genome of the host cell, or a transposon, may be used.

The vector preferably contains one or more selectable markers that permit easy selection of transformed, transfected, transduced, or the like cells. A selectable marker is a gene the product of which provides for biocide or viral resistance, resistance to heavy metals, prototrophy to auxotrophs, and the like.

Examples of bacterial selectable markers are *Bacillus licheniformis* or *Bacillus subtilis* dal genes, or markers that confer antibiotic resistance such as ampicillin, chloramphenicol, kanamycin, neomycin, spectinomycin, or tetracycline resistance. Suitable markers for yeast host cells include, but are not limited to, ADE2, HIS3, LEU2, LYS2, MET3, TRP1, and URA3. Selectable markers for use in a filamentous fungal host cell include, but are not limited to, adeA (phosphoribosylaminoimidazole-succinocarboxamide synthase), adeB (phosphoribosyl-aminoimidazole synthase), amdS (acetamidase), argB (ornithine carbamoyltransferase), bar (phosphinothricin acetyltransferase), hph (hygromycin phosphotransferase), niaD (nitrate reductase), pyrG (orotidine-5'-phosphate decarboxylase), sC (sulfate adenyltransferase), and trpC (anthranilate synthase), as well as equivalents thereof. Preferred for use in an *Aspergillus* cell are *Aspergillus nidulans* or *Aspergillus oryzae* amdS and pyrG genes and a *Streptomyces hygroscopicus* bargene. Preferred for use in a *Trichoderma* cell are adeA, adeB, amdS, hph, and pyrG genes.

The selectable marker may be a dual selectable marker system. In one aspect, the dual selectable marker is an hph-tk dual selectable marker system.

The vector preferably contains one or more elements that permit integration of the vector into the host cell's genome or autonomous replication of the vector in the cell independent of the genome.

For integration into the host cell genome, the vector may rely on the polynucleotide's sequence encoding the polypeptide or any other element of the vector for integration into the genome by homologous or non-homologous recombination. Alternatively, the vector may contain additional polynucleotides for directing integration by homologous recombination into the genome of the host cell at a precise location(s) in the chromosome(s). To increase the likelihood of integration at a precise location, the integrational elements should contain a sufficient number of nucleic acids, such as 100 to 10,000 base pairs, 400 to 10,000 base pairs, and 800 to 10,000 base pairs, which have a high degree of sequence identity to the corresponding target sequence to enhance the probability of homologous recombination. The integrational elements may be any sequence that is homologous with the target sequence in the genome of the host cell. Furthermore, the integrational elements may be non-encoding or encoding polynucleotides. On the other hand, the vector may be integrated into the genome of the host cell by non-homologous recombination.

For autonomous replication, the vector may further comprise an origin of replication enabling the vector to replicate autonomously in the host cell in question. The origin of replication may be any plasmid replicator mediating autonomous replication that functions in a cell. The term "origin of replication" or "plasmid replicator" means a polynucleotide that enables a plasmid or vector to replicate in vivo.

Examples of bacterial origins of replication are the origins of replication of plasmids pBR322, pUC19, pACYC177, and pACYC184 permitting replication in *E. coli*, and pUB110, pE194, pTA1060, and pAMß1 permitting replication in *Bacillus*.

Examples of origins of replication for use in a yeast host cell are the 2 micron origin of replication, ARS1, ARS4, the combination of ARS1 and CEN3, and the combination of ARS4 and CEN6.

Examples of origins of replication useful in a filamentous fungal cell are AMA1 and ANS1. Isolation of the AMA1 gene and construction of plasmids or vectors comprising the gene can be accomplished according to the methods known in the art.

More than one copy of a polynucleotide of the present invention may be inserted into a host cell to increase production of a polypeptide. An increase in the copy number of the polynucleotide can be obtained by integrating at least one additional copy of the sequence into the host cell genome or by including an amplifiable selectable marker gene with the polynucleotide where cells containing amplified copies of the selectable marker gene, and thereby additional copies of the polynucleotide, can be selected for by cultivating the cells in the presence of the appropriate selectable agent.

The procedures used to ligate the elements described above to construct the recombinant expression vectors of the present invention are well known to one skilled in the art.

Host Cells

The present invention also relates to recombinant host cells, comprising a polynucleotide of the present invention operably linked to one or more control sequences that direct the production of a polypeptide of the present invention. A construct or vector comprising a polynucleotide is introduced into a host cell so that the construct or vector is maintained as a chromosomal integrant or as a self-replicating extra-chromosomal vector as described earlier. The term "host cell" encompasses any progeny of a parent cell that is not identical to the parent cell due to mutations that occur during replication. The choice of a host cell will to a large extent depend upon the gene encoding the polypeptide and its source.

The host cell may be any cell useful in the recombinant production of a polypeptide of the present invention, e.g., a prokaryote or a eukaryote.

The prokaryotic host cell may be any Gram-positive or Gram-negative bacterium. Gram-positive bacteria include, but are not limited to, *Bacillus, Clostridium, Enterococcus, Geobacillus, Lactobacillus, Lactococcus, Oceanobacillus, Staphylococcus, Streptococcus*, and *Streptomyces*. Gram-negative bacteria include, but are not limited to, *Campylobacter, E. coli, Flavobacterium, Fusobacterium, Helicobacter, Ilyobacter, Neisseria, Pseudomonas, Salmonella*, and *Ureaplasma*.

The bacterial host cell may be any *Bacillus* cell including, but not limited to, *Bacillus alkalophilus, Bacillus altitudinis, Bacillus amyloliquefaciens, B. amyloliquefaciens* subsp. *plantarum, Bacillus brevis, Bacillus circulans, Bacillus clausii, Bacillus coagulans, Bacillus firmus, Bacillus lautus, Bacillus lentus, Bacillus licheniformis, Bacillus megaterium, Bacillus methylotrophicus, Bacillus pumilus, Bacillus safensis, Bacillus stearothermophilus, Bacillus subtilis*, and *Bacillus thuringiensis* cells. The bacterial host cell may also be any *Streptococcus* cell including, but not limited to, *Streptococcus equisimilis, Streptococcus pyogenes, Streptococcus uberis*, and *Streptococcus equi* subsp. *Zooepidemicus* cells. The bacterial host cell may also be any *Streptomyces* cell including, but not limited to, *Streptomyces achromogenes, Streptomyces avermitilis, Streptomyces coelicolor, Streptomyces griseus*, and *Streptomyces lividans* cells.

Introduction of DNA into a *Bacillus* cell may be effected by protoplast transformation, competent cell transformation or conjugation. The introduction of DNA into an *E. coli* cell may be effected by protoplast transformation or electroporation. The introduction of DNA into a *Streptomyces* cell may be effected by protoplast transformation, electroporation, conjugation, or transduction. The introduction of DNA into a *Pseudomonas* cell may be effected by electroporation or conjugation. The introduction of DNA into a *Streptococcus* cell may be effected by natural competence, protoplast transformation, electroporation, or conjugation. However, any method known in the art for introducing DNA into a host cell can be used.

The host cell may also be a eukaryote, such as a mammalian, insect, plant, or fungal cell. The host cell may be a fungal cell. "Fungi" as used herein includes the phyla Ascomycota, Basidiomycota, Chytridiomycota, and Zygomycota as well as the Oomycota and all mitosporic fungi. The fungal host cell may be a yeast cell. "Yeast" as used herein includes ascosporogenous yeast (Endomycetales), basidiosporogenous yeast, and yeast belonging to the Fungi Imperfecti (Blastomycetes).

The yeast host cell may be a *Candida, Hansenula, Kluyveromyces, Pichia, Saccharomyces, Schizosaccharomyces*, or *Yarrowia* cell, such as a *Kluyveromyces lactis, Saccharomyces carlsbergensis, Saccharomyces cerevisiae, Saccharomyces diastaticus, Saccharomyces douglasii, Saccharomyces kluyveri, Saccharomyces norbensis, Saccharomyces oviformis*, or *Yarrowia lipolytica* cell.

The fungal host cell may be a filamentous fungal cell. "Filamentous fungi" include all filamentous forms of the subdivision Eumycota and Oomycota. The filamentous fungi are generally characterized by a mycelial wall composed of chitin, cellulose, glucan, chitosan, mannan, and other complex polysaccharides. Vegetative growth is by hyphal elongation and carbon catabolism is obligately aerobic. In contrast, vegetative growth by yeasts such as *Saccharomyces cerevisiae* is by budding of a unicellular thallus and carbon catabolism may be fermentative.

The filamentous fungal host cell may be an *Acremonium, Aspergillus, Aureobasidium, Bjerkandera, Ceriporiopsis, Chrysosporium, Coprinus, Coriolus, Cryptococcus, Filibasidium, Fusarium, Humicola, Magnaporthe, Mucor, Myceliophthora, Neocallimastix, Neurospora, Paecilomyces, Penicillium, Phanerochaete, Phlebia, Piromyces, Pleurotus, Schizophyllum, Talaromyces, Thermoascus, Thielavia, Tolypocladium, Trametes*, or *Trichoderma* cell. For example, the filamentous fungal host cell may be an *Aspergillus awamori, Aspergillus foetidus, Aspergillus fumigatus, Aspergillus japonicus, Aspergillus nidulans, Aspergillus niger, Aspergillus oryzae, Bjerkandera adusta, Ceriporiopsis aneirina, Ceriporiopsis caregiea, Ceriporiopsis gilvescens, Ceriporiopsis pannocinta, Ceriporiopsis rivulosa, Ceriporiopsis subrufa, Ceriporiopsis subvermispora, Chrysosporium inops, Chrysosporium keratinophilum, Chrysosporium lucknowense, Chrysosporium merdarium, Chrysosporium pannicola, Chrysosporium queenslandicum, Chrysosporium tropicum, Chrysosporium zonatum, Coprinus cinereus, Coriolus hirsutus, Fusarium bactridioides, Fusarium cerealis, Fusarium crookwellense, Fusarium culmorum, Fusarium graminearum, Fusarium graminum, Fusarium heterosporum, Fusarium negundi, Fusarium oxysporum, Fusarium reticulatum, Fusarium roseum, Fusarium sambucinum, Fusarium sarcochroum, Fusarium solani, Fusarium sporotrichioides, Fusarium sulphureum, Fusarium torulosum, Fusarium trichothecioides, Fusarium venenatum, Humicola insolens, Humicola lanuginosa, Mucor miehei, Myceliophthora thermophila, Neurospora crassa, Penicillium purpurogenum, Phanerochaete chrysosporium, Phlebia radiata, Pleurotus eryngii, Thielavia terrestris, Trametes villosa, Trametes versicolor, Trichoderma harzianum, Trichoderma koningii, Trichoderma longibrachiatum, Trichoderma reesei*, or *Trichoderma viride* cell.

Fungal cells may be transformed by a process involving protoplast formation, transformation of the protoplasts, and regeneration of the cell wall in a manner known per se. Suitable procedures for transformation of *Aspergillus* and *Trichoderma* host cells are known in the art. Suitable methods for transforming *Fusarium* species are known in the art. Yeast may also be transformed using the procedures known in the art.

Formulations

The compositions of the invention may be in any convenient form, e.g., a bar, a homogenous tablet, a tablet having two or more layers, a pouch having one or more compartments, a regular or compact powder, a granule, a paste, a gel, or a regular, compact or concentrated liquid.

Pouches can be configured as single or multicompartments. It can be of any form, shape and material which is suitable for hold the composition, e.g. without allowing the release of the composition to release of the composition from the pouch prior to water contact. The pouch is made from water soluble film which encloses an inner volume. Said inner volume can be divided into compartments of the pouch. Preferred films are polymeric materials preferably polymers which are formed into a film or sheet. Preferred polymers, copolymers or derivates thereof are selected polyacrylates, and water-soluble acrylate copolymers, methyl cellulose, carboxy methyl cellulose, sodium dextrin, ethyl cellulose, hydroxyethyl cellulose, hydroxypropyl methyl cellulose, malto dextrin, poly methacrylates, most preferably polyvinyl alcohol copolymers and, hydroxypropyl methyl cellulose (HPMC). Preferably the level of polymer in the film for example PVA is at least about 60%. Preferred average molecular weight will typically be about 20,000 to about 150,000. Films can also be of blended compositions comprising hydrolytically degradable and water-soluble polymer blends such as polylactide and polyvinyl alcohol (known under the Trade reference M8630 as sold by Mono-Sol LLC, Indiana, USA) plus plasticisers like glycerol, ethylene glycerol, propylene glycol, sorbitol and mixtures thereof. The pouches can comprise a solid laundry cleaning composition or part components and/or a liquid cleaning composition or part components separated by the water-soluble film. The compartment for liquid components can be different in composition than compartments containing solids.

Detergent ingredients can be separated physically from each other by compartments in water dissolvable pouches or in different layers of tablets. Thereby negative storage interaction between components can be avoided. Different dissolution profiles of each of the compartments can also give rise to delayed dissolution of selected components in the wash solution.

A liquid or gel detergent, which is not unit dosed, may be aqueous, typically containing at least 20% by weight and up to 95% water, such as up to about 70% water, up to about 65% water, up to about 55% water, up to about 45% water, up to about 35% water. Other types of liquids, including without limitation, alkanols, amines, diols, ethers and polyols may be included in an aqueous liquid or gel. An aqueous liquid or gel detergent may contain from 0-30% organic solvent. A liquid or gel detergent may be non-aqueous.

Liquid formulations may contain the RNase and may contain other small molecular material from the production process (e.g., fermentation of microorganisms expressing the RNase), for example, like salts, peptides, metabolites and the like.

Optionally, stabilizers (e.g., polyols, salts and the like) and other ingredients (e.g., inhibitors, antioxidants, antireductants, preservatives, alcohols, pH controllants, viscosity controllers and the like), may be contained in the formulations. The liquid formulations can be clear, hazy, or may contain sedimentation.

Polyols (or polyhydric alcohol) contained in liquid formulations generally are alcohols with two or more hydroxyl groups. The polyols typically have less than 10 carbons, such as 9, 8, 7, 6, 5, 4, or 3 carbons. The molecular weight is typically less than 500 g/mol, such as 400 g/mol or 300 g/mol. Examples of suitable polyols include, but are not limited to, glycerol, propylene glycol, ethylene glycol, sorbitol, mannitol, erythritol, dulcitol, inositol, xylitol, adonitol and the like. In some embodiments, the amount of polyol(s) in the liquid enzyme formulation is less than about 50% (w/w), 40% (w/w), 30% (w/w), 20% (w/w), or 10% (w/w). In some embodiments, the liquid enzyme formulation does not contain polyol. Inhibitors included added reversible inhibitors of the enzyme in question or of other enzymes intended for the same application or be an inhibitor of an unwanted side activity in the product or in the application.

In some examples, salts, especially those used as stabilizers, may be for the purpose of reducing water activity. Salts can be organic or inorganic and are typically dissolved in the liquid formulation. Examples of cations in the salts may include Na+, Ca++, K+, Mg++, and the like. Examples of anions in the salts may include chloride, formate, acetate, sulfate, and the like. The formulation can also be without added salt.

Antioxidants or antireductants may include, for example, methionine, scavengers, sulfites, and the like. Preservatives may include any food grade or technical grade preservative. Examples include sorbate, benzoate, isothiazolinones, BAC, phenoxyethanol, and the like.

Granular Detergent Formulations

The RNase-containing compositions may be formulated as granules. The granule is generally composed of a core, and optionally one or more coatings (outer layers) surrounding the core.

The core of a granule may include additional materials such as fillers, fiber materials (cellulose or synthetic fibres), stabilizing agents, solubilizing agents, suspension agents, viscosity regulating agents, light spheres, plasticizers, salts, lubricants and fragrances. The core may include binders, such as synthetic polymer, wax, fat, or carbohydrate. The core may comprise a salt of a multivalent cation, a reducing agent, an antioxidant, a peroxide decomposing catalyst and/or an acidic buffer component, typically as a homogenous blend. The core may consist of an inert particle with the enzyme absorbed into it, or applied onto the surface, e.g., by fluid bed coating. The core may have a diameter of 20-2000 µm, particularly 50-1500 µm, 100-1500 µm or 250-1200 µm.

The core can be prepared by granulating a blend of the ingredients, e.g., by a method comprising granulation techniques such as crystallization, precipitation, pan-coating, fluid bed coating, fluid bed agglomeration, rotary atomization, extrusion, prilling, spheronization, size reduction methods, drum granulation, and/or high shear granulation:

a) Spray dried products, wherein a liquid enzyme-containing solution is atomized in a spray drying tower to form small droplets which during their way down the drying tower dry to form an enzyme-containing particulate material. Very small particles can be produced this way;

b) Layered products, wherein the enzyme is coated as a layer around a pre-formed inert core particle, wherein an enzyme-containing solution is atomized, typically in a fluid bed apparatus wherein the pre-formed core particles are fluidized, and the enzyme-containing solution adheres to the core particles and dries up to leave a layer of dry enzyme on the surface of the core particle. Particles of a desired size can be obtained this way if a useful core particle of the desired size can be found;

c) Absorbed core particles, wherein rather than coating the enzyme as a layer around the core, the enzyme is absorbed onto and/or into the surface of the core;

d) Extrusion or pelletized products, wherein an enzyme-containing paste is pressed to pellets or under pressure is extruded through a small opening and cut into particles which are subsequently dried. Such particles usually have a considerable size because of the material in which the extrusion opening is made (usually a plate with bore holes) sets a limit on the allowable pressure drop over the extrusion opening. Also, very high extrusion pressures when using a small opening increase heat generation in the enzyme paste, which is harmful to the enzyme;

e) Prilled products, wherein an enzyme-containing powder is suspended in molten wax and the suspension is sprayed, e.g., through a rotating disk atomiser, into a cooling chamber where the droplets quickly solidify. The product obtained is one wherein the enzyme is uniformly distributed throughout an inert material instead of being concentrated on its surface;

f) Mixer granulation products, wherein a liquid is added to a dry powder composition of, e.g., conventional granulating components, the enzyme being introduced either via the liquid or the powder or both. The liquid and the powder are mixed and as the moisture of the liquid is absorbed in the dry powder, the components of the dry powder will start to adhere and agglomerate and particles will build up, forming granulates comprising the enzyme. In a particular product of this process, wherein various high-shear mixers can be used as granulators, granulates consisting of enzyme as enzyme, fillers and binders etc. are mixed with cellulose fibers to reinforce the particles to give the so-called T-granulate. Reinforced particles, being more robust, release less enzymatic dust;

g) Size reduction, wherein the cores are produced by milling or crushing of larger particles, pellets, tablets, briquettes etc. containing the enzyme. The wanted core particle fraction is obtained by sieving the milled or crushed product. Over and undersized particles can be recycled;

h) Fluid bed granulation, involves suspending particulates in an air stream and spraying a liquid onto the fluidized particles via nozzles. Particles hit by spray droplets get wetted and become tacky. The tacky particles collide with other particles and adhere to them and form a granule; or i) The cores may be subjected to drying, such as in a fluid bed drier. Other known methods for drying granules in the feed or detergent industry can be used by the skilled person. The drying preferably takes place at a product temperature of from 25 to 90° C. For some enzymes it is important the cores comprising the enzyme contain a low amount of water before coating. If water sensitive enzymes are coated before excessive water is removed, it will be trapped within the core and it may affect the activity of the enzyme negatively. After drying, the cores may contain 0.1-10% w/w water.

The core of the enzyme granule/particle may be surrounded by at least one coating, e.g., to improve the storage stability, to reduce dust formation during handling, or for coloring the granule. The optional coating(s) may include a salt coating, or other suitable coating materials, such as polyethylene glycol (PEG), methyl hydroxy-propyl cellulose (MHPC) and polyvinyl alcohol (PVA).

The coating may be applied in an amount of at least 0.1% by weight of the core, e.g., at least 0.5%, 1% or 5%. The amount may be at most 100%, 70%, 50%, 40% or 30%. The coating is preferably at least 0.1 µm thick, particularly at least 0.5 µm, at least 1 µm or at least 5 µm. In a particular embodiment the thickness of the coating is below 100 µm. In a more particular embodiment the thickness of the coating is below 60 µm. In an even more particular embodiment the total thickness of the coating is below 40 µm. The coating may encapsulate the core unit by forming a substantially continuous layer. A substantially continuous layer is to be understood as a coating having few or no holes, so that the core unit it is encapsulating/enclosing has few or none uncoated areas. The layer or coating should be homogeneous in thickness. The coating can further contain other materials as known in the art, e.g., fillers, antisticking agents, pigments, dyes, plasticizers and/or binders, such as titanium dioxide, kaolin, calcium carbonate or talc.

A salt coating may comprise at least 60% by weight w/w of a salt, e.g., at least 65%, at least 70%, at least 75%, at least 80%, at least 85%, at least 90%, at least 95% or at least 99% by weight w/w. The salt may be added from a salt solution where the salt is completely dissolved or from a salt suspension wherein the fine particles is less than 50 µm, such as less than 10 µm or less than 5 µm. The salt coating may comprise a single salt or a mixture of two or more salts. The salt may be water soluble, in particular having a solubility at least 0.1 grams in 100 g of water at 20° C., preferably at least 0.5 g per 100 g water, e.g., at least 1 g per 100 g water, e.g., at least 5 g per 100 g water. The salt may be an inorganic salt, e.g., salts of sulfate, sulfite, phosphate, phosphonate, nitrate, chloride or carbonate or salts of simple organic acids (less than 10 carbon atoms, e.g., 6 or less carbon atoms) such as citrate, malonate or acetate. Examples of cations in these salts are alkali or earth alkali metal ions, the ammonium ion or metal ions of the first transition series, such as sodium, potassium, magnesium, calcium, zinc or aluminium. Examples of anions include chloride, bromide, iodide, sulfate, sulfite, bisulfite, thiosulfate, phosphate, monobasic phosphate, dibasic phosphate, hypophosphite, dihydrogen pyrophosphate, tetraborate, borate, carbonate, bicarbonate, metasilicate, citrate, malate, maleate, malonate, succinate, lactate, formate, acetate, butyrate, propionate, benzoate, tartrate, ascorbate or gluconate. In particular, alkali- or earth alkali metal salts of sulfate, sulfite, phosphate, phosphonate, nitrate, chloride or carbonate or salts of simple organic acids such as citrate, malonate or acetate may be used.

The salt in the coating may have a constant humidity at 20° C. above 60%, particularly above 70%, above 80% or above 85%, or it may be another hydrate form of such a salt (e.g., anhydrate). Specific examples of suitable salts are NaCl (CH20° C.=76%), $Na_2CO_3$ (CH20° C.=92%), $NaNO_3$ (CH20° C.=73%), $Na_2HPO_4$ (CH20° C.=95%), $Na_3PO_4$ (CH25° C.=92%), $NH_4Cl$ (CH20° C.=79.5%), $(NH_4)_2HPO_4$ (CH20° C.=93.0%), $NH_4H_2PO_4$ (CH20° C.=93.1%), $(NH_4)_2 SO_4$ (CH20° C.=81.1%), KCl (CH20° C.=85%), $K_2HPO_4$ (CH20° C.=92%), $KH_2PO_4$ (CH20° C.=96.5%), $KNO_3$ (CH20° C.=93.5%), $Na_2SO_4$ (CH20° C.=93%), $K_2SO_4$ (CH20° C.=98%), $KHSO_4$ (CH20° C.=86%), $MgSO_4$ (CH20° C.=90%), $ZnSO_4$ (CH20° C.=90%) and sodium citrate (CH25° C.=86%). Other examples include $NaH_2PO_4$, $(NH_4)H_2PO_4$, $CuSO_4$, $Mg(NO_3)_2$ and magnesium acetate.

The salt may be in anhydrous form, or it may be a hydrated salt, i.e. a crystalline salt hydrate with bound water(s) of crystallization Specific examples include anhydrous sodium sulfate ($Na_2SO_4$), anhydrous magnesium sulfate ($MgSO_4$), magnesium sulfate heptahydrate ($MgSO_4 \cdot 7H_2O$), zinc sulfate heptahydrate ($ZnSO_4 \cdot 7H_2O$), sodium phosphate dibasic heptahydrate ($Na_2HPO_4 \cdot 7H_2O$), magnesium nitrate hexahydrate ($Mg(NO_3)_2(6H_2O)$), sodium citrate dihydrate and magnesium acetate tetrahydrate. Preferably the salt is applied as a solution of the salt, e.g., using a fluid bed.

Non-dusting granulates may be produced and may be coated by methods known in the art. Examples of waxy coating materials are poly(ethylene oxide) products (polyethyleneglycol, PEG) with mean molar weights of 1000 to 20000; ethoxylated nonylphenols having from 16 to 50 ethylene oxide units; ethoxylated fatty alcohols in which the alcohol contains from 12 to 20 carbon atoms and in which there are 15 to 80 ethylene oxide units; fatty alcohols; fatty acids; and mono- and di- and triglycerides of fatty acids. Examples of film-forming coating materials suitable for application by fluid bed techniques are given in GB 1483591. Liquid enzyme preparations may, for instance, be stabilized by adding a polyol such as propylene glycol, a sugar or sugar alcohol, lactic acid or boric acid according to established methods, generally prior to forming granules. Protected enzymes may be prepared.

Thus, in a further aspect, the present invention provides a granule, which comprises:
(a) a core comprising an endonuclease 1 RNase according to the invention, and
(b) optionally a coating consisting of one or more layer(s) surrounding the core.

The RNase-containing compositions may also be formulated as co-granules that combine one or more enzymes. Each enzyme will then be present in more granules securing a more uniform distribution of enzymes in the detergent. This also reduces the physical segregation of different enzymes due to different particle sizes. Methods for producing multi-enzyme co-granulate for the detergent industry are known in the art.

Another example of formulation of enzymes using co-granulates is known, which relates to a detergent composition comprising (a) a multi-enzyme co-granule; (b) less than 10% w/w zeolite (anhydrous basis); and (c) less than 10% w/w phosphate salt (anhydrous basis), wherein said enzyme co-granule comprises from 10 to 98% w/w moisture sink component and the composition additionally comprises from 20 to 80% w/w detergent moisture sink component.

The multi-enzyme co-granule may comprise an RNase of the invention and (a) one or more enzymes selected from lipases, hemicellulases, proteases, amylases, cellulases, cellobiose dehydrogenases, xylanases, phospho lipases, esterases, cutinases, pectinases, mannanases, pectate lyases, keratinases, reductases, oxidases, phenoloxidases, ligninases, pullulanases, tannases, pentosanases, lichenases glucanases, arabinosidases, hyaluronidase, chondroitinase, amylases, and mixtures thereof.

Fermentation Broth or Cells Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

Methods of Using the RNases and Compositions

The present invention also relates to a fermentation broth formulation or a cell composition comprising a polypeptide of the present invention. The fermentation broth product further comprises additional ingredients used in the fermentation process, such as, for example, cells (including, the host cells containing the gene encoding the polypeptide of the present invention which are used to produce the polypeptide of interest), cell debris, biomass, fermentation media and/or fermentation products. In some embodiments, the composition is a cell-killed whole broth containing organic acid(s), killed cells and/or cell debris, and culture medium.

The term "fermentation broth" as used herein refers to a preparation produced by cellular fermentation that undergoes no or minimal recovery and/or purification. For example, fermentation broths are produced when microbial cultures are grown to saturation, incubated under carbon-limiting conditions to allow protein synthesis (e.g., expression of enzymes by host cells) and secretion into cell culture medium. The fermentation broth can contain unfractionated or fractionated contents of the fermentation materials derived at the end of the fermentation. Typically, the fermentation broth is unfractionated and comprises the spent culture medium and cell debris present after the microbial cells (e.g., filamentous fungal cells) are removed, e.g., by centrifugation. In some embodiments, the fermentation broth contains spent cell culture medium, extracellular enzymes, and viable and/or nonviable microbial cells.

In some embodiments, the fermentation broth formulation and cell compositions comprise a first organic acid component comprising at least one 1-5 carbon organic acid and/or a salt thereof and a second organic acid component comprising at least one 6 or more carbon organic acid and/or a salt thereof. In a specific embodiment, the first organic acid component is acetic acid, formic acid, propionic acid, a salt thereof, or a mixture of two or more of the foregoing and the second organic acid component is benzoic acid, cyclohexanecarboxylic acid, 4-methylvaleric acid, phenylacetic acid, a salt thereof, or a mixture of two or more of the foregoing.

In one aspect, the composition contains an organic acid(s), and optionally further contains killed cells and/or cell debris. In one embodiment, the killed cells and/or cell debris are removed from a cell-killed whole broth to provide a composition that is free of these components.

The fermentation broth formulations or cell compositions may further comprise a preservative and/or anti-microbial (e.g., bacteriostatic) agent, including, but not limited to, sorbitol, sodium chloride, potassium sorbate, and others known in the art.

The cell-killed whole broth or composition may contain the unfractionated contents of the fermentation materials derived at the end of the fermentation. Typically, the cell-killed whole broth or composition contains the spent culture medium and cell debris present after the microbial cells (e.g., filamentous fungal cells) are grown to saturation, incubated under carbon-limiting conditions to allow protein synthesis. In some embodiments, the cell-killed whole broth or composition contains the spent cell culture medium, extracellular enzymes, and killed filamentous fungal cells. In some embodiments, the microbial cells present in the cell-killed whole broth or composition can be permeabilized and/or lysed using methods known in the art.

A whole broth or cell composition as described herein is typically a liquid, but may contain insoluble components, such as killed cells, cell debris, culture media components, and/or insoluble enzyme(s). In some embodiments, insoluble components may be removed to provide a clarified liquid composition.

EXAMPLES

Example 1. Identification of Genes Encoding Endonuclease 1 Ribonucleases

Using public and internal sequence databases, polypeptides containing Pfam PF04231 (endonuclease 1) amino acid sequence domains were identified (Finn, R. D., et al., 2016. The Pfam protein families database: towards a more sustainable future. Nucleic Acids Res 44, D279-D285). The polypeptides were used to generate a phylogenetic tree using a multiple alignment of mature polypeptide sequences containing at least one endonuclease 1 domain (FIG. 1). The sequences were aligned using the MUSCLE algorithm version 3.8.31 (Edgar, R. C., 2004. MUSCLE: multiple sequence alignment with high accuracy and high throughput. Nucleic Acids Res 32, 1792-1797). The phylogenetic trees were constructed using FastTree version 2.1.8 (Price, M. N., et al., 2010. FastTree 2—Approximately Maximum-Likelihood Trees for Large Alignments. PLOS ONE 5, e9490) and visualized using iTOL (Letunic, I., Bork, P., 2007. Interactive Tree Of Life (iTOL): an online tool for phylogenetic tree display and annotation. Bioinformatics 23, 127-128).

The phylogenetic tree obtained from this work is shown in FIG. 1. The Pfam PF04231-containing polypeptides separated into 5 different clusters: ENDO1 A, ENDO1 B, ENDO1 C, ENDO1 D and ENDO1 E. The ENDO1 A branch contains the $Mg^{2+}$-activated ribonuclease from *Bacillus subtilis* (Nakamura, A., et al., 1992. Gene cloning and characterization of a novel extracellular ribonuclease of *Bacillus subtilis*. European Journal of Biochemistry 209, 121-127). Within that branch of the phylogenetic tree, polypeptides from a number of bacterial strains in our strain database were identified (Table 1). The bacterial strains shown below in Table 1 were generally isolated from soil samples. Chromosomal DNA was isolated from the strain and subjected to full genome sequencing using Illumina technology. To clone the genes containing the Pfam PF04231 amino acid domains from the strains, PCR primers flanking the genes encoding the Pfam PF04231 domain-containing genes were designed and used to amplify the genes using chromosomal DNA as a template. The amplified regions were cloned and sequenced. Identification of the sequences that were ascertained/determined is shown in the section of this disclosure titled "Overview of Sequences." The actual sequences are set forth in the sequence listing that is part of this application.

TABLE 1

Organisms used in these studies

| Sample | Genus & species of organism | Source | Sequence identifier of mature peptide |
|---|---|---|---|
| 1 | *Bacillus mojavensis* | U.S. | SEQ ID NO: 3 |
| 2 | *Bacillus subtilis* | Denmark | SEQ ID NO: 6 |
| 3 | *Bacillus pumilus* | Denmark | SEQ ID NO: 9 |
| 4 | *Bacillus subtilis* subsp. *spizizenii* | U.S. | SEQ ID NO: 14 |
| 5 | *Saccharopolyspora hirsuta* | Unknown, isolated 1990 | SEQ ID NO: 19 |
| 6 | *Bacillus licheniformis* | Unknown, isolated 1968 | SEQ ID NO: 22 |
| 7 | *Streptomyces thermocarboxydus* | United Kingdom | SEQ ID NO: 25 |
| 8 | *Bacillus licheniformis* | U.S. | SEQ ID NO: 28 |
| 9 | *Saccharopolyspora gregorii* | Unknown | SEQ ID NO: 31 |

Example 2. Sequence Identity Between the Cloned Endonuclease 1 Ribonuclease Polypeptides The sequence identities between the mature polypeptides identified in this disclosure were determined. The identities of the mature polypeptides used in this analysis are shown in Table 1. A BLOSUM62 sequence identity matrix was calculated using the amino acid sequences of these mature polypeptides and using the Needle utility from the EMBOSS sequence package (www.emboss.org). The matrix was calculated based on "all against all" alignments of one sequence against another. The numbers in Table 2 below (i.e., sequence identities), were calculated as the number of exact matches between two sequences, divided by the total length of the alignment, minus the total length of the gaps in the alignment. The alignments used a gap opening penalty of 10 and a gap extension penalty of 0.50. The identity matrix is shown below in Table 2. The numbers 3, 6, 9, 14, 19, 22, 25, 28 and 31 identify SEQ ID NOS: of this disclosure. The other numbers (i.e., numbers with a value greater than 60) indicate sequence identities between two SEQ ID NOS.

TABLE 2

Sequence identities of mature endonuclease 1 ribonucleotide polypeptides

| SEQ ID NOS: | 3 | 6 | 9 | 14 | 19 | 22 | 25 | 28 | 31 |
|---|---|---|---|---|---|---|---|---|---|
| 3 | 100 | 91.5 | 78.1 | 90.8 | 68.6 | 74.1 | 75.0 | 74.1 | 67.5 |
| 6 | — | 100 | 80.4 | 96.2 | 69.5 | 73.6 | 72.3 | 73.6 | 68.4 |
| 9 | — | — | 100 | 79.0 | 68.6 | 72.1 | 71.1 | 72.1 | 67.5 |
| 14 | — | — | — | 100 | 69.5 | 75.0 | 71.4 | 75.0 | 67.5 |
| 19 | — | — | — | — | 100 | 63.8 | 70.7 | 63.8 | 78.0 |
| 22 | — | — | — | — | — | 100 | 68.8 | 98.4 | 64.8 |
| 25 | — | — | — | — | — | — | 100 | 68.8 | 69.4 |
| 28 | — | — | — | — | — | — | — | 100 | 64.8 |
| 31 | — | — | — | — | — | — | — | — | 100 |

The data from the analysis shows that the amino acid sequences of SEQ ID NOs: 22 and 28 have greater than 98% sequence identity to one another. The polypeptides from both SEQ ID NO: 22 and SEQ ID NO: 28 are from strains of *Bacillus licheniformis*.

The data from the analysis also shows that the amino acid sequences of SEQ ID NOs: 3, 6 and 14 have greater than 90% sequence identity to one another. All these sequences are from a genus of *Bacillus*. SEQ ID NO: 3 is from *Bacillus mojavensis*. SEQ ID NO: 6 is from *Bacillus subtilis*. SEQ ID NO: 14 is from *Bacillus subtilis* subsp. *spizizenii*.

Also determined were sequence identities of SEQ ID NOs: 3 and 6 to the $Mg^{2+}$-activated ribonuclease from *Bacillus subtilis* (Nakamura, A., et al., 1992. Gene cloning and characterization of a novel extracellular ribonuclease of *Bacillus subtilis*. European Journal of Biochemistry 209, 121-127). SEQ ID NO: 3 is 98.6% identical to the $Mg^{2+}$-activated ribonuclease from *Bacillus subtilis*. SEQ ID NO: 6 is 90.3% identical to the $Mg^{2+}$-activated ribonuclease from *Bacillus subtilis*.

The highest sequence identity between any sequence in the SEQ ID NO: 22 and 28 group and any sequence in the SEQ ID NO: 3, 6 and 14 group is 75.0% (between SEQ ID NOs: 14 and 22; also between SEQ ID NOs: 14 and 28).

The data from the analysis also shows that the amino acid sequences of SEQ ID NOs: 6 and 9 have greater than 80% sequence identity to one another.

Example 3. Definition of Endonuclease 1 Clades

The sequences used to construct the phylogenetic tree, as described in Example 1, were analyzed to determine specific amino acid sequences that could be used to identify clades or sub-clusters of polypeptides containing the Pfam PF04231 domain. The goal of this analysis was to attempt to identify motifs that could be used to identify the polypeptides that were grouped into the branch of the phylogenetic tree that contained the $Mg^{2+}$-activated ribonuclease from *Bacillus subtilis* (Nakamura, A., et al., 1992. Gene cloning and characterization of a novel extracellular ribonuclease of *Bacillus subtilis*. European Journal of Biochemistry 209, 121-127), as well as the polypeptides in Table 1 herein.

From this analysis, the inventors identified that a group of the polypeptides containing Pfam PF04231 domains contained the amino acid sequence NREH (SEQ ID NO: 32). These polypeptides are members of the NREH clade (NREH; SEQ ID NO: 32). This clade encompasses polypeptides present in the ENDO1 A, ENDO1 C and ENDO1 D branches of the tree.

The polypeptides containing the NREH (SEQ ID NO: 32) sequence could be separated into further sub-clusters. One sub-cluster contained the amino acid sequence D[AEQ]DP (SEQ ID NO: 33). These polypeptides were said to be members of the DADP clade (D[AEQ]DP; SEQ ID NO: 33). This clade encompasses polypeptides present in the ENDO1 A and ENDO1 C branches of the phylogenetic tree. The DADP clade (D[AEQ]DP; SEQ ID NO: 33) contains the $Mg^{2+}$-activated ribonuclease from *Bacillus subtilis* (Nakamura, A., et al., 1992. Gene cloning and characterization of a novel extracellular ribonuclease of *Bacillus subtilis*. European Journal of Biochemistry 209, 121-127). This sub-cluster also contains a majority of polypeptides containing Pfam PF04231 domains that are from *Bacillus* species.

The polypeptides that were members of the DADP clade (D[AEQ]DP; SEQ ID NO: 33) could be separated into further sub-clusters. One sub-cluster contained the amino acid sequence TDEDP (SEQ ID NO: 34). These polypeptides were said to be members of the TDED clade (TDEDP; SEQ ID NO: 34). This clade encompasses polypeptides present in the ENDO1 A branch of the phylogenetic tree.

Polypeptides that were members of the TDED clade (TDEDP; SEQ ID NO: 34) could be further separated into sub-clusters. Some of these polypeptides contained the amino acid sequence SHG. Some polypeptides in the TDED clade (TDEDP; SEQ ID NO: 34) contained the amino acid sequence NREHVWA (SEQ ID NO: 35).

The $Mg^{2+}$-activated ribonuclease from *Bacillus subtilis* (Nakamura, A., et al., 1992. Gene cloning and characterization of a novel extracellular ribonuclease of *Bacillus subtilis*. European Journal of Biochemistry 209, 121-127), as well as the polypeptides contained in Table 1 herein, belong to the TDED clade (TDEDP; SEQ ID NO: 34), and contain the amino acid sequences TDEDP (SEQ ID NO: 34), NREHVWA (SEQ ID NO: 35), as well as SHG.

Example 4. Expression of Genes Encoding Endonuclease 1 Ribonucleases

The genes identified in Example 1 were expressed to obtain protein. The mature polypeptides indicated in Table 1 were expressed. In addition to the sequences in Table 1, codon-optimized sequences for the gene from *Bacillus pumilus* was synthesized. The codon-optimized gene is shown as SEQ ID NO: 10. The full-length polypeptide encoded by SEQ ID NO: 10 is shown in SEQ ID NO: 11. SEQ ID NO: 11 is the same as SEQ ID NO: 8. A codon optimized gene was also synthesized based on the sequence obtained from *Bacillus subtilis* subsp. *Spizizenii*. This gene is shown as SEQ ID NO: 15 and encodes a full-length polypeptide as shown in SEQ ID NO: 16. SEQ ID NO: 16 is the same as SEQ ID NO: 13.

Expression vectors containing the polypeptide-coding sequences were constructed and used to express the proteins, generally as described in WO/2022/025577. The expression plasmids encoded a *Bacillus clausii* secretion signal, MKKPLGKIVASTALLISVAFSSSIASA (SEQ ID NO: 36), a His-tag, and the endonuclease 1 ribonuclease sequence. Expression of the cloned genes were designed to be controlled by a multiple promoter system, as described in WO1999/043835. The expression construct also contained a gene encoding chloramphenicol acetyltransferase (Diderichsen, B., et al., 1993. A useful cloning vector for *Bacillus subtilis*. Plasmid 30, 312-315).

The expression plasmids were transformed into a *Bacillus subtilis* expression host and transformants containing the sequences that had homologously integrated into the bacterial chromosome were selected by including chloramphenicol in the medium. One transformed clone was selected, grown in liquid medium and the cells harvested. Recombinant proteins were purified using the His-tag, using standard methods.

Example 5. RNase Activity of Polypeptides

In a first set of experiments, RNA substrate was incubated with enzymes, and the reaction mixture was visualized after gel electrophoresis to determine whether the RNA had been digested by the enzymes. Reaction volumes of 100 µl contained 6 g/l of *Torula* yeast RNA (Sigma) and 0.1 ppm enzyme (SEQ ID NO: 3, SEQ ID NO: 6, or control enzyme) in 0.1 M Hepes, pH 8. The reactions were incubated for 2 hours at 37° C., and a portion of each reaction mixture was then mixed with gel loading buffer and analyzed by gel electrophoresis using FlashGel™ RNA cassettes (Lonza), as suggested by the manufacturer. Control enzymes included a T1 RNase from *Stenotrophomonas* (positive control), a guanyl-specific ribonuclease F from *Acremonium* (positive control) and a phosphodiesterase (PDE; negative control). A negative control with no enzyme was also used.

Figure 2:
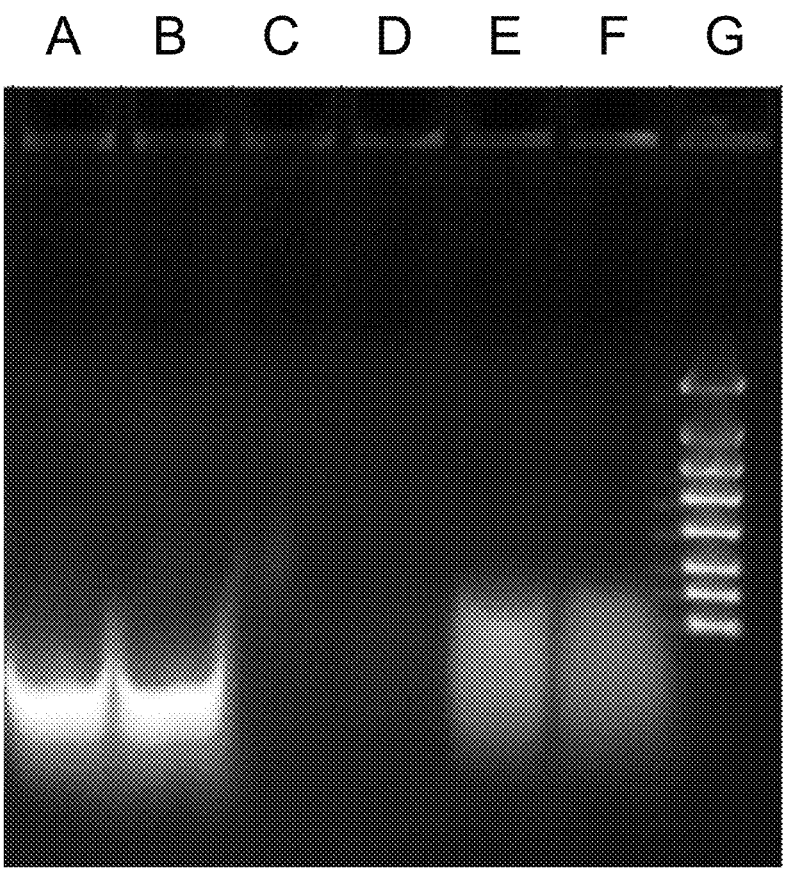
FIG. 2 illustrates results from an example experiment as described in Example 5.

The data from the experiment are shown in FIG. 2. Lane A of the gel in the figure is the no-enzyme control. Lane B is the PDE negative control. Lane C is SEQ ID NO: 6. Lane D is SEQ ID NO: 3. Lane E is T1 RNase positive control. Lane F is the guanyl-specific ribonuclease F positive control. Lane G is DNA molecular weight markers (FlashGel™; Lonza).

These data showed that SEQ ID NO: 3 and SEQ ID NO: 6 have RNase activity in the assay.

In a second set of experiments, the cloned and expressed polypeptides were examined for RNase activity in buffer (100 mM Hepes, pH 8) and in a model detergent (Model B detergent, as described below). In these experiments, RNase activity was determined by fluorescence using a fluorescence-quenched oligonucleotide probe (relative fluorescence units, RFU). This probe emits a signal after nuclease degradation (RNaseAlert™ kit, Integrated DNA Technologies, Inc., Coralville, Iowa, USA). Briefly, RNase was diluted in 0.1 M Hepes, pH 8 to obtain a concentration of 0.1 ppm, or in model detergent B wash liquor (EU, 3.3 g/L), as described below, in water to obtain a concentration of 1 ppm. Five µl of the RNaseAlert™ substrate was added to 95 µl of the RNase sample.

Model detergent B wash liquor (100%) was prepared by dissolving 3.33 g/l of model detergent B in water. Model detergent B contained 7.2% LAS, 6.6% AEO Biosoft N25-7 (NI), 4.2% AEOS (SLES), 6% MPG (mono propylene glycol), 3% ethanol, 3% TEA (triethanolamine), 2.75% cocoa soap, 2.75% soya soap, 2% glycerol, 1.2% sodium hydroxide, 2% sodium citrate, 1% sodium formate, 0.2% DTMPA and 0.2% PCA (Propenoic acid). All percentages are w/w (weight/weight).

A kinetic curve was measured for 10 min at 22° C. using a SpectraMax® microplate reader, Molecular Devices (excitation 490 nm, emission at 520 nm). No activity was detected in controls that contained the RNaseAlert™ fluorescence-quenched oligonucleotide substrate with no enzyme. The data in the tables below were generally reported as the "initial RFU." In other studies, the data may be data reported as total RFU over the full 10 min measurement. The method of reporting within single tables herein was consistent.

Table 3 below shows RNase activity measured in buffer or in model detergent B. Different rows for the same polypeptide represent separate experimental samples.

TABLE 3

RNase activity of polypeptides

| Experiment | Polypeptide | Genus & species of organism | Activity in buffer (RFU) | Activity in detergent (RFU) |
|---|---|---|---|---|
| 1 | SEQ ID NO: 3 | Bacillus mojavensis | 2.85 | 8.00 |
| 2 | SEQ ID NO: 3 | Bacillus mojavensis | 0.62 | 4.00 |
| 3 | SEQ ID NO: 3 | Bacillus mojavensis | 1.04 | 1.99 |
| 4 | SEQ ID NO: 6 | Bacillus subtilis | 2.98 | 8.00 |
| 5 | SEQ ID NO: 6 | Bacillus subtilis | 1.02 | 6.00 |
| 6 | T1 RNase control | Stenotrophomonas | 8.00 | 0.02 |
| 7 | Guanyl-specific RNase F | Acremonium | 8.00 | 8.00 |

These data showed that SEQ ID NO: 3 and SEQ ID NO: 6 have RNase activity in this assay, in both buffer and in the Model detergent B. The data showed that RNase activity was higher in the Model detergent B than in buffer.

Example 6. Removal of RNA from Textiles by Laundering Using RNase

In one set of assays, the endonuclease 1 ribonuclease polypeptides were tested for their ability to remove RNA from soiled laundry. Soiled socks and, separately, soiled pillowcases were used.

For socks, twelve socks from twelve different pairs of socks (one sock per pair) were used (Warwick Equest). From each sock, four 1 cm diameter swatches were cut—two swatches from the sole and two swatches from the heel of the sock. Each sole swatch was paired with a heel swatch from the same sock, and the paired swatches were added together to a well of a 24-deep well plate (24 total wells, each containing a sole and heel swatch from the same sock). Six wells were laundered with a detergent composition containing the polypeptide of SEQ ID NO: 3. Six wells were laundered with a detergent composition containing the polypeptide of SEQ ID NO: 6. Six wells were laundered with a detergent composition containing no polypeptide (negative control). A similar procedure was used for pillowcases.

The laundering was performed as follows. Two mL of model detergent B wash liquor (EU, 3.3 g/L) was added to each well. For each experimental well, RNase polypeptide was also present at 1 ppm. For each control well, no RNase polypeptide was present. Therefore, EU conditions of 3.3 g/L detergent and water with a hardness of 15°dH (Ca:Mg:NaHCO₃ 4:1:1.5) were used. The 24-deep well plates were then incubated at 30° C. with shaking (800 rpm) for 1 hour. Subsequently, the swatches were rinsed in water (hardness 15°dH) and dried.

To extract remaining RNA from the swatches, so the amount of RNA could be determined, 0.8 mL of an RNase-free buffer (0.1% v/v DEPC, 10 mM EDTA, 0.9% NaCl, pH 4.5) was added to each well, and the deep well plates were incubated for 1 hour at room temperature with shaking (800 rpm). Subsequently, 100 μl from each well was added to 100 μl of Quant-IT™ RiboGreen® (Thermofisher) reagent as recommended by the supplier protocol. After 3 min incubation at room temperature, endpoint fluorescence was measured at 22° C. in a SpectraMax® microplate reader (Molecular Devices) using excitation at 500 nm and emission at 525 nm. Fluorescence of the experimental samples (plus RNase) was subtracted from the control samples (no RNase) to determine the percent reduction in relative fluorescence units in the experimental samples as compared to the controls (% RFU reduction). The data are shown in Table 4 below.

TABLE 4

RNA removed from textiles by detergent containing RNases

| RNase | % RFU reduction socks | % RFU reduction pillowcases |
|---|---|---|
| SEQ ID NO: 3 | 8 | 26 |
| SEQ ID NO: 6 | 37 | 18 |

The results showed that the polypeptides having RNase activity reduced the amount of RNA on soiled textiles, when used as part of a detergent composition.

Example 7. Biofilm Washing in Detergent

In this set of assays, the endonuclease 1 ribonuclease polypeptides were tested for their ability to remove RNA from biofilms. To create swatches with biofilms on the surface, a fabric swatch was added to each well of 12-well polystyrene flat-bottom microplates. Bacterial growth medium was then added to each well. Separately, a strain of Kocuria kristinae bacteria was grown in liquid medium, washed and resuspended in sterile buffer. An equal volume of the resuspended bacteria was added to each microplate well. The microplates were then incubated at 37° C. for 72 hours. Non-adherent cells were removed by gentle washing/rinsing the swatches.

Five of the rinsed swatches with Kocuria kristinae biofilm were then added to 50 ml test tubes, and 10 mL of detergent wash solution comprising the following detergent composition in mentioned concentration was added: model detergent A (EU, 3.3 g/L, water hardness 15°dH), was added together with 0.7 g/L soil (Pigmentschmutz, 09V, wfk, Krefeld, Germany) and RNases SEQ ID NO: 3 or SEQ ID NO: 6 at 2 ppm. The RNases had activity in the synthetic oligonucleotide substrate assay described in Example 3.

Model detergent A wash liquor (100%) was prepared by dissolving 3.33 g/l of model detergent A containing 12% LAS, 1.1% AEO Biosoft N25-7 (NI), 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight volume) in water with hardness 15 dH).

Test tubes were placed in a Stuart rotator (Mini LOM) for 1 hour at 30° C. Swatches were rinsed twice with tap water and dried on filter paper overnight. As control, washes with the mentioned detergent and without addition of RNase were made in parallel. Remission (REM) values at 460 nm was measured using a Color Eye (Macbeth Color Eye 7000 reflectance spectrophotometer). The measurements were made without UV in the incident light. Higher values indicate more removal of biofilm.

TABLE 5

Biofilm removed from textiles by detergent containing RNases

| RNase | ΔRem (460 nm) |
|---|---|
| SEQ ID NO: 3 | 6.0 |
| SEQ ID NO: 6 | 4.2 |

The results showed that the polypeptides having RNase activity reduced the amount of biofilm on soiled textiles, when used as part of a detergent composition.

Example 8. RNase Activity of Additional Polypeptides

Additional mature polypeptides were tested for RNase activity. The assays were similar to those described in Example 5, that used the fluorescence-quenched oligonucleotide probe (RNaseAlert™ kit). The experiments tested for RNase activity as follows:
i) in water (hardness 15°dH) using the polypeptides at a concentration 0.1 ppm;
ii) in 100 mM Hepes buffer, pH 8, using the polypeptides at a concentration of 0.1 ppm;
iii) in 100 mM 3-(Cyclohexylamino)-1-propanesulfonic acid (CAPS buffer) using the polypeptides at a concentration of 1.0 ppm;
iv) in Model B detergent, as described in Example 5, using the polypeptides at a concentration of 0.1 ppm;
v) in Model A detergent, as described below and in Example 5, using the polypeptides at a concentration of 0.1 ppm; and
vi) in Model X detergent, as described below and in Example 5, using the polypeptides at a concentration of 1.0 ppm.

Model detergent A wash liquor (100%) was prepared by dissolving 3.33 g/l of model detergent A containing 12% LAS, 1.1% AEO, 7% AEOS (SLES), 6% MPG, 3% ethanol, 3% TEA (triethanolamine), 2.75% cocoa soap, 2.75% soya soap, 2% glycerol, 2% sodium hydroxide, 2% sodium citrate, 1% sodium formiate, 0.2% DTMPA and 0.2% PCA (all percentages are w/w (weight volume) in water with hardness 15 dH.

Model detergent X wash liquor (100%) was prepared by dissolving 1.75 g/l of model detergent X containing 17% LAS, 2.2% AEO, 20% soda ash, 12.3% hydrous sodium silicate, 16% zeolite+PCA and 31% sodium sulfate (all percentages are w/w (weight volume) in water with hardness 15 dH.

Results of the experiments are shown below in Table 6 below.

TABLE 6

RNase activity of polypeptides

| Experiment | Polypeptide | Genus & species of organism | Activity in water (RFU) | Activity in Hepes (RFU) | Activity in CAPS (RFU) | Activity in Model B (RFU) | Activity in Model A (RFU) | Activity in Model X (RFU) |
|---|---|---|---|---|---|---|---|---|
| 1 | SEQ ID NO: 3 | Bacillus mojavensis | 2.99 | 2.85 | 6.00 | 8.00 | 2.45 | 2.66 |
| 2 | SEQ ID NO: 6 | Bacillus subtilis | 2.73 | 2.98 | 6.00 | 8.00 | 3.16 | 2.35 |
| 3 | SEQ ID NO: 9 | Bacillus pumilus | 4.39 | — | — | 0.09 | — | — |
| 4 | SEQ ID NO: 14 | Bacillus subtilis subsp. spizizenii | 2.39 | — | — | 2.45 | — | — |
| 5 | SEQ ID NO: 19 | Saccharopolyspora hirsuta | 0.20 | 0.09 | 0.12 | 0.70 | 0.08 | 0.09 |
| 6 | SEQ ID NO: 22 | Bacillus licheniformis | 0.02 | 0.01 | 0.01 | 0.14 | 0.02 | 0.01 |
| 7 | SEQ ID NO: 25 | Streptomyces thermocarboxydus | 0.06 | 0.03 | 0.05 | 0.73 | 0.08 | 0.07 |
| 8 | SEQ ID NO: 28 | Bacillus licheniformis | 0.02 | 10.02 | 0.02 | 10.22 | 0.02 | 0.01 |
| 9 | SEQ ID NO: 31 | Saccharopolyspora gregorii | 0.02 | 0.01 | 0.03 | 0.07 | 0.01 | 0.02 |

These data showed that SEQ ID NOs: 3, 6, 9 and 14 have RNase activity in these assays.

The invention claimed is:

1. A method for cleaning a textile, comprising contacting the textile with a polypeptide having RNase activity, wherein the polypeptide has at least 92% sequence identity to SEQ ID NO: 3.

2. The method of claim 1, wherein the polypeptide additionally comprises at least one of the amino acid sequences NREH (SEQ ID NO: 32), D[AEQ]DP (SEQ ID NO: 33), TDEDP (SEQ ID NO: 34), SHG and/or NREHVWA (SEQ ID NO: 35).

3. The method of claim 1 wherein the polypeptide has at least 95% sequence identity to SEQ ID NO: 3.

4. The method of claim 1, wherein the polypeptide has at least 97% sequence identity to SEQ ID NO: 3.

5. The method of claim 1, wherein the polypeptide is a variant that has one or more amino acid substitutions, one or more amino acid deletions, one or more amino acid insertions, or any combination thereof, in 1, 2, 3, 4, 5, 6, 7, 8, 9, 10, 11, 12, 13, 14, 15, 16, 17, 18, 19 or 20 positions.

6. The method of claim 1, wherein the polypeptide has an N-terminal, a C-terminal, or an N-terminal and a C-terminal amino acid extension of between 1 and 10 amino acids.

7. A method for laundering a textile, comprising: (a) exposing the textile to a composition comprising a detergent adjunct ingredient and a polypeptide having RNase activity, wherein the polypeptide has at least 92% sequence identity to SEQ ID NO: 3.

8. The method of claim 7, further comprising rinsing the textile.

9. The method of claim 7, wherein the polypeptide additionally comprises at least one of the amino acid sequences NREH (SEQ ID NO: 32), D[AEQ]DP (SEQ ID NO: 33), TDEDP (SEQ ID NO: 34), SHG and/or NREHVWA (SEQ ID NO: 35).

10. The method of claim 7, wherein the polypeptide has at least 95% sequence identity to SEQ ID NO: 3.

11. The method of claim 7, wherein the polypeptide has at least 97% sequence identity to SEQ ID NO: 3.

12. The method of claim 7, wherein the polypeptide is a variant that has one or more amino acid substitutions, one or more amino acid deletions, one or more amino acid insertions, or any combination thereof, in 1, 2, 3, 4, 5, 6, 7, 8, 9, 10, 11, 12, 13, 14, 15, 16, 17, 18, 19 or 20 positions.

13. The method of claim 7, wherein the polypeptide has an N-terminal, a C-terminal, or an N-terminal and a C-terminal amino acid extension of between 1 and 10 amino acids.

* * * * *

UNITED STATES PATENT AND TRADEMARK OFFICE
CERTIFICATE OF CORRECTION

PATENT NO. : 12,146,123 B2
APPLICATION NO. : 17/276317
DATED : November 19, 2024
INVENTOR(S) : Jesper Salomon Page 1 of 1

It is certified that error appears in the above-identified patent and that said Letters Patent is hereby corrected as shown below:

In the Claims

Claim 7 (Column 113, Line 42 – Column 114, Line 22) should read:
7. A method for laundering a textile, comprising: (a) exposing the textile to a composition comprising a detergent adjunct ingredient and a polypeptide having RNase activity, wherein the polypeptide has at least 92% sequence identity to SEQ ID NO: 3; and (b) completing at least one wash cycle.

Signed and Sealed this
Twenty-second Day of April, 2025

Coke Morgan Stewart
*Acting Director of the United States Patent and Trademark Office*

SEQUENCE LISTING

```
<160> NUMBER OF SEQ ID NOS: 36

<210> SEQ ID NO 1
<211> LENGTH: 867
<212> TYPE: DNA
<213> ORGANISM: Bacillus mojavensis
<220> FEATURE:
<221> NAME/KEY: CDS
<222> LOCATION: (1)..(864)
<220> FEATURE:
```

```
<221> NAME/KEY: sig_peptide
<222> LOCATION: (1)..(78)
<220> FEATURE:
<221> NAME/KEY: mat_peptide
<222> LOCATION: (79)..(864)

<400> SEQUENCE: 1
```

| | | | | | | | | | | | | | | | | |
|---|---|---|---|---|---|---|---|---|---|---|---|---|---|---|---|---|
| atg | aca | aca | aaa | gca | agg | ttt | ctg | ccg | ctc | gtc | tgt | gta | tta | ctg | att | 48 |
| Met | Thr | Thr | Lys | Ala | Arg | Phe | Leu | Pro | Leu | Val | Cys | Val | Leu | Leu | Ile | |
| -25 | | | | | -20 | | | | | -15 | | | | | | |
| tcc | gga | tgg | ttt | gcg | ccc | tct | gct | tca | gca | agc | gcg | caa | acc | gga | ttg | 96 |
| Ser | Gly | Trp | Phe | Ala | Pro | Ser | Ala | Ser | Ala | Ser | Ala | Gln | Thr | Gly | Leu | |
| -10 | | | | | -5 | | | | | -1 | 1 | | | | 5 | |
| aac | ctg | aat | gac | cgt | gca | gct | att | tct | ccc | gca | gcc | tcc | gga | ggc | att | 144 |
| Asn | Leu | Asn | Asp | Arg | Ala | Ala | Ile | Ser | Pro | Ala | Ala | Ser | Gly | Gly | Ile | |
| | | | 10 | | | | | 15 | | | | | 20 | | | |
| ctc | tca | ttg | gtc | tct | ccc | gct | gca | cca | tac | acc | gac | aca | gac | acc | tat | 192 |
| Leu | Ser | Leu | Val | Ser | Pro | Ala | Ala | Pro | Tyr | Thr | Asp | Thr | Asp | Thr | Tyr | |
| | | 25 | | | | | 30 | | | | | 35 | | | | |
| tat | gaa | ggt | gct | gaa | gga | aaa | agc | gga | gag | gcg | tta | aaa | agc | gcg | ctg | 240 |
| Tyr | Glu | Gly | Ala | Glu | Gly | Lys | Ser | Gly | Glu | Ala | Leu | Lys | Ser | Ala | Leu | |
| 40 | | | | | 45 | | | | | 50 | | | | | | |
| cac | cgc | atc | atc | agc | gga | cat | acg | atg | ctg | tct | tac | agc | gag | gta | tgg | 288 |
| His | Arg | Ile | Ile | Ser | Gly | His | Thr | Met | Leu | Ser | Tyr | Ser | Glu | Val | Trp | |
| 55 | | | | 60 | | | | | 65 | | | | | 70 | | |
| aac | gcg | ctg | aaa | gaa | acg | gat | gca | gat | ccg | gca | aat | ccg | aat | aac | gtc | 336 |
| Asn | Ala | Leu | Lys | Glu | Thr | Asp | Ala | Asp | Pro | Ala | Asn | Pro | Asn | Asn | Val | |
| | | | 75 | | | | | 80 | | | | | 85 | | | |
| atc | ctg | ctc | tat | acg | aat | gaa | tcg | cgt | tcg | aaa | aac | cta | aac | ggc | ggc | 384 |
| Ile | Leu | Leu | Tyr | Thr | Asn | Glu | Ser | Arg | Ser | Lys | Asn | Leu | Asn | Gly | Gly | |
| | | 90 | | | | | 95 | | | | | 100 | | | | |
| aat | gtc | ggg | gac | tgg | aac | cgg | gag | cat | gtc | tgg | gcg | aaa | tcc | cat | ggc | 432 |
| Asn | Val | Gly | Asp | Trp | Asn | Arg | Glu | His | Val | Trp | Ala | Lys | Ser | His | Gly | |
| | 105 | | | | | 110 | | | | | 115 | | | | | |
| gat | ttt | ggt | aca | agc | aaa | ggg | ccc | ggc | act | gac | att | cat | cac | ttg | cgt | 480 |
| Asp | Phe | Gly | Thr | Ser | Lys | Gly | Pro | Gly | Thr | Asp | Ile | His | His | Leu | Arg | |
| 120 | | | | | 125 | | | | | 130 | | | | | | |
| cca | gca | gac | gtc | caa | gta | aac | agc | gcc | aga | ggc | aac | ttg | gac | ttt | gac | 528 |
| Pro | Ala | Asp | Val | Gln | Val | Asn | Ser | Ala | Arg | Gly | Asn | Leu | Asp | Phe | Asp | |
| 135 | | | | 140 | | | | | 145 | | | | | 150 | | |
| aac | ggc | ggc | aac | gag | tat | gcg | aaa | gcg | cct | gga | aat | tac | tat | gat | gga | 576 |
| Asn | Gly | Gly | Asn | Glu | Tyr | Ala | Lys | Ala | Pro | Gly | Asn | Tyr | Tyr | Asp | Gly | |
| | | | 155 | | | | | 160 | | | | | 165 | | | |
| gat | tca | tgg | gag | ccc | cgc | gat | gat | gtg | aaa | ggc | gat | gtc | gcc | cgc | atg | 624 |
| Asp | Ser | Trp | Glu | Pro | Arg | Asp | Asp | Val | Lys | Gly | Asp | Val | Ala | Arg | Met | |
| | | 170 | | | | | 175 | | | | | 180 | | | | |
| ctg | ttt | tac | atg | gct | gtc | cgt | tat | gaa | gga | gat | gac | ggc | tac | cct | gac | 672 |
| Leu | Phe | Tyr | Met | Ala | Val | Arg | Tyr | Glu | Gly | Asp | Asp | Gly | Tyr | Pro | Asp | |
| | 185 | | | | | 190 | | | | | 195 | | | | | |
| ctt | gag | ctc | aat | gat | aaa | aca | gga | aac | ggc | tct | gct | cct | tat | cac | gga | 720 |
| Leu | Glu | Leu | Asn | Asp | Lys | Thr | Gly | Asn | Gly | Ser | Ala | Pro | Tyr | His | Gly | |
| 200 | | | | | 205 | | | | | 210 | | | | | | |
| aaa | caa | tcc | gcc | ttg | ctt | gaa | tgg | aat | agg | cag | gac | cct | gtt | gat | gcc | 768 |
| Lys | Gln | Ser | Ala | Leu | Leu | Glu | Trp | Asn | Arg | Gln | Asp | Pro | Val | Asp | Ala | |
| 215 | | | | 220 | | | | | 225 | | | | | 230 | | |
| cgc | gaa | aga | aaa | aga | aat | gaa | atc | att | tat | gaa | aaa | tat | cag | cac | aac | 816 |
| Arg | Glu | Arg | Lys | Arg | Asn | Glu | Ile | Ile | Tyr | Glu | Lys | Tyr | Gln | His | Asn | |
| | | | 235 | | | | | 240 | | | | | 245 | | | |
| cga | aat | cca | ttt | atc | gat | cac | cct | gaa | tgg | gca | gac | gac | att | tgg | ccg | 864 |
| Arg | Asn | Pro | Phe | Ile | Asp | His | Pro | Glu | Trp | Ala | Asp | Asp | Ile | Trp | Pro | |
| | | 250 | | | | | 255 | | | | | 260 | | | | |

```
taa                                                                   867
```

<210> SEQ ID NO 2
<211> LENGTH: 288
<212> TYPE: PRT
<213> ORGANISM: Bacillus mojavensis

<400> SEQUENCE: 2

```
Met Thr Thr Lys Ala Arg Phe Leu Pro Leu Val Cys Val Leu Leu Ile
    -25             -20                 -15

Ser Gly Trp Phe Ala Pro Ser Ala Ser Ala Gln Thr Gly Leu
-10              -5              -1  1               5

Asn Leu Asn Asp Arg Ala Ala Ile Ser Pro Ala Ala Ser Gly Gly Ile
            10                  15                  20

Leu Ser Leu Val Ser Pro Ala Ala Pro Tyr Thr Asp Thr Asp Thr Tyr
            25                  30                  35

Tyr Glu Gly Ala Glu Gly Lys Ser Gly Glu Ala Leu Lys Ser Ala Leu
            40                  45                  50

His Arg Ile Ile Ser Gly His Thr Met Leu Ser Tyr Ser Glu Val Trp
55                  60                  65                  70

Asn Ala Leu Lys Glu Thr Asp Ala Asp Pro Ala Asn Pro Asn Asn Val
                75                  80                  85

Ile Leu Leu Tyr Thr Asn Glu Ser Arg Ser Lys Asn Leu Asn Gly Gly
                90                  95                  100

Asn Val Gly Asp Trp Asn Arg Glu His Val Trp Ala Lys Ser His Gly
            105                 110                 115

Asp Phe Gly Thr Ser Lys Gly Pro Gly Thr Asp Ile His His Leu Arg
            120                 125                 130

Pro Ala Asp Val Gln Val Asn Ser Ala Arg Gly Asn Leu Asp Phe Asp
135                 140                 145                 150

Asn Gly Gly Asn Glu Tyr Ala Lys Ala Pro Gly Asn Tyr Tyr Asp Gly
                155                 160                 165

Asp Ser Trp Glu Pro Arg Asp Asp Val Lys Gly Asp Val Ala Arg Met
            170                 175                 180

Leu Phe Tyr Met Ala Val Arg Tyr Glu Gly Asp Asp Gly Tyr Pro Asp
            185                 190                 195

Leu Glu Leu Asn Asp Lys Thr Gly Asn Gly Ser Ala Pro Tyr His Gly
200                 205                 210

Lys Gln Ser Ala Leu Leu Glu Trp Asn Arg Gln Asp Pro Val Asp Ala
215                 220                 225                 230

Arg Glu Arg Lys Arg Asn Glu Ile Ile Tyr Glu Lys Tyr Gln His Asn
                235                 240                 245

Arg Asn Pro Phe Ile Asp His Pro Glu Trp Ala Asp Asp Ile Trp Pro
            250                 255                 260
```

<210> SEQ ID NO 3
<211> LENGTH: 262
<212> TYPE: PRT
<213> ORGANISM: Bacillus mojavensis

<400> SEQUENCE: 3

```
Ser Ala Gln Thr Gly Leu Asn Leu Asn Asp Arg Ala Ala Ile Ser Pro
1               5                   10                  15

Ala Ala Ser Gly Gly Ile Leu Ser Leu Val Ser Pro Ala Ala Pro Tyr
            20                  25                  30
```

```
Thr Asp Thr Asp Thr Tyr Tyr Glu Gly Ala Glu Gly Lys Ser Gly Glu
         35                  40                  45
Ala Leu Lys Ser Ala Leu His Arg Ile Ile Ser Gly His Thr Met Leu
 50                  55                  60
Ser Tyr Ser Glu Val Trp Asn Ala Leu Lys Glu Thr Asp Ala Asp Pro
 65                  70                  75                  80
Ala Asn Pro Asn Asn Val Ile Leu Leu Tyr Thr Asn Glu Ser Arg Ser
                 85                  90                  95
Lys Asn Leu Asn Gly Gly Asn Val Gly Asp Trp Asn Arg Glu His Val
                100                 105                 110
Trp Ala Lys Ser His Gly Asp Phe Gly Thr Ser Lys Gly Pro Gly Thr
             115                 120                 125
Asp Ile His His Leu Arg Pro Ala Asp Val Gln Val Asn Ser Ala Arg
         130                 135                 140
Gly Asn Leu Asp Phe Asp Asn Gly Gly Asn Glu Tyr Ala Lys Ala Pro
145                 150                 155                 160
Gly Asn Tyr Tyr Asp Gly Asp Ser Trp Glu Pro Arg Asp Asp Val Lys
                165                 170                 175
Gly Asp Val Ala Arg Met Leu Phe Tyr Met Ala Val Arg Tyr Glu Gly
            180                 185                 190
Asp Asp Gly Tyr Pro Asp Leu Glu Leu Asn Asp Lys Thr Gly Asn Gly
        195                 200                 205
Ser Ala Pro Tyr His Gly Lys Gln Ser Ala Leu Leu Glu Trp Asn Arg
    210                 215                 220
Gln Asp Pro Val Asp Ala Arg Glu Arg Lys Arg Asn Glu Ile Ile Tyr
225                 230                 235                 240
Glu Lys Tyr Gln His Asn Arg Asn Pro Phe Ile Asp His Pro Glu Trp
                245                 250                 255
Ala Asp Asp Ile Trp Pro
                260

<210> SEQ ID NO 4
<211> LENGTH: 867
<212> TYPE: DNA
<213> ORGANISM: Bacillus subtilis
<220> FEATURE:
<221> NAME/KEY: CDS
<222> LOCATION: (1)..(864)
<220> FEATURE:
<221> NAME/KEY: sig_peptide
<222> LOCATION: (1)..(84)
<220> FEATURE:
<221> NAME/KEY: mat_peptide
<222> LOCATION: (85)..(864)

<400> SEQUENCE: 4 atg aca aaa aaa gca tgg ttt ctg ccg ctc gtc tgt gta tta ctg att      48
Met Thr Lys Lys Ala Trp Phe Leu Pro Leu Val Cys Val Leu Leu Ile
         -25                 -20                 -15 tcc gga tgg ctt gcg ccg gca gct tca gca agc gcg caa acc gaa tta      96
Ser Gly Trp Leu Ala Pro Ala Ala Ser Ala Ser Ala Gln Thr Glu Leu
        -10                  -5                  -1  1 agc ctt aat gac cga ttg gct tct tcc cct tca gaa aca ggg agc ctt     144
Ser Leu Asn Asp Arg Leu Ala Ser Ser Pro Ser Glu Thr Gly Ser Leu
 5                   10                  15                  20 ctc tca tta gcc gcc ccc gct gca ccc tac gct gac aca gat acc tat     192
Leu Ser Leu Ala Ala Pro Ala Ala Pro Tyr Ala Asp Thr Asp Thr Tyr
             25                  30                  35 tat gaa ggg gct gaa gga aaa act gga gaa tcg cta aaa agc acc ctg     240
```

-continued

```
            Tyr Glu Gly Ala Glu Gly Lys Thr Gly Glu Ser Leu Lys Ser Thr Leu
                         40                  45                  50 cac cgc atc atc agc gga cac acg atg ctg tcc tac agc gaa gta tgg         288
His Arg Ile Ile Ser Gly His Thr Met Leu Ser Tyr Ser Glu Val Trp
             55                  60                  65 aac gcg ctg aaa gaa acc gat gaa gat ccg gca aac cct aat aac gtc         336
Asn Ala Leu Lys Glu Thr Asp Glu Asp Pro Ala Asn Pro Asn Asn Val
 70                  75                  80 atc ctg ctc tat acg aat gaa tcg cgg tcg aaa aac ctg aac ggc ggc         384
Ile Leu Leu Tyr Thr Asn Glu Ser Arg Ser Lys Asn Leu Asn Gly Gly
 85                  90                  95                 100 aat gtc ggc gat tgg aac cgc gag cat gtc tgg gcg aaa tcc cat ggc         432
Asn Val Gly Asp Trp Asn Arg Glu His Val Trp Ala Lys Ser His Gly
                105                 110                 115 gat ttt ggt acg agc aag gga cct ggt act gat att cat cat ttg cgc         480
Asp Phe Gly Thr Ser Lys Gly Pro Gly Thr Asp Ile His His Leu Arg
            120                 125                 130 cca gcc gat gtt caa gtt aac agc gcc aga gga aat atg gat ttt gac         528
Pro Ala Asp Val Gln Val Asn Ser Ala Arg Gly Asn Met Asp Phe Asp
        135                 140                 145 aat ggc ggc act gaa tat gcg aag gca ccc gga aat tat tat gac ggc         576
Asn Gly Gly Thr Glu Tyr Ala Lys Ala Pro Gly Asn Tyr Tyr Asp Gly
150                 155                 160 gat tca tgg gag ccc cgc gat gat gtg aaa ggc gat gtt gcc cgc atg         624
Asp Ser Trp Glu Pro Arg Asp Asp Val Lys Gly Asp Val Ala Arg Met
165                 170                 175                 180 ctg ttt tac atg gct gtc cgt tac gag ggt gat gac ggc tat cct gat         672
Leu Phe Tyr Met Ala Val Arg Tyr Glu Gly Asp Asp Gly Tyr Pro Asp
                185                 190                 195 ctt gag ctt aat gat aag aca ggc aac ggc tca gct cct tat cat ggc         720
Leu Glu Leu Asn Asp Lys Thr Gly Asn Gly Ser Ala Pro Tyr His Gly
            200                 205                 210 aaa caa tct gtc ctg ctc gaa tgg aat aag cag gat ccg gtt gac gac         768
Lys Gln Ser Val Leu Leu Glu Trp Asn Lys Gln Asp Pro Val Asp Asp
        215                 220                 225 cgc gag cgg aaa aga aat gaa atc att tat gaa aaa tat cag cac aac         816
Arg Glu Arg Lys Arg Asn Glu Ile Ile Tyr Glu Lys Tyr Gln His Asn
230                 235                 240 cgc aat cca ttt atc gac cac cct gaa tgg gcg gat gag att tgg ccg         864
Arg Asn Pro Phe Ile Asp His Pro Glu Trp Ala Asp Glu Ile Trp Pro
245                 250                 255                 260 taa                                                                     867
```

<210> SEQ ID NO 5
<211> LENGTH: 288
<212> TYPE: PRT
<213> ORGANISM: Bacillus subtilis

<400> SEQUENCE: 5

```
Met Thr Lys Lys Ala Trp Phe Leu Pro Leu Val Cys Val Leu Leu Ile
            -25                 -20                 -15

Ser Gly Trp Leu Ala Pro Ala Ala Ser Ala Gln Thr Glu Leu
        -10                  -5              -1  1

Ser Leu Asn Asp Arg Leu Ala Ser Pro Ser Glu Thr Gly Ser Leu
 5                  10                  15                  20

Leu Ser Leu Ala Ala Pro Ala Pro Tyr Ala Asp Thr Asp Thr Tyr
                25                  30                  35

Tyr Glu Gly Ala Glu Gly Lys Thr Gly Glu Ser Leu Lys Ser Thr Leu
            40                  45                  50
```

-continued

```
His Arg Ile Ile Ser Gly His Thr Met Leu Ser Tyr Ser Glu Val Trp
        55                  60                  65

Asn Ala Leu Lys Glu Thr Asp Glu Pro Ala Asn Pro Asn Asn Val
    70                  75                  80

Ile Leu Leu Tyr Thr Asn Glu Ser Arg Ser Lys Asn Leu Asn Gly Gly
 85                  90                  95                 100

Asn Val Gly Asp Trp Asn Arg Glu His Val Trp Ala Lys Ser His Gly
                105                 110                 115

Asp Phe Gly Thr Ser Lys Gly Pro Gly Thr Asp Ile His His Leu Arg
            120                 125                 130

Pro Ala Asp Val Gln Val Asn Ser Ala Arg Gly Asn Met Asp Phe Asp
            135                 140                 145

Asn Gly Gly Thr Glu Tyr Ala Lys Ala Pro Gly Asn Tyr Tyr Asp Gly
            150                 155                 160

Asp Ser Trp Glu Pro Arg Asp Asp Val Lys Gly Asp Val Ala Arg Met
165                 170                 175                 180

Leu Phe Tyr Met Ala Val Arg Tyr Glu Gly Asp Asp Gly Tyr Pro Asp
                185                 190                 195

Leu Glu Leu Asn Asp Lys Thr Gly Asn Gly Ser Ala Pro Tyr His Gly
            200                 205                 210

Lys Gln Ser Val Leu Leu Glu Trp Asn Lys Gln Asp Pro Val Asp Asp
            215                 220                 225

Arg Glu Arg Lys Arg Asn Glu Ile Ile Tyr Glu Lys Tyr Gln His Asn
            230                 235                 240

Arg Asn Pro Phe Ile Asp His Pro Glu Trp Ala Asp Glu Ile Trp Pro
245                 250                 255                 260

<210> SEQ ID NO 6
<211> LENGTH: 260
<212> TYPE: PRT
<213> ORGANISM: Bacillus subtilis

<400> SEQUENCE: 6

Gln Thr Glu Leu Ser Leu Asn Asp Arg Leu Ala Ser Ser Pro Ser Glu
 1               5                  10                  15

Thr Gly Ser Leu Leu Ser Leu Ala Ala Pro Ala Ala Pro Tyr Ala Asp
                20                  25                  30

Thr Asp Thr Tyr Tyr Glu Gly Ala Glu Gly Lys Thr Gly Glu Ser Leu
            35                  40                  45

Lys Ser Thr Leu His Arg Ile Ile Ser Gly His Thr Met Leu Ser Tyr
 50                  55                  60

Ser Glu Val Trp Asn Ala Leu Lys Glu Thr Asp Glu Asp Pro Ala Asn
 65                  70                  75                  80

Pro Asn Asn Val Ile Leu Leu Tyr Thr Asn Glu Ser Arg Ser Lys Asn
                85                  90                  95

Leu Asn Gly Gly Asn Val Gly Asp Trp Asn Arg Glu His Val Trp Ala
            100                 105                 110

Lys Ser His Gly Asp Phe Gly Thr Ser Lys Gly Pro Gly Thr Asp Ile
        115                 120                 125

His His Leu Arg Pro Ala Asp Val Gln Val Asn Ser Ala Arg Gly Asn
    130                 135                 140

Met Asp Phe Asp Asn Gly Gly Thr Glu Tyr Ala Lys Ala Pro Gly Asn
145                 150                 155                 160

Tyr Tyr Asp Gly Asp Ser Trp Glu Pro Arg Asp Asp Val Lys Gly Asp
```

```
                    165                 170                 175
Val Ala Arg Met Leu Phe Tyr Met Ala Val Arg Tyr Glu Gly Asp Asp
                180                 185                 190

Gly Tyr Pro Asp Leu Glu Leu Asn Asp Lys Thr Gly Asn Gly Ser Ala
            195                 200                 205

Pro Tyr His Gly Lys Gln Ser Val Leu Leu Glu Trp Asn Lys Gln Asp
        210                 215                 220

Pro Val Asp Asp Arg Glu Arg Lys Arg Asn Glu Ile Ile Tyr Glu Lys
225                 230                 235                 240

Tyr Gln His Asn Arg Asn Pro Phe Ile Asp His Pro Glu Trp Ala Asp
                245                 250                 255

Glu Ile Trp Pro
            260

<210> SEQ ID NO 7
<211> LENGTH: 867
<212> TYPE: DNA
<213> ORGANISM: Bacillus pumilus
<220> FEATURE:
<221> NAME/KEY: CDS
<222> LOCATION: (1)..(864)
<220> FEATURE:
<221> NAME/KEY: sig_peptide
<222> LOCATION: (1)..(78)
<220> FEATURE:
<221> NAME/KEY: mat_peptide
<222> LOCATION: (79)..(864)

<400> SEQUENCE: 7 atg aca aaa aaa ctt tgg ttt ctg ccg att gtc tgc ctg tat ttc att      48
Met Thr Lys Lys Leu Trp Phe Leu Pro Ile Val Cys Leu Tyr Phe Ile
    -25                 -20                 -15 ttt gga tgg gcc gcg ccg tca gcc tct gcg ggc gcg ccg gct gcc acg      96
Phe Gly Trp Ala Ala Pro Ser Ala Ser Ala Gly Ala Pro Ala Ala Thr
-10                  -5              -1  1               5 aat ctg tac agc cgg cgg gcg gtt tca act gcc ggc acc ttt ttt ccg     144
Asn Leu Tyr Ser Arg Arg Ala Val Ser Thr Ala Gly Thr Phe Phe Pro
                10                  15                  20 caa acc gcc tca tcg gtc atc act ccg tct gcg gac acg gac acg tat     192
Gln Thr Ala Ser Ser Val Ile Thr Pro Ser Ala Asp Thr Asp Thr Tyr
        25                  30                  35 tac aaa gaa gct tcc gga aaa agc ggg aca tcc tta aaa agc gct ctg     240
Tyr Lys Glu Ala Ser Gly Lys Ser Gly Thr Ser Leu Lys Ser Ala Leu
    40                  45                  50 cac cgc atc atc agc ggg aat aca aag ctg tct tac agc caa gta tgg     288
His Arg Ile Ile Ser Gly Asn Thr Lys Leu Ser Tyr Ser Gln Val Trp
55                  60                  65                  70 gat gcg ttg aag gaa act gat gaa gat ccg gca aat ccg aac aat gtc     336
Asp Ala Leu Lys Glu Thr Asp Glu Asp Pro Ala Asn Pro Asn Asn Val
                75                  80                  85 atc ttg ctc tat act cag gaa tca cgg gca aaa agt aaa aac ggc gga     384
Ile Leu Leu Tyr Thr Gln Glu Ser Arg Ala Lys Ser Lys Asn Gly Gly
                    90                  95                 100 agc gtc ggg gac tgg aac cgt gaa cat gtg tgg gcc aag tca cac gga     432
Ser Val Gly Asp Trp Asn Arg Glu His Val Trp Ala Lys Ser His Gly
                105                 110                 115 aac ttc ggc aca tct gcc ggc ccc ggc act gac att cat cat ctg cgc     480
Asn Phe Gly Thr Ser Ala Gly Pro Gly Thr Asp Ile His His Leu Arg
            120                 125                 130 ccg gca gac gtt cag gtg aac cgc gcc aga ggt aac atg gat ttt gat     528
Pro Ala Asp Val Gln Val Asn Arg Ala Arg Gly Asn Met Asp Phe Asp
```

```
                  135               140               145                150
aac ggc ggc tca gaa tac ccg aaa gcg ccg ggc aac tat tac gac ggt         576
Asn Gly Gly Ser Glu Tyr Pro Lys Ala Pro Gly Asn Tyr Tyr Asp Gly
                155               160               165 gat tcg tgg gag ccg cgc gat gag gtc aaa gga gac gtc gcg cgc atg         624
Asp Ser Trp Glu Pro Arg Asp Glu Val Lys Gly Asp Val Ala Arg Met
            170               175               180 ctg ttt tac atg gcg gtg cgt tat gaa gga gac gac ggg tac cct gac         672
Leu Phe Tyr Met Ala Val Arg Tyr Glu Gly Asp Asp Gly Tyr Pro Asp
        185               190               195 ctt gag ctg aat gat aaa aca gga aac ggt tcg gct ccc tac atg gga         720
Leu Glu Leu Asn Asp Lys Thr Gly Asn Gly Ser Ala Pro Tyr Met Gly
    200               205               210 aaa ctg tcc gtt ttg ctc aaa tgg aat aaa cag gac ccc gtc gac agt         768
Lys Leu Ser Val Leu Leu Lys Trp Asn Lys Gln Asp Pro Val Asp Ser
215               220               225               230 aag gaa aaa cgg cgg aac gaa ctc att tac gaa gac tat cag cat aac         816
Lys Glu Lys Arg Arg Asn Glu Leu Ile Tyr Glu Asp Tyr Gln His Asn
                235               240               245 cgc aat ccg ttt atc gac cac ccg gaa tgg gcg gat gaa atc tgg aaa         864
Arg Asn Pro Phe Ile Asp His Pro Glu Trp Ala Asp Glu Ile Trp Lys
            250               255               260 tag                                                                     867

<210> SEQ ID NO 8
<211> LENGTH: 288
<212> TYPE: PRT
<213> ORGANISM: Bacillus pumilus

<400> SEQUENCE: 8

Met Thr Lys Lys Leu Trp Phe Leu Pro Ile Val Cys Leu Tyr Phe Ile
    -25               -20               -15

Phe Gly Trp Ala Ala Pro Ser Ala Ser Ala Gly Ala Pro Ala Ala Thr
-10                -5                -1  1                 5

Asn Leu Tyr Ser Arg Arg Ala Val Ser Thr Ala Gly Thr Phe Phe Pro
                10                15                 20

Gln Thr Ala Ser Ser Val Ile Thr Pro Ser Ala Asp Thr Asp Thr Tyr
            25                30                35

Tyr Lys Glu Ala Ser Gly Lys Ser Gly Thr Ser Leu Lys Ser Ala Leu
        40                45                50

His Arg Ile Ile Ser Gly Asn Thr Lys Leu Ser Tyr Ser Gln Val Trp
55                60                65                70

Asp Ala Leu Lys Glu Thr Asp Glu Asp Pro Ala Asn Pro Asn Asn Val
                75                80                85

Ile Leu Leu Tyr Thr Gln Glu Ser Arg Ala Lys Ser Lys Asn Gly Gly
            90                95                100

Ser Val Gly Asp Trp Asn Arg Glu His Val Trp Ala Lys Ser His Gly
        105               110               115

Asn Phe Gly Thr Ser Ala Gly Pro Gly Thr Asp Ile His His Leu Arg
    120               125               130

Pro Ala Asp Val Gln Val Asn Arg Ala Arg Gly Asn Met Asp Phe Asp
135               140               145               150

Asn Gly Gly Ser Glu Tyr Pro Lys Ala Pro Gly Asn Tyr Tyr Asp Gly
                155               160               165

Asp Ser Trp Glu Pro Arg Asp Glu Val Lys Gly Asp Val Ala Arg Met
            170               175               180
```

Leu Phe Tyr Met Ala Val Arg Tyr Glu Gly Asp Asp Gly Tyr Pro Asp
            185                 190                 195

Leu Glu Leu Asn Asp Lys Thr Gly Asn Gly Ser Ala Pro Tyr Met Gly
    200                 205                 210

Lys Leu Ser Val Leu Leu Lys Trp Asn Lys Gln Asp Pro Val Asp Ser
215                 220                 225                 230

Lys Glu Lys Arg Arg Asn Glu Leu Ile Tyr Glu Asp Tyr Gln His Asn
                235                 240                 245

Arg Asn Pro Phe Ile Asp His Pro Glu Trp Ala Asp Glu Ile Trp Lys
            250                 255                 260

<210> SEQ ID NO 9
<211> LENGTH: 262
<212> TYPE: PRT
<213> ORGANISM: Bacillus pumilus

<400> SEQUENCE: 9

Gly Ala Pro Ala Ala Thr Asn Leu Tyr Ser Arg Arg Ala Val Ser Thr
1               5                   10                  15

Ala Gly Thr Phe Phe Pro Gln Thr Ala Ser Ser Val Ile Thr Pro Ser
            20                  25                  30

Ala Asp Thr Asp Thr Tyr Tyr Lys Glu Ala Ser Gly Lys Ser Gly Thr
        35                  40                  45

Ser Leu Lys Ser Ala Leu His Arg Ile Ile Ser Gly Asn Thr Lys Leu
    50                  55                  60

Ser Tyr Ser Gln Val Trp Asp Ala Leu Lys Glu Thr Asp Glu Asp Pro
65                  70                  75                  80

Ala Asn Pro Asn Asn Val Ile Leu Leu Tyr Thr Gln Glu Ser Arg Ala
                85                  90                  95

Lys Ser Lys Asn Gly Gly Ser Val Gly Asp Trp Asn Arg Glu His Val
            100                 105                 110

Trp Ala Lys Ser His Gly Asn Phe Gly Thr Ser Ala Gly Pro Gly Thr
        115                 120                 125

Asp Ile His His Leu Arg Pro Ala Asp Val Gln Val Asn Arg Ala Arg
    130                 135                 140

Gly Asn Met Asp Phe Asp Asn Gly Gly Ser Glu Tyr Pro Lys Ala Pro
145                 150                 155                 160

Gly Asn Tyr Tyr Asp Gly Asp Ser Trp Glu Pro Arg Asp Glu Val Lys
                165                 170                 175

Gly Asp Val Ala Arg Met Leu Phe Tyr Met Ala Val Arg Tyr Glu Gly
            180                 185                 190

Asp Asp Gly Tyr Pro Asp Leu Glu Leu Asn Asp Lys Thr Gly Asn Gly
        195                 200                 205

Ser Ala Pro Tyr Met Gly Lys Leu Ser Val Leu Leu Lys Trp Asn Lys
    210                 215                 220

Gln Asp Pro Val Asp Ser Lys Glu Lys Arg Arg Asn Glu Leu Ile Tyr
225                 230                 235                 240

Glu Asp Tyr Gln His Asn Arg Asn Pro Phe Ile Asp His Pro Glu Trp
                245                 250                 255

Ala Asp Glu Ile Trp Lys
            260

<210> SEQ ID NO 10
<211> LENGTH: 867
<212> TYPE: DNA
<213> ORGANISM: Artificial Sequence

```
<220> FEATURE:
<223> OTHER INFORMATION: Codon optimized synthetic sequence
<220> FEATURE:
<221> NAME/KEY: CDS
<222> LOCATION: (1)..(864)
<220> FEATURE:
<221> NAME/KEY: sig_peptide
<222> LOCATION: (1)..(78)
<220> FEATURE:
<221> NAME/KEY: mat_peptide
<222> LOCATION: (79)..(864)

<400> SEQUENCE: 10
```

| | | | | | | | | | | | | | | | |
|---|---|---|---|---|---|---|---|---|---|---|---|---|---|---|---|
| atg | acg | aag | aaa | ctt | tgg | ttc | ctt | cct | atc | gtt | tgc | ctt | tac | ttt | atc | 48 |
| Met | Thr | Lys | Lys | Leu | Trp | Phe | Leu | Pro | Ile | Val | Cys | Leu | Tyr | Phe | Ile | |
| | -25 | | | | -20 | | | | | -15 | | | | | | |

| ttt | ggc | tgg | gct | gct | cct | tct | gct | tca | gct | ggc | gct | cct | gca | gcg | act | 96 |
| Phe | Gly | Trp | Ala | Ala | Pro | Ser | Ala | Ser | Ala | Gly | Ala | Pro | Ala | Ala | Thr | |
| -10 | | | | | -5 | | | | -1 | 1 | | | | | 5 | |

| aac | ctt | tac | tct | cgt | cgt | gcg | gtt | tca | aca | gca | ggt | acg | ttt | ttc | cct | 144 |
| Asn | Leu | Tyr | Ser | Arg | Arg | Ala | Val | Ser | Thr | Ala | Gly | Thr | Phe | Phe | Pro | |
| | | | 10 | | | | | 15 | | | | | 20 | | | |

| caa | aca | gca | tct | tca | gtt | atc | act | cct | tca | gct | gac | act | gac | acg | tac | 192 |
| Gln | Thr | Ala | Ser | Ser | Val | Ile | Thr | Pro | Ser | Ala | Asp | Thr | Asp | Thr | Tyr | |
| | | 25 | | | | | 30 | | | | | 35 | | | | |

| tat | aag | gag | gct | tct | ggt | aaa | tca | ggc | act | tca | ctt | aag | tca | gca | ctt | 240 |
| Tyr | Lys | Glu | Ala | Ser | Gly | Lys | Ser | Gly | Thr | Ser | Leu | Lys | Ser | Ala | Leu | |
| 40 | | | | | | 45 | | | | | 50 | | | | | |

| cat | cgc | atc | atc | tca | ggc | aac | act | aaa | ctt | tca | tac | tca | cag | gtt | tgg | 288 |
| His | Arg | Ile | Ile | Ser | Gly | Asn | Thr | Lys | Leu | Ser | Tyr | Ser | Gln | Val | Trp | |
| 55 | | | | | 60 | | | | | 65 | | | | | 70 | |

| gac | gca | ctt | aaa | gag | act | gac | gag | gac | cct | gca | aac | cct | aac | aac | gta | 336 |
| Asp | Ala | Leu | Lys | Glu | Thr | Asp | Glu | Asp | Pro | Ala | Asn | Pro | Asn | Asn | Val | |
| | | | 75 | | | | | 80 | | | | | 85 | | | |

| atc | ctt | ctt | tac | act | caa | gag | tca | cgc | gca | aaa | agc | aag | aat | ggt | ggc | 384 |
| Ile | Leu | Leu | Tyr | Thr | Gln | Glu | Ser | Arg | Ala | Lys | Ser | Lys | Asn | Gly | Gly | |
| | | | | 90 | | | | | 95 | | | | | 100 | | |

| tca | gtt | gga | gac | tgg | aac | cgc | gag | cat | gta | tgg | gcc | aaa | tca | cat | ggc | 432 |
| Ser | Val | Gly | Asp | Trp | Asn | Arg | Glu | His | Val | Trp | Ala | Lys | Ser | His | Gly | |
| | | 105 | | | | | 110 | | | | | 115 | | | | |

| aac | ttc | ggc | act | agc | gca | ggc | cct | ggc | aca | gac | atc | cat | cac | ctt | cgc | 480 |
| Asn | Phe | Gly | Thr | Ser | Ala | Gly | Pro | Gly | Thr | Asp | Ile | His | His | Leu | Arg | |
| | 120 | | | | | | 125 | | | | | 130 | | | | |

| cct | gct | gac | gtt | caa | gta | aat | cgc | gct | cgt | ggc | aac | atg | gac | ttc | gac | 528 |
| Pro | Ala | Asp | Val | Gln | Val | Asn | Arg | Ala | Arg | Gly | Asn | Met | Asp | Phe | Asp | |
| 135 | | | | 140 | | | | | 145 | | | | | 150 | | |

| aat | ggt | ggc | tca | gag | tac | cct | aaa | gct | cct | ggt | aac | tac | tat | gac | ggc | 576 |
| Asn | Gly | Gly | Ser | Glu | Tyr | Pro | Lys | Ala | Pro | Gly | Asn | Tyr | Tyr | Asp | Gly | |
| | | | 155 | | | | | 160 | | | | | 165 | | | |

| gac | tct | tgg | gag | cct | cgc | gac | gag | gtt | aaa | ggt | gac | gta | gct | cgc | atg | 624 |
| Asp | Ser | Trp | Glu | Pro | Arg | Asp | Glu | Val | Lys | Gly | Asp | Val | Ala | Arg | Met | |
| | | | 170 | | | | | 175 | | | | | 180 | | | |

| ctt | ttc | tat | atg | gca | gtt | cgc | tat | gag | gga | gac | gac | ggc | tac | cct | gac | 672 |
| Leu | Phe | Tyr | Met | Ala | Val | Arg | Tyr | Glu | Gly | Asp | Asp | Gly | Tyr | Pro | Asp | |
| | | | 185 | | | | | 190 | | | | | 195 | | | |

| ctt | gag | ctt | aac | gac | aaa | act | ggt | aac | gga | tca | gca | cct | tac | atg | ggc | 720 |
| Leu | Glu | Leu | Asn | Asp | Lys | Thr | Gly | Asn | Gly | Ser | Ala | Pro | Tyr | Met | Gly | |
| | 200 | | | | | 205 | | | | | 210 | | | | | |

| aaa | ctt | tca | gtt | ctt | ctt | aag | tgg | aac | aaa | caa | gac | cct | gtt | gac | tca | 768 |
| Lys | Leu | Ser | Val | Leu | Leu | Lys | Trp | Asn | Lys | Gln | Asp | Pro | Val | Asp | Ser | |
| 215 | | | | 220 | | | | | 225 | | | | | 230 | | |

| aaa | gag | aaa | cgt | cgc | aac | gag | ctt | atc | tac | gag | gac | tac | caa | cac | aac | 816 |

```
Lys Glu Lys Arg Arg Asn Glu Leu Ile Tyr Glu Asp Tyr Gln His Asn
                235                 240                 245 cgc aac cct ttc atc gac cat cct gag tgg gca gac gag atc tgg aaa      864
Arg Asn Pro Phe Ile Asp His Pro Glu Trp Ala Asp Glu Ile Trp Lys
        250                 255                 260 tag                                                                   867
```

<210> SEQ ID NO 11
<211> LENGTH: 288
<212> TYPE: PRT
<213> ORGANISM: Artificial Sequence
<220> FEATURE:
<223> OTHER INFORMATION: Synthetic Construct

<400> SEQUENCE: 11

```
Met Thr Lys Lys Leu Trp Phe Leu Pro Ile Val Cys Leu Tyr Phe Ile
    -25                 -20                 -15

Phe Gly Trp Ala Ala Pro Ser Ala Ser Ala Gly Ala Pro Ala Ala Thr
-10                  -5              -1  1                   5

Asn Leu Tyr Ser Arg Arg Ala Val Ser Thr Ala Gly Thr Phe Phe Pro
                10                  15                  20

Gln Thr Ala Ser Ser Val Ile Thr Pro Ser Ala Asp Thr Asp Thr Tyr
            25                  30                  35

Tyr Lys Glu Ala Ser Gly Lys Ser Gly Thr Ser Leu Lys Ser Ala Leu
    40                  45                  50

His Arg Ile Ile Ser Gly Asn Thr Lys Leu Ser Tyr Ser Gln Val Trp
55                  60                  65                  70

Asp Ala Leu Lys Glu Thr Asp Glu Asp Pro Ala Asn Pro Asn Asn Val
                75                  80                  85

Ile Leu Leu Tyr Thr Gln Glu Ser Arg Ala Lys Ser Lys Asn Gly Gly
                90                  95                  100

Ser Val Gly Asp Trp Asn Arg Glu His Val Trp Ala Lys Ser His Gly
            105                 110                 115

Asn Phe Gly Thr Ser Ala Gly Pro Gly Thr Asp Ile His His Leu Arg
    120                 125                 130

Pro Ala Asp Val Gln Val Asn Arg Ala Arg Gly Asn Met Asp Phe Asp
135                 140                 145                 150

Asn Gly Gly Ser Glu Tyr Pro Lys Ala Pro Gly Asn Tyr Tyr Asp Gly
                155                 160                 165

Asp Ser Trp Glu Pro Arg Asp Glu Val Lys Gly Asp Val Ala Arg Met
            170                 175                 180

Leu Phe Tyr Met Ala Val Arg Tyr Glu Gly Asp Gly Tyr Pro Asp
    185                 190                 195

Leu Glu Leu Asn Asp Lys Thr Gly Asn Gly Ser Ala Pro Tyr Met Gly
200                 205                 210

Lys Leu Ser Val Leu Leu Lys Trp Asn Lys Gln Asp Pro Val Asp Ser
215                 220                 225                 230

Lys Glu Lys Arg Arg Asn Glu Leu Ile Tyr Glu Asp Tyr Gln His Asn
                235                 240                 245

Arg Asn Pro Phe Ile Asp His Pro Glu Trp Ala Asp Glu Ile Trp Lys
        250                 255                 260
```

<210> SEQ ID NO 12
<211> LENGTH: 867
<212> TYPE: DNA
<213> ORGANISM: Bacillus subtilis
<220> FEATURE:

<221> NAME/KEY: CDS
<222> LOCATION: (1)..(864)
<220> FEATURE:
<221> NAME/KEY: sig_peptide
<222> LOCATION: (1)..(78)
<220> FEATURE:
<221> NAME/KEY: mat_peptide
<222> LOCATION: (79)..(864)

<400> SEQUENCE: 12

| | | |
|---|---|---|
| atg aca aaa aaa gca tgg ttt ctg ccg ctc gtt tgt gta tta ctg att<br>Met Thr Lys Lys Ala Trp Phe Leu Pro Leu Val Cys Val Leu Leu Ile<br>-25           -20                -15 | | 48 |
| tcc gga tgg ttt gca ccc gcc gct tca gca agt ccg cag acc gca tta<br>Ser Gly Trp Phe Ala Pro Ala Ala Ser Ala Ser Pro Gln Thr Ala Leu<br>-10            -5             -1  1                 5 | | 96 |
| agc ctg aat gac cga ttc gcg tct tcc cct tca gga acc ggg ggc ctt<br>Ser Leu Asn Asp Arg Phe Ala Ser Ser Pro Ser Gly Thr Gly Gly Leu<br>             10                  15                 20 | | 144 |
| ctt tca tta gcc gcc ccc gct gca ccc tac act gac aca gat acc tat<br>Leu Ser Leu Ala Ala Pro Ala Ala Pro Tyr Thr Asp Thr Asp Thr Tyr<br>         25                  30                  35 | | 192 |
| tat gaa ggg act gaa gga aaa aca gga gaa tcg cta aaa aac gcc ttg<br>Tyr Glu Gly Thr Glu Gly Lys Thr Gly Glu Ser Leu Lys Asn Ala Leu<br> 40                  45                  50 | | 240 |
| cac cgc atc atc agc ggg cac aca atg ctg tcc tac agc gag gta tgg<br>His Arg Ile Ile Ser Gly His Thr Met Leu Ser Tyr Ser Glu Val Trp<br>55                  60                  65                  70 | | 288 |
| aac gcg ctg aaa gaa acc gat gaa gac ccg aga aac cca aat aac gtc<br>Asn Ala Leu Lys Glu Thr Asp Glu Asp Pro Arg Asn Pro Asn Asn Val<br>             75                  80                  85 | | 336 |
| atc ctg ctc tat acg aat gaa tcc cgg tcg aaa aac ctg aac ggc ggc<br>Ile Leu Leu Tyr Thr Asn Glu Ser Arg Ser Lys Asn Leu Asn Gly Gly<br>         90                  95                 100 | | 384 |
| aat gtc ggc gat tgg aac cgc gag cac gtt tgg gcg aaa tcc cat ggt<br>Asn Val Gly Asp Trp Asn Arg Glu His Val Trp Ala Lys Ser His Gly<br>    105                 110                 115 | | 432 |
| gac ttt ggt aca agc aag ggg cct ggc acc gac att cat cat ttg cgc<br>Asp Phe Gly Thr Ser Lys Gly Pro Gly Thr Asp Ile His His Leu Arg<br>120                 125                 130 | | 480 |
| ccg gct gat gtt caa gtc aac agc gca aga gga aat atg gat ttt gac<br>Pro Ala Asp Val Gln Val Asn Ser Ala Arg Gly Asn Met Asp Phe Asp<br>135                 140                 145                 150 | | 528 |
| aac ggc ggc aca gaa cat gcg aaa gcg ccc gga aat tat tat gac gga<br>Asn Gly Gly Thr Glu His Ala Lys Ala Pro Gly Asn Tyr Tyr Asp Gly<br>             155                 160                 165 | | 576 |
| gat tca tgg gag ccc cgt gat gat gtg aaa ggc gat gtc gcc cgc atg<br>Asp Ser Trp Glu Pro Arg Asp Asp Val Lys Gly Asp Val Ala Arg Met<br>         170                 175                 180 | | 624 |
| ctg ttt tac atg gct gtc cgt tat gaa ggt gat gac ggg tac cct gat<br>Leu Phe Tyr Met Ala Val Arg Tyr Glu Gly Asp Asp Gly Tyr Pro Asp<br>    185                 190                 195 | | 672 |
| ctt gaa ctg aat gat aaa aca ggc aac ggc tca gct cct tat cac gga<br>Leu Glu Leu Asn Asp Lys Thr Gly Asn Gly Ser Ala Pro Tyr His Gly<br>200                 205                 210 | | 720 |
| aaa caa tct gtc ctg ctc gaa tgg aat aag caa gac cct gtt gat gac<br>Lys Gln Ser Val Leu Leu Glu Trp Asn Lys Gln Asp Pro Val Asp Asp<br>215                 220                 225                 230 | | 768 |
| cgc gag cga aaa aga aat gaa atc att tat gag aaa tat cag cac aac<br>Arg Glu Arg Lys Arg Asn Glu Ile Ile Tyr Glu Lys Tyr Gln His Asn<br>             235                 240                 245 | | 816 |

```
cgc aat cca ttt atc gac cac ccc gaa tgg gcg gac gag att tgg cca      864
Arg Asn Pro Phe Ile Asp His Pro Glu Trp Ala Asp Glu Ile Trp Pro
    250                 255                 260 taa                                                                   867
```

<210> SEQ ID NO 13
<211> LENGTH: 288
<212> TYPE: PRT
<213> ORGANISM: Bacillus subtilis

<400> SEQUENCE: 13

```
Met Thr Lys Lys Ala Trp Phe Leu Pro Leu Val Cys Val Leu Leu Ile
        -25                 -20                 -15

Ser Gly Trp Phe Ala Pro Ala Ala Ser Ala Ser Pro Gln Thr Ala Leu
-10                  -5                  -1   1               5

Ser Leu Asn Asp Arg Phe Ala Ser Pro Ser Gly Thr Gly Gly Leu
             10                  15                  20

Leu Ser Leu Ala Ala Pro Ala Ala Pro Tyr Thr Asp Thr Asp Thr Tyr
         25                  30                  35

Tyr Glu Gly Thr Glu Gly Lys Thr Gly Glu Ser Leu Lys Asn Ala Leu
     40                  45                  50

His Arg Ile Ile Ser Gly His Thr Met Leu Ser Tyr Ser Glu Val Trp
55                   60                  65                      70

Asn Ala Leu Lys Glu Thr Asp Glu Asp Pro Arg Asn Pro Asn Asn Val
             75                  80                  85

Ile Leu Leu Tyr Thr Asn Glu Ser Arg Ser Lys Asn Leu Asn Gly Gly
             90                  95                  100

Asn Val Gly Asp Trp Asn Arg Glu His Val Trp Ala Lys Ser His Gly
        105                 110                 115

Asp Phe Gly Thr Ser Lys Gly Pro Gly Thr Asp Ile His His Leu Arg
        120                 125                 130

Pro Ala Asp Val Gln Val Asn Ser Ala Arg Gly Asn Met Asp Phe Asp
135                 140                 145                 150

Asn Gly Gly Thr Glu His Ala Lys Ala Pro Gly Asn Tyr Tyr Asp Gly
            155                 160                 165

Asp Ser Trp Glu Pro Arg Asp Val Lys Gly Asp Val Ala Arg Met
            170                 175                 180

Leu Phe Tyr Met Ala Val Arg Tyr Glu Gly Asp Asp Gly Tyr Pro Asp
        185                 190                 195

Leu Glu Leu Asn Asp Lys Thr Gly Asn Gly Ser Ala Pro Tyr His Gly
    200                 205                 210

Lys Gln Ser Val Leu Leu Glu Trp Asn Lys Gln Asp Pro Val Asp Asp
215                 220                 225                 230

Arg Glu Arg Lys Arg Asn Glu Ile Ile Tyr Glu Lys Tyr Gln His Asn
                235                 240                 245

Arg Asn Pro Phe Ile Asp His Pro Glu Trp Ala Asp Glu Ile Trp Pro
        250                 255                 260
```

<210> SEQ ID NO 14
<211> LENGTH: 262
<212> TYPE: PRT
<213> ORGANISM: Bacillus subtilis

<400> SEQUENCE: 14

```
Ser Pro Gln Thr Ala Leu Ser Leu Asn Asp Arg Phe Ala Ser Pro
1               5                   10                  15
```

```
Ser Gly Thr Gly Gly Leu Leu Ser Leu Ala Ala Pro Ala Ala Pro Tyr
            20                  25                  30

Thr Asp Thr Asp Thr Tyr Tyr Glu Gly Thr Glu Gly Lys Thr Gly Glu
        35                  40                  45

Ser Leu Lys Asn Ala Leu His Arg Ile Ile Ser Gly His Thr Met Leu
 50                  55                  60

Ser Tyr Ser Glu Val Trp Asn Ala Leu Lys Glu Thr Asp Glu Asp Pro
 65                  70                  75                  80

Arg Asn Pro Asn Asn Val Ile Leu Leu Tyr Thr Asn Glu Ser Arg Ser
                 85                  90                  95

Lys Asn Leu Asn Gly Gly Asn Val Gly Asp Trp Asn Arg Glu His Val
            100                 105                 110

Trp Ala Lys Ser His Gly Asp Phe Gly Thr Ser Lys Gly Pro Gly Thr
            115                 120                 125

Asp Ile His His Leu Arg Pro Ala Asp Val Gln Val Asn Ser Ala Arg
        130                 135                 140

Gly Asn Met Asp Phe Asp Asn Gly Thr Glu His Ala Lys Ala Pro
145                 150                 155                 160

Gly Asn Tyr Tyr Asp Gly Asp Ser Trp Glu Pro Arg Asp Asp Val Lys
                165                 170                 175

Gly Asp Val Ala Arg Met Leu Phe Tyr Met Ala Val Arg Tyr Glu Gly
            180                 185                 190

Asp Asp Gly Tyr Pro Asp Leu Glu Leu Asn Asp Lys Thr Gly Asn Gly
        195                 200                 205

Ser Ala Pro Tyr His Gly Lys Gln Ser Val Leu Leu Glu Trp Asn Lys
210                 215                 220

Gln Asp Pro Val Asp Asp Arg Glu Arg Lys Arg Asn Glu Ile Ile Tyr
225                 230                 235                 240

Glu Lys Tyr Gln His Asn Arg Asn Pro Phe Ile Asp His Pro Glu Trp
                245                 250                 255

Ala Asp Glu Ile Trp Pro
            260

<210> SEQ ID NO 15
<211> LENGTH: 867
<212> TYPE: DNA
<213> ORGANISM: Artificial Sequence
<220> FEATURE:
<223> OTHER INFORMATION: Codon optimized synthetic sequence
<220> FEATURE:
<221> NAME/KEY: CDS
<222> LOCATION: (1)..(864)
<220> FEATURE:
<221> NAME/KEY: sig_peptide
<222> LOCATION: (1)..(78)
<220> FEATURE:
<221> NAME/KEY: mat_peptide
<222> LOCATION: (79)..(864)

<400> SEQUENCE: 15 atg act aag aaa gca tgg ttc ctt cct ctt gtt tgc gta ctt ttg atc      48
Met Thr Lys Lys Ala Trp Phe Leu Pro Leu Val Cys Val Leu Leu Ile
    -25                 -20                 -15 tca gga tgg ttt gct cct gcg gct tct gct tct cct caa aca gcg ctt      96
Ser Gly Trp Phe Ala Pro Ala Ala Ser Ala Ser Pro Gln Thr Ala Leu
-10                  -5              -1   1               5 tct ctt aac gac cgt ttc gcg tct tct cca tca gga act ggc ggt tta     144
Ser Leu Asn Asp Arg Phe Ala Ser Ser Pro Ser Gly Thr Gly Gly Leu
             10                  15                  20
```

| | |
|---|---|
| ctt tct tta gcg gct cca gct gct cca tac act gac act gat acg tac<br>Leu Ser Leu Ala Ala Pro Ala Ala Pro Tyr Thr Asp Thr Asp Thr Tyr<br>     25                           30                        35 | 192 |
| tat gag ggt act gag gga aaa act ggt gaa tct ttg aaa aac gca tta<br>Tyr Glu Gly Thr Glu Gly Lys Thr Gly Glu Ser Leu Lys Asn Ala Leu<br> 40                        45                        50 | 240 |
| cac cgc atc atc tca ggt cat act atg tta tca tac tct gag gtt tgg<br>His Arg Ile Ile Ser Gly His Thr Met Leu Ser Tyr Ser Glu Val Trp<br>55                       60                        65                        70 | 288 |
| aat gcg ctt aaa gag act gat gaa gat cct cgc aat cca aac aac gta<br>Asn Ala Leu Lys Glu Thr Asp Glu Asp Pro Arg Asn Pro Asn Asn Val<br>               75                        80                        85 | 336 |
| atc ctt ctt tac act aac gaa tct cgt agc aaa aac tta aac ggt gga<br>Ile Leu Leu Tyr Thr Asn Glu Ser Arg Ser Lys Asn Leu Asn Gly Gly<br>         90                        95                             100 | 384 |
| aac gtt ggc gat tgg aat cgt gaa cac gta tgg gcc aaa tct cac ggt<br>Asn Val Gly Asp Trp Asn Arg Glu His Val Trp Ala Lys Ser His Gly<br>              105                    110                    115 | 432 |
| gat ttc ggt act agc aaa gga cca ggt aca gac att cac cat ctt cgt<br>Asp Phe Gly Thr Ser Lys Gly Pro Gly Thr Asp Ile His His Leu Arg<br>120                       125                        130 | 480 |
| cca gct gat gtt caa gta aac tca gct cgt gga aac atg gat ttc gac<br>Pro Ala Asp Val Gln Val Asn Ser Ala Arg Gly Asn Met Asp Phe Asp<br>135                       140                        145                    150 | 528 |
| aac ggt ggt aca gaa cat gca aaa gct cct gga aac tac tat gat gga<br>Asn Gly Gly Thr Glu His Ala Lys Ala Pro Gly Asn Tyr Tyr Asp Gly<br>                     155                        160                        165 | 576 |
| gat tca tgg gaa cca cgt gac gac gtt aaa gga gat gta gcg cgt atg<br>Asp Ser Trp Glu Pro Arg Asp Asp Val Lys Gly Asp Val Ala Arg Met<br>170                       175                        180 | 624 |
| ctt ttc tat atg gca gtt cgt tat gaa ggc gat gat ggt tac cct gat<br>Leu Phe Tyr Met Ala Val Arg Tyr Glu Gly Asp Asp Gly Tyr Pro Asp<br>                   185                        190                        195 | 672 |
| ttg gaa ttg aac gac aaa act gga aat ggc tct gca ccg tac cat ggt<br>Leu Glu Leu Asn Asp Lys Thr Gly Asn Gly Ser Ala Pro Tyr His Gly<br>200                       205                        210 | 720 |
| aaa caa tct gtt ctt ctt gag tgg aac aaa caa gac cca gtt gac gat<br>Lys Gln Ser Val Leu Leu Glu Trp Asn Lys Gln Asp Pro Val Asp Asp<br>215                       220                        225                    230 | 768 |
| cgt gaa cgt aaa cgc aac gaa atc atc tac gag aaa tac caa cat aat<br>Arg Glu Arg Lys Arg Asn Glu Ile Ile Tyr Glu Lys Tyr Gln His Asn<br>                   235                        240                        245 | 816 |
| cgc aat ccg ttt atc gac cac ccg gag tgg gca gat gaa atc tgg cca<br>Arg Asn Pro Phe Ile Asp His Pro Glu Trp Ala Asp Glu Ile Trp Pro<br>              250                    255                    260 | 864 |
| taa | 867 |

```
<210> SEQ ID NO 16
<211> LENGTH: 288
<212> TYPE: PRT
<213> ORGANISM: Artificial Sequence
<220> FEATURE:
<223> OTHER INFORMATION: Synthetic Construct

<400> SEQUENCE: 16
```

Met Thr Lys Lys Ala Trp Phe Leu Pro Leu Val Cys Val Leu Leu Ile
        -25                    -20                    -15

Ser Gly Trp Phe Ala Pro Ala Ala Ser Ala Ser Pro Gln Thr Ala Leu
-10                   -5                  -1  1               5

Ser Leu Asn Asp Arg Phe Ala Ser Ser Pro Ser Gly Thr Gly Gly Leu

```
            10                  15                  20
Leu Ser Leu Ala Ala Pro Ala Pro Tyr Thr Asp Thr Asp Thr Tyr
         25                  30                  35

Tyr Glu Gly Thr Glu Gly Lys Thr Gly Glu Ser Leu Lys Asn Ala Leu
         40                  45                  50

His Arg Ile Ile Ser Gly His Thr Met Leu Ser Tyr Ser Glu Val Trp
55                   60                  65                  70

Asn Ala Leu Lys Glu Thr Asp Glu Asp Pro Arg Asn Pro Asn Asn Val
                 75                  80                  85

Ile Leu Leu Tyr Thr Asn Glu Ser Arg Ser Lys Asn Leu Asn Gly Gly
                 90                  95                 100

Asn Val Gly Asp Trp Asn Arg Glu His Val Trp Ala Lys Ser His Gly
            105                 110                 115

Asp Phe Gly Thr Ser Lys Gly Pro Gly Thr Asp Ile His His Leu Arg
        120                 125                 130

Pro Ala Asp Val Gln Val Asn Ser Ala Arg Gly Asn Met Asp Phe Asp
135                 140                 145                 150

Asn Gly Gly Thr Glu His Ala Lys Ala Pro Gly Asn Tyr Tyr Asp Gly
                155                 160                 165

Asp Ser Trp Glu Pro Arg Asp Asp Val Lys Gly Asp Val Ala Arg Met
            170                 175                 180

Leu Phe Tyr Met Ala Val Arg Tyr Glu Gly Asp Asp Gly Tyr Pro Asp
        185                 190                 195

Leu Glu Leu Asn Asp Lys Thr Gly Asn Gly Ser Ala Pro Tyr His Gly
200                 205                 210

Lys Gln Ser Val Leu Leu Glu Trp Asn Lys Gln Asp Pro Val Asp Asp
215                 220                 225                 230

Arg Glu Arg Lys Arg Asn Glu Ile Ile Tyr Glu Lys Tyr Gln His Asn
                235                 240                 245

Arg Asn Pro Phe Ile Asp His Pro Glu Trp Ala Asp Glu Ile Trp Pro
            250                 255                 260

<210> SEQ ID NO 17
<211> LENGTH: 774
<212> TYPE: DNA
<213> ORGANISM: Saccharopolyspora hirsuta
<220> FEATURE:
<221> NAME/KEY: CDS
<222> LOCATION: (1)..(771)
<220> FEATURE:
<221> NAME/KEY: sig_peptide
<222> LOCATION: (1)..(81)
<220> FEATURE:
<221> NAME/KEY: mat_peptide
<222> LOCATION: (82)..(771)

<400> SEQUENCE: 17 atg aag acc acc cga ttg aag tcg tta tcc ctg tta ctc ggc atc gcc      48
Met Lys Thr Thr Arg Leu Lys Ser Leu Ser Leu Leu Leu Gly Ile Ala
        -25                 -20                 -15 ctg gtg gcg atc ccg gta ccg tcc gcg gcc gcg tcc acc gcc gac gac      96
Leu Val Ala Ile Pro Val Pro Ser Ala Ala Ala Ser Thr Ala Asp Asp
    -10                 -5              -1  1                   5 tac tac cag gac gcg atc ggc aag acc ggc ccg gag ctc gag gcc gcg     144
Tyr Tyr Gln Asp Ala Ile Gly Lys Thr Gly Pro Glu Leu Glu Ala Ala
                    10                  15                  20 ctg cac cag atc atc agc agc ggc acc acc acg ttg agc tac gac gag     192
Leu His Gln Ile Ile Ser Ser Gly Thr Thr Thr Leu Ser Tyr Asp Glu
            25                  30                  35
```

```
gtg tgg gac gcg ctc aag gtc acc gac gag gac ccg aac aac acc aac    240
Val Trp Asp Ala Leu Lys Val Thr Asp Glu Asp Pro Asn Asn Thr Asn
        40                  45                  50 aac gtg gtc ctg ctc tac acc ggc cgg tcg cag agc aag gac tcc aac    288
Asn Val Val Leu Leu Tyr Thr Gly Arg Ser Gln Ser Lys Asp Ser Asn
    55                  60                  65 ggc ggc gac gcc gac gac tgg aac cgc gag cac gtc tgg gcc aag tcg    336
Gly Gly Asp Ala Asp Asp Trp Asn Arg Glu His Val Trp Ala Lys Ser
70                  75                  80                  85 cac ggc gac ttc ggc acc gcg ccc ggt ccc ggc acc gac gtc cac cac    384
His Gly Asp Phe Gly Thr Ala Pro Gly Pro Gly Thr Asp Val His His
                90                  95                  100 ctg cgc ccg acc gac gtc tcg gtc aac tcc gag cgc ggc agc aag gac    432
Leu Arg Pro Thr Asp Val Ser Val Asn Ser Glu Arg Gly Ser Lys Asp
            105                 110                 115 ttc gac atg ggc ggc gac gag gtc gcc gag gcg ccc ggc aac ttc acc    480
Phe Asp Met Gly Gly Asp Glu Val Ala Glu Ala Pro Gly Asn Phe Thr
        120                 125                 130 gac ggc gac tcg tgg gag ccg cgc gac gag gtc aag ggc gac gtc gcc    528
Asp Gly Asp Ser Trp Glu Pro Arg Asp Glu Val Lys Gly Asp Val Ala
    135                 140                 145 cgg atg atc ttc tac atg tcg gtc cgc tac gag ggt gac gac ggc ttc    576
Arg Met Ile Phe Tyr Met Ser Val Arg Tyr Glu Gly Asp Asp Gly Phe
150                 155                 160                 165 gcc gac ctg gag gtc aac gac gag gtc ggc aac ggc agc gcc ccg cac    624
Ala Asp Leu Glu Val Asn Asp Glu Val Gly Asn Gly Ser Ala Pro His
                170                 175                 180 atc ggc cgg gtc tcg gtg ctc aag cag tgg cac gag cag gac ccg ccg    672
Ile Gly Arg Val Ser Val Leu Lys Gln Trp His Glu Gln Asp Pro Pro
            185                 190                 195 gac gcc gcg gag cag cgc cgc aac cag gtc atc ttc gac cag ttc cag    720
Asp Ala Ala Glu Gln Arg Arg Asn Gln Val Ile Phe Asp Gln Phe Gln
        200                 205                 210 cac aac cgg aac ccg ttc atc gac cac ccg gag tgg gtc gcc gag atc    768
His Asn Arg Asn Pro Phe Ile Asp His Pro Glu Trp Val Ala Glu Ile
    215                 220                 225 tgg tga                                                             774
Trp
230

<210> SEQ ID NO 18
<211> LENGTH: 257
<212> TYPE: PRT
<213> ORGANISM: Saccharopolyspora hirsuta

<400> SEQUENCE: 18

Met Lys Thr Thr Arg Leu Lys Ser Leu Ser Leu Leu Leu Gly Ile Ala
        -25                 -20                 -15

Leu Val Ala Ile Pro Val Pro Ser Ala Ala Ala Ser Thr Ala Asp Asp
        -10                 -5              -1  1               5

Tyr Tyr Gln Asp Ala Ile Gly Lys Thr Gly Pro Glu Leu Glu Ala Ala
                10                  15                  20

Leu His Gln Ile Ile Ser Ser Gly Thr Thr Thr Leu Ser Tyr Asp Glu
            25                  30                  35

Val Trp Asp Ala Leu Lys Val Thr Asp Glu Asp Pro Asn Asn Thr Asn
        40                  45                  50

Asn Val Val Leu Leu Tyr Thr Gly Arg Ser Gln Ser Lys Asp Ser Asn
    55                  60                  65
```

```
Gly Gly Asp Ala Asp Asp Trp Asn Arg Glu His Val Trp Ala Lys Ser
 70                  75                  80                  85

His Gly Asp Phe Gly Thr Ala Pro Gly Pro Gly Thr Asp Val His His
             90                  95                 100

Leu Arg Pro Thr Asp Val Ser Val Asn Ser Glu Arg Gly Ser Lys Asp
            105                 110                 115

Phe Asp Met Gly Gly Asp Glu Val Ala Glu Ala Pro Gly Asn Phe Thr
        120                 125                 130

Asp Gly Asp Ser Trp Glu Pro Arg Asp Glu Val Lys Gly Asp Val Ala
    135                 140                 145

Arg Met Ile Phe Tyr Met Ser Val Arg Tyr Glu Gly Asp Asp Gly Phe
150                 155                 160                 165

Ala Asp Leu Glu Val Asn Asp Glu Val Gly Asn Gly Ser Ala Pro His
            170                 175                 180

Ile Gly Arg Val Ser Val Leu Lys Gln Trp His Glu Gln Asp Pro Pro
                185                 190                 195

Asp Ala Ala Glu Gln Arg Arg Asn Gln Val Ile Phe Asp Gln Phe Gln
        200                 205                 210

His Asn Arg Asn Pro Phe Ile Asp His Pro Glu Trp Val Ala Glu Ile
    215                 220                 225

Trp
230

<210> SEQ ID NO 19
<211> LENGTH: 230
<212> TYPE: PRT
<213> ORGANISM: Saccharopolyspora hirsuta

<400> SEQUENCE: 19

Ser Thr Ala Asp Asp Tyr Tyr Gln Asp Ala Ile Gly Lys Thr Gly Pro
  1               5                  10                  15

Glu Leu Glu Ala Ala Leu His Gln Ile Ile Ser Ser Gly Thr Thr Thr
             20                  25                  30

Leu Ser Tyr Asp Glu Val Trp Asp Ala Leu Lys Val Thr Asp Glu Asp
         35                  40                  45

Pro Asn Asn Thr Asn Asn Val Val Leu Leu Tyr Thr Gly Arg Ser Gln
 50                  55                  60

Ser Lys Asp Ser Asn Gly Gly Asp Ala Asp Asp Trp Asn Arg Glu His
 65                  70                  75                  80

Val Trp Ala Lys Ser His Gly Asp Phe Gly Thr Ala Pro Gly Pro Gly
                 85                  90                  95

Thr Asp Val His His Leu Arg Pro Thr Asp Val Ser Val Asn Ser Glu
            100                 105                 110

Arg Gly Ser Lys Asp Phe Asp Met Gly Gly Asp Glu Val Ala Glu Ala
        115                 120                 125

Pro Gly Asn Phe Thr Asp Gly Asp Ser Trp Glu Pro Arg Asp Glu Val
    130                 135                 140

Lys Gly Asp Val Ala Arg Met Ile Phe Tyr Met Ser Val Arg Tyr Glu
145                 150                 155                 160

Gly Asp Asp Gly Phe Ala Asp Leu Glu Val Asn Asp Glu Val Gly Asn
                165                 170                 175

Gly Ser Ala Pro His Ile Gly Arg Val Ser Val Leu Lys Gln Trp His
            180                 185                 190

Glu Gln Asp Pro Pro Asp Ala Ala Glu Gln Arg Arg Asn Gln Val Ile
        195                 200                 205
```

```
Phe Asp Gln Phe Gln His Asn Arg Asn Pro Phe Ile Asp His Pro Glu
    210                 215                 220

Trp Val Ala Glu Ile Trp
225                 230

<210> SEQ ID NO 20
<211> LENGTH: 822
<212> TYPE: DNA
<213> ORGANISM: Bacillus licheniformis
<220> FEATURE:
<221> NAME/KEY: CDS
<222> LOCATION: (1)..(819)
<220> FEATURE:
<221> NAME/KEY: sig_peptide
<222> LOCATION: (1)..(75)
<220> FEATURE:
<221> NAME/KEY: mat_peptide
<222> LOCATION: (76)..(819)

<400> SEQUENCE: 20 atg aac cga aag tgt ctc ata ccg ttt att ttg atg ctg tca gcg atg    48
Met Asn Arg Lys Cys Leu Ile Pro Phe Ile Leu Met Leu Ser Ala Met
-25                 -20                 -15                 -10 tgc gcg ccc acc caa aac gca gaa gcc ttc cag ttg ttt tcc tta cac    96
Cys Ala Pro Thr Gln Asn Ala Glu Ala Phe Gln Leu Phe Ser Leu His
            -5                  -1   1               5 gtc cag ccc cat cag tcc tcg gct ccg gcg gat tac tat gaa cag gcg   144
Val Gln Pro His Gln Ser Ser Ala Pro Ala Asp Tyr Tyr Glu Gln Ala
                10                  15                  20 caa ggc aaa aca ggc gaa gct tta aaa caa gcg ctt cac gac aca atc   192
Gln Gly Lys Thr Gly Glu Ala Leu Lys Gln Ala Leu His Asp Thr Ile
        25                  30                  35 gac gat cat aga gag ctt tct tac agc gag gta tgg gaa gcg ctg aaa   240
Asp Asp His Arg Glu Leu Ser Tyr Ser Glu Val Trp Glu Ala Leu Lys
 40                  45                  50                  55 gca acg gac gaa gat ccg gcc aat cga aat aac gtg att ctc ata tat   288
Ala Thr Asp Glu Asp Pro Ala Asn Arg Asn Asn Val Ile Leu Ile Tyr
                    60                  65                  70 tcc aga gag tcg cgc tct aaa cag gcg aac ggg ggg caa act ggc gat   336
Ser Arg Glu Ser Arg Ser Lys Gln Ala Asn Gly Gly Gln Thr Gly Asp
            75                  80                  85 tgg aac cgc gag cac gta tgg gca aaa tcg cac ggt gat ttc gga aca   384
Trp Asn Arg Glu His Val Trp Ala Lys Ser His Gly Asp Phe Gly Thr
        90                  95                 100 agc aaa gga ccc gga aca gat ttg cat cat ctc agg ccc agc gat gtg   432
Ser Lys Gly Pro Gly Thr Asp Leu His His Leu Arg Pro Ser Asp Val
    105                 110                 115 caa gta aac gcc gcc cgc gga aac ctt gat ttc gac gaa ggc ggc agc   480
Gln Val Asn Ala Ala Arg Gly Asn Leu Asp Phe Asp Glu Gly Gly Ser
120                 125                 130                 135 ccc tat ccc ggt tct ccc gga aac cgc tat gac ggc gat tcc tgg gaa   528
Pro Tyr Pro Gly Ser Pro Gly Asn Arg Tyr Asp Gly Asp Ser Trp Glu
                140                 145                 150 cct gac aaa agc att aaa ggc gat gtc gcc aga atg att ttc tat atg   576
Pro Asp Lys Ser Ile Lys Gly Asp Val Ala Arg Met Ile Phe Tyr Met
            155                 160                 165 gcg gtc cgc tat gaa ggg gac gac ggc cag ccg gat ctt gaa atg aac   624
Ala Val Arg Tyr Glu Gly Asp Asp Gly Gln Pro Asp Leu Glu Met Asn
        170                 175                 180 gac aca acg aac aac gga tct aaa ccg tac cac gga aaa atg tcg gtt   672
Asp Thr Thr Asn Asn Gly Ser Lys Pro Tyr His Gly Lys Met Ser Val
    185                 190                 195
```

```
tta ttg aaa tgg cac cat gaa gat cct gtc gat gcc ctt gaa aga aag     720
Leu Leu Lys Trp His His Glu Asp Pro Val Asp Ala Leu Glu Arg Lys
200             205                 210                 215 cgg aac gac atc atc tat cag caa tac cag cat aac cgc aat cca ttc     768
Arg Asn Asp Ile Ile Tyr Gln Gln Tyr Gln His Asn Arg Asn Pro Phe
                220                 225                 230 att gat cac cct gaa tgg gcg gag gat att tgg ggc tca ggc gtt ttg     816
Ile Asp His Pro Glu Trp Ala Glu Asp Ile Trp Gly Ser Gly Val Leu
            235                 240                 245 aat tga                                                             822
Asn

<210> SEQ ID NO 21
<211> LENGTH: 273
<212> TYPE: PRT
<213> ORGANISM: Bacillus licheniformis

<400> SEQUENCE: 21

Met Asn Arg Lys Cys Leu Ile Pro Phe Ile Leu Met Leu Ser Ala Met
-25                 -20                 -15                 -10

Cys Ala Pro Thr Gln Asn Ala Glu Ala Phe Gln Leu Phe Ser Leu His
                -5                  -1  1               5

Val Gln Pro His Gln Ser Ser Ala Pro Ala Asp Tyr Tyr Glu Gln Ala
            10                  15                  20

Gln Gly Lys Thr Gly Glu Ala Leu Lys Gln Ala Leu His Asp Thr Ile
        25                  30                  35

Asp Asp His Arg Glu Leu Ser Tyr Ser Glu Val Trp Glu Ala Leu Lys
40                  45                  50                  55

Ala Thr Asp Glu Asp Pro Ala Asn Arg Asn Asn Val Ile Leu Ile Tyr
                60                  65                  70

Ser Arg Glu Ser Arg Ser Lys Gln Ala Asn Gly Gly Gln Thr Gly Asp
            75                  80                  85

Trp Asn Arg Glu His Val Trp Ala Lys Ser His Gly Asp Phe Gly Thr
        90                  95                  100

Ser Lys Gly Pro Gly Thr Asp Leu His His Leu Arg Pro Ser Asp Val
    105                 110                 115

Gln Val Asn Ala Ala Arg Gly Asn Leu Asp Phe Asp Glu Gly Gly Ser
120                 125                 130                 135

Pro Tyr Pro Gly Ser Pro Gly Asn Arg Tyr Asp Gly Asp Ser Trp Glu
                140                 145                 150

Pro Asp Lys Ser Ile Lys Gly Asp Val Ala Arg Met Ile Phe Tyr Met
            155                 160                 165

Ala Val Arg Tyr Glu Gly Asp Asp Gly Gln Pro Asp Leu Glu Met Asn
        170                 175                 180

Asp Thr Thr Asn Asn Gly Ser Lys Pro Tyr His Gly Lys Met Ser Val
    185                 190                 195

Leu Leu Lys Trp His His Glu Asp Pro Val Asp Ala Leu Glu Arg Lys
200                 205                 210                 215

Arg Asn Asp Ile Ile Tyr Gln Gln Tyr Gln His Asn Arg Asn Pro Phe
                220                 225                 230

Ile Asp His Pro Glu Trp Ala Glu Asp Ile Trp Gly Ser Gly Val Leu
            235                 240                 245

Asn

<210> SEQ ID NO 22
```

```
<211> LENGTH: 248
<212> TYPE: PRT
<213> ORGANISM: Bacillus licheniformis

<400> SEQUENCE: 22

Phe Gln Leu Phe Ser Leu His Val Gln Pro His Gln Ser Ser Ala Pro
1               5                   10                  15

Ala Asp Tyr Tyr Glu Gln Ala Gln Gly Lys Thr Gly Glu Ala Leu Lys
            20                  25                  30

Gln Ala Leu His Asp Thr Ile Asp Asp His Arg Glu Leu Ser Tyr Ser
        35                  40                  45

Glu Val Trp Glu Ala Leu Lys Ala Thr Asp Glu Asp Pro Ala Asn Arg
    50                  55                  60

Asn Asn Val Ile Leu Ile Tyr Ser Arg Glu Ser Arg Ser Lys Gln Ala
65                  70                  75                  80

Asn Gly Gly Gln Thr Gly Asp Trp Asn Arg Glu His Val Trp Ala Lys
                85                  90                  95

Ser His Gly Asp Phe Gly Thr Ser Lys Gly Pro Gly Thr Asp Leu His
            100                 105                 110

His Leu Arg Pro Ser Asp Val Gln Val Asn Ala Ala Arg Gly Asn Leu
        115                 120                 125

Asp Phe Asp Glu Gly Gly Ser Pro Tyr Pro Gly Ser Pro Gly Asn Arg
    130                 135                 140

Tyr Asp Gly Asp Ser Trp Glu Pro Asp Lys Ser Ile Lys Gly Asp Val
145                 150                 155                 160

Ala Arg Met Ile Phe Tyr Met Ala Val Arg Tyr Glu Gly Asp Asp Gly
                165                 170                 175

Gln Pro Asp Leu Glu Met Asn Asp Thr Thr Asn Asn Gly Ser Lys Pro
            180                 185                 190

Tyr His Gly Lys Met Ser Val Leu Leu Lys Trp His His Glu Asp Pro
        195                 200                 205

Val Asp Ala Leu Glu Arg Lys Arg Asn Asp Ile Ile Tyr Gln Gln Tyr
    210                 215                 220

Gln His Asn Arg Asn Pro Phe Ile Asp His Pro Glu Trp Ala Glu Asp
225                 230                 235                 240

Ile Trp Gly Ser Gly Val Leu Asn
                245

<210> SEQ ID NO 23
<211> LENGTH: 822
<212> TYPE: DNA
<213> ORGANISM: Streptomyces thermocarboxydus
<220> FEATURE:
<221> NAME/KEY: CDS
<222> LOCATION: (1)..(819)
<220> FEATURE:
<221> NAME/KEY: sig_peptide
<222> LOCATION: (1)..(105)
<220> FEATURE:
<221> NAME/KEY: mat_peptide
<222> LOCATION: (106)..(819)

<400> SEQUENCE: 23 atg cct gtt gtg cgc ata cgc cgc cgg aag gcg gtg gcg ctg gcg agc      48
Met Pro Val Val Arg Ile Arg Arg Arg Lys Ala Val Ala Leu Ala Ser
-35                 -30                 -25                 -20 gcc gcc gtc ctc gcc gga ctc gcc gtc ccc gcc ctc acc ccc gcc acg      96
Ala Ala Val Leu Ala Gly Leu Ala Val Pro Ala Leu Thr Pro Ala Thr
            -15                 -10                 -5
```

```
gcc ggc gcc tcg gcg ccc gcc ccc gag acc cgg gcc gcc gcg gtg gcc      144
Ala Gly Ala Ser Ala Pro Ala Pro Glu Thr Arg Ala Ala Ala Val Ala
         -1  1           5              10 gac tac tac gag ggc gcc gag ggc aag acc ggc gag gcc ctc aag tcc      192
Asp Tyr Tyr Glu Gly Ala Glu Gly Lys Thr Gly Glu Ala Leu Lys Ser
         15              20              25 gcc ctc aac tcg atc atc agc gac cag acg aag ctg tcg tac tcg gcc      240
Ala Leu Asn Ser Ile Ile Ser Asp Gln Thr Lys Leu Ser Tyr Ser Ala
30              35              40              45 gtc tgg gac gcc ctc aag gag acc gac gag gac ccg tcg aac agc ggc      288
Val Trp Asp Ala Leu Lys Glu Thr Asp Glu Asp Pro Ser Asn Ser Gly
                50              55              60 aac gtg atc ctg ctg tac tcc ggc gtc tcc cgc agc aag tcg ctc aac      336
Asn Val Ile Leu Leu Tyr Ser Gly Val Ser Arg Ser Lys Ser Leu Asn
             65              70              75 ggc ggt gac gtg ggc gac tgg aac cgc gag cac gtc tgg gcc aag tcc      384
Gly Gly Asp Val Gly Asp Trp Asn Arg Glu His Val Trp Ala Lys Ser
         80              85              90 cac ggc gac ttc ggc acc tcc acc ggc ccc ggc acc gac atc cac cac      432
His Gly Asp Phe Gly Thr Ser Thr Gly Pro Gly Thr Asp Ile His His
95              100             105 ctg cgt ccg tcg gac gtc cag gtc aac agc gtc cgc ggc aac aag gac      480
Leu Arg Pro Ser Asp Val Gln Val Asn Ser Val Arg Gly Asn Lys Asp
110             115             120             125 ttc gac aac ggc ggc agc gcc gtc gcg aac ggg ggc agc ctc acc           528
Phe Asp Asn Gly Gly Ser Ala Val Ala Asn Gly Gly Ser Leu Thr
                130             135             140 gac tcc gac tcc ttc gag ccg cgc gac gcg gtc aag ggc gac gtg gcc      576
Asp Ser Asp Ser Phe Glu Pro Arg Asp Ala Val Lys Gly Asp Val Ala
            145             150             155 cgc atg atc ttc tac atg gcg gtc cgc tac gag ggc acc gac ggc tgg      624
Arg Met Ile Phe Tyr Met Ala Val Arg Tyr Glu Gly Thr Asp Gly Trp
        160             165             170 ccc gac ctg gag ccg aac aac agc gtg agc aac ggc tcc gcg ccg tac      672
Pro Asp Leu Glu Pro Asn Asn Ser Val Ser Asn Gly Ser Ala Pro Tyr
    175             180             185 atc ggc aag ctc tcg gta ctc aag gag tgg aac gaa cag gac ccg ccg      720
Ile Gly Lys Leu Ser Val Leu Lys Glu Trp Asn Glu Gln Asp Pro Pro
190             195             200             205 gac gcc ttc gag cag cac cgc aac gac gtg atc tac gag tcg tac cag      768
Asp Ala Phe Glu Gln His Arg Asn Asp Val Ile Tyr Glu Ser Tyr Gln
                210             215             220 cac aac cgg aac ccg ttc atc gac cac ccg gag tgg gtc gag tcg atc      816
His Asn Arg Asn Pro Phe Ile Asp His Pro Glu Trp Val Glu Ser Ile
            225             230             235 tgg tag                                                              822
Trp

<210> SEQ ID NO 24
<211> LENGTH: 273
<212> TYPE: PRT
<213> ORGANISM: Streptomyces thermocarboxydus

<400> SEQUENCE: 24

Met Pro Val Val Arg Ile Arg Arg Lys Ala Val Ala Leu Ala Ser
-35                 -30             -25             -20

Ala Ala Val Leu Ala Gly Leu Ala Val Pro Ala Leu Thr Pro Ala Thr
            -15             -10             -5

Ala Gly Ala Ser Ala Pro Ala Pro Glu Thr Arg Ala Ala Ala Val Ala
        -1  1           5               10
```

```
Asp Tyr Tyr Glu Gly Ala Glu Gly Lys Thr Gly Glu Ala Leu Lys Ser
         15                  20                  25

Ala Leu Asn Ser Ile Ile Ser Asp Gln Thr Lys Leu Ser Tyr Ser Ala
 30                  35                  40                  45

Val Trp Asp Ala Leu Lys Glu Thr Asp Glu Asp Pro Ser Asn Ser Gly
                 50                  55                  60

Asn Val Ile Leu Leu Tyr Ser Gly Val Ser Arg Ser Lys Ser Leu Asn
                 65                  70                  75

Gly Gly Asp Val Gly Asp Trp Asn Arg Glu His Val Trp Ala Lys Ser
             80                  85                  90

His Gly Asp Phe Gly Thr Ser Thr Gly Pro Gly Thr Asp Ile His His
         95                 100                 105

Leu Arg Pro Ser Asp Val Gln Val Asn Ser Val Arg Gly Asn Lys Asp
110                 115                 120                 125

Phe Asp Asn Gly Gly Ser Ala Val Ala Asn Gly Gly Ser Leu Thr
                130                 135                 140

Asp Ser Asp Ser Phe Glu Pro Arg Asp Ala Val Lys Gly Asp Val Ala
                145                 150                 155

Arg Met Ile Phe Tyr Met Ala Val Arg Tyr Glu Gly Thr Asp Gly Trp
             160                 165                 170

Pro Asp Leu Glu Pro Asn Asn Ser Val Ser Asn Gly Ser Ala Pro Tyr
        175                 180                 185

Ile Gly Lys Leu Ser Val Leu Lys Glu Trp Asn Glu Gln Asp Pro Pro
190                 195                 200                 205

Asp Ala Phe Glu Gln His Arg Asn Asp Val Ile Tyr Glu Ser Tyr Gln
                210                 215                 220

His Asn Arg Asn Pro Phe Ile Asp His Pro Glu Trp Val Glu Ser Ile
            225                 230                 235

Trp

<210> SEQ ID NO 25
<211> LENGTH: 238
<212> TYPE: PRT
<213> ORGANISM: Streptomyces thermocarboxydus

<400> SEQUENCE: 25

Ser Ala Pro Ala Pro Glu Thr Arg Ala Ala Val Ala Asp Tyr Tyr
 1               5                  10                  15

Glu Gly Ala Glu Gly Lys Thr Gly Glu Ala Leu Lys Ser Ala Leu Asn
                 20                  25                  30

Ser Ile Ile Ser Asp Gln Thr Lys Leu Ser Tyr Ser Ala Val Trp Asp
             35                  40                  45

Ala Leu Lys Glu Thr Asp Glu Asp Pro Ser Asn Ser Gly Asn Val Ile
 50                  55                  60

Leu Leu Tyr Ser Gly Val Ser Arg Ser Lys Ser Leu Asn Gly Gly Asp
 65                  70                  75                  80

Val Gly Asp Trp Asn Arg Glu His Val Trp Ala Lys Ser His Gly Asp
                 85                  90                  95

Phe Gly Thr Ser Thr Gly Pro Gly Thr Asp Ile His His Leu Arg Pro
            100                 105                 110

Ser Asp Val Gln Val Asn Ser Val Arg Gly Asn Lys Asp Phe Asp Asn
        115                 120                 125

Gly Gly Ser Ala Val Ala Asn Gly Gly Ser Leu Thr Asp Ser Asp
130                 135                 140
```

```
Ser Phe Glu Pro Arg Asp Ala Val Lys Gly Asp Val Ala Arg Met Ile
145                 150                 155                 160

Phe Tyr Met Ala Val Arg Tyr Glu Gly Thr Asp Gly Trp Pro Asp Leu
                165                 170                 175

Glu Pro Asn Asn Ser Val Ser Asn Gly Ser Ala Pro Tyr Ile Gly Lys
            180                 185                 190

Leu Ser Val Leu Lys Glu Trp Asn Glu Gln Asp Pro Pro Asp Ala Phe
            195                 200                 205

Glu Gln His Arg Asn Asp Val Ile Tyr Glu Ser Tyr Gln His Asn Arg
        210                 215                 220

Asn Pro Phe Ile Asp His Pro Glu Trp Val Glu Ser Ile Trp
225                 230                 235

<210> SEQ ID NO 26
<211> LENGTH: 822
<212> TYPE: DNA
<213> ORGANISM: Bacillus licheniformis
<220> FEATURE:
<221> NAME/KEY: CDS
<222> LOCATION: (1)..(819)
<220> FEATURE:
<221> NAME/KEY: sig_peptide
<222> LOCATION: (1)..(75)
<220> FEATURE:
<221> NAME/KEY: mat_peptide
<222> LOCATION: (76)..(819)

<400> SEQUENCE: 26 atg aat cga aaa tgt ctc ata ccg ttt att ttg atg ttg tcg gcg atg      48
Met Asn Arg Lys Cys Leu Ile Pro Phe Ile Leu Met Leu Ser Ala Met
-25                 -20                 -15                 -10 tgc gcg ccc acc caa aac gca gaa gcc ttc cag ttg ttt tcc tta cac      96
Cys Ala Pro Thr Gln Asn Ala Glu Ala Phe Gln Leu Phe Ser Leu His
                -5              -1  1               5 gtc cag ccc cat cag tcc tcg gct ccg gcg gat tac tac gaa cag gca     144
Val Gln Pro His Gln Ser Ser Ala Pro Ala Asp Tyr Tyr Glu Gln Ala
            10                  15                  20 caa ggc aaa aca ggc gaa gct tta aaa caa gcg ctt cac gac aca atc     192
Gln Gly Lys Thr Gly Glu Ala Leu Lys Gln Ala Leu His Asp Thr Ile
    25                  30                  35 gac gat cat aga gag ctt tct tac agt gag gta tgg gaa gcg ctg aaa     240
Asp Asp His Arg Glu Leu Ser Tyr Ser Glu Val Trp Glu Ala Leu Lys
40                  45                  50                  55 gca acg gac gaa gat ccg gcc aat cga aat cac gtg att ctc tta tat     288
Ala Thr Asp Glu Asp Pro Ala Asn Arg Asn His Val Ile Leu Leu Tyr
                60                  65                  70 tcc agg gag tcg cgc tct aaa cag gcg aac ggg ggg caa acc ggc gat     336
Ser Arg Glu Ser Arg Ser Lys Gln Ala Asn Gly Gly Gln Thr Gly Asp
            75                  80                  85 tgg aac cgc gag cac gta tgg gca aaa tcg cac ggc gat ttc gga aca     384
Trp Asn Arg Glu His Val Trp Ala Lys Ser His Gly Asp Phe Gly Thr
        90                  95                  100 agc aaa ggg ccc gga aca gat ttg cat cat ctc agg ccc agc gat gta     432
Ser Lys Gly Pro Gly Thr Asp Leu His His Leu Arg Pro Ser Asp Val
    105                 110                 115 caa gta aac gcc gcc cgc gga aac ctt gat ttc gac gaa ggc ggc agc     480
Gln Val Asn Ala Ala Arg Gly Asn Leu Asp Phe Asp Glu Gly Gly Ser
120                 125                 130                 135 ccc tat ccc ggt tcc ccc gga aac cgc tat gac ggc gat tcc tgg gaa     528
Pro Tyr Pro Gly Ser Pro Gly Asn Arg Tyr Asp Gly Asp Ser Trp Glu
                140                 145                 150
```

```
cct gac aaa agc att aaa ggc gat gtc gcc aga atg att ttc tat atg       576
Pro Asp Lys Ser Ile Lys Gly Asp Val Ala Arg Met Ile Phe Tyr Met
            155                 160                 165 gcg gtc cgc tat gaa gga gat gac ggt cat ccg gat ctt gaa atg aac       624
Ala Val Arg Tyr Glu Gly Asp Asp Gly His Pro Asp Leu Glu Met Asn
            170                 175                 180 gac aca acg aac aac gga tct aaa cca tac cac gga aaa atg tcg gtt       672
Asp Thr Thr Asn Asn Gly Ser Lys Pro Tyr His Gly Lys Met Ser Val
            185                 190                 195 tta ttg aaa tgg cac cat gaa gac cct gtc gat gcc ctc gaa aga aag       720
Leu Leu Lys Trp His His Glu Asp Pro Val Asp Ala Leu Glu Arg Lys
200                 205                 210                 215 cgg aac gac atc atc tat cag caa tac cag cat aac cgc aat cca ttc       768
Arg Asn Asp Ile Ile Tyr Gln Gln Tyr Gln His Asn Arg Asn Pro Phe
                220                 225                 230 att gat cac cct gaa tgg gcg gag gat att tgg gga tca gac gtt ttg       816
Ile Asp His Pro Glu Trp Ala Glu Asp Ile Trp Gly Ser Asp Val Leu
                235                 240                 245 aat tga                                                               822
Asn

<210> SEQ ID NO 27
<211> LENGTH: 273
<212> TYPE: PRT
<213> ORGANISM: Bacillus licheniformis

<400> SEQUENCE: 27

Met Asn Arg Lys Cys Leu Ile Pro Phe Ile Leu Met Leu Ser Ala Met
-25                 -20                 -15                 -10

Cys Ala Pro Thr Gln Asn Ala Glu Ala Phe Gln Leu Phe Ser Leu His
                -5                  -1  1               5

Val Gln Pro His Gln Ser Ser Ala Pro Ala Asp Tyr Tyr Glu Gln Ala
                10                  15                  20

Gln Gly Lys Thr Gly Glu Ala Leu Lys Gln Ala Leu His Asp Thr Ile
            25                  30                  35

Asp Asp His Arg Glu Leu Ser Tyr Ser Glu Val Trp Glu Ala Leu Lys
40                  45                  50                  55

Ala Thr Asp Glu Asp Pro Ala Asn Arg Asn His Val Ile Leu Leu Tyr
                60                  65                  70

Ser Arg Glu Ser Arg Ser Lys Gln Ala Asn Gly Gly Gln Thr Gly Asp
            75                  80                  85

Trp Asn Arg Glu His Val Trp Ala Lys Ser His Gly Asp Phe Gly Thr
            90                  95                  100

Ser Lys Gly Pro Gly Thr Asp Leu His His Leu Arg Pro Ser Asp Val
            105                 110                 115

Gln Val Asn Ala Ala Arg Gly Asn Leu Asp Phe Asp Glu Gly Gly Ser
120                 125                 130                 135

Pro Tyr Pro Gly Ser Pro Gly Asn Arg Tyr Asp Gly Asp Ser Trp Glu
                140                 145                 150

Pro Asp Lys Ser Ile Lys Gly Asp Val Ala Arg Met Ile Phe Tyr Met
            155                 160                 165

Ala Val Arg Tyr Glu Gly Asp Asp Gly His Pro Asp Leu Glu Met Asn
            170                 175                 180

Asp Thr Thr Asn Asn Gly Ser Lys Pro Tyr His Gly Lys Met Ser Val
            185                 190                 195

Leu Leu Lys Trp His His Glu Asp Pro Val Asp Ala Leu Glu Arg Lys
```

```
                200                 205                 210                 215
Arg Asn Asp Ile Ile Tyr Gln Gln Tyr Gln His Asn Arg Asn Pro Phe
                220                 225                 230
Ile Asp His Pro Glu Trp Ala Glu Asp Ile Trp Gly Ser Asp Val Leu
                235                 240                 245
Asn

<210> SEQ ID NO 28
<211> LENGTH: 248
<212> TYPE: PRT
<213> ORGANISM: Bacillus licheniformis

<400> SEQUENCE: 28

Phe Gln Leu Phe Ser Leu His Val Gln Pro His Gln Ser Ser Ala Pro
1               5                   10                  15
Ala Asp Tyr Tyr Glu Gln Ala Gln Gly Lys Thr Gly Glu Ala Leu Lys
                20                  25                  30
Gln Ala Leu His Asp Thr Ile Asp Asp His Arg Glu Leu Ser Tyr Ser
            35                  40                  45
Glu Val Trp Glu Ala Leu Lys Ala Thr Asp Glu Asp Pro Ala Asn Arg
50                  55                  60
Asn His Val Ile Leu Leu Tyr Ser Arg Glu Ser Arg Ser Lys Gln Ala
65                  70                  75                  80
Asn Gly Gly Gln Thr Gly Asp Trp Asn Arg Glu His Val Trp Ala Lys
                85                  90                  95
Ser His Gly Asp Phe Gly Thr Ser Lys Gly Pro Gly Thr Asp Leu His
            100                 105                 110
His Leu Arg Pro Ser Asp Val Gln Val Asn Ala Ala Arg Gly Asn Leu
        115                 120                 125
Asp Phe Asp Glu Gly Gly Ser Pro Tyr Pro Gly Ser Pro Gly Asn Arg
130                 135                 140
Tyr Asp Gly Asp Ser Trp Glu Pro Asp Lys Ser Ile Lys Gly Asp Val
145                 150                 155                 160
Ala Arg Met Ile Phe Tyr Met Ala Val Arg Tyr Glu Gly Asp Asp Gly
                165                 170                 175
His Pro Asp Leu Glu Met Asn Asp Thr Thr Asn Asn Gly Ser Lys Pro
            180                 185                 190
Tyr His Gly Lys Met Ser Val Leu Leu Lys Trp His His Glu Asp Pro
        195                 200                 205
Val Asp Ala Leu Glu Arg Lys Arg Asn Asp Ile Ile Tyr Gln Gln Tyr
        210                 215                 220
Gln His Asn Arg Asn Pro Phe Ile Asp His Pro Glu Trp Ala Glu Asp
225                 230                 235                 240
Ile Trp Gly Ser Asp Val Leu Asn
                245

<210> SEQ ID NO 29
<211> LENGTH: 810
<212> TYPE: DNA
<213> ORGANISM: Saccharopolyspora gregorii
<220> FEATURE:
<221> NAME/KEY: CDS
<222> LOCATION: (1)..(807)
<220> FEATURE:
<221> NAME/KEY: sig_peptide
<222> LOCATION: (1)..(81)
<220> FEATURE:
<221> NAME/KEY: mat_peptide
```

<222> LOCATION: (82)..(807)

<400> SEQUENCE: 29

```
atg ctg aag acc cgc tgg aca cgc ttc gcg ctg gca ggt gtg ctg ccg        48
Met Leu Lys Thr Arg Trp Thr Arg Phe Ala Leu Ala Gly Val Leu Pro
    -25                 -20                 -15 ctg gcc gtg gcg ctg ccg ctg ccc gct tcc gcc gcg ccc gcc gac ctg        96
Leu Ala Val Ala Leu Pro Leu Pro Ala Ser Ala Ala Pro Ala Asp Leu
-10                  -5                  -1   1                5 ggc ggc acc gac cgc ccg gtg gcg gcg gac gac tcc tac tac gaa ccg       144
Gly Gly Thr Asp Arg Pro Val Ala Ala Asp Asp Ser Tyr Tyr Glu Pro
                10                  15                  20 gcg ctg ggc aag acc ggc ccg gag ctg aag gcc gcc ctc aac gac atc       192
Ala Leu Gly Lys Thr Gly Pro Glu Leu Lys Ala Ala Leu Asn Asp Ile
            25                  30                  35 atc agc agc gcc gac cag ctc acc tac gac gag gtg tgg gac gcg ctg       240
Ile Ser Ser Ala Asp Gln Leu Thr Tyr Asp Glu Val Trp Asp Ala Leu
        40                  45                  50 aag gtc acc gac cag gac ccg gcg aac ccg gac aac gtg atc ctg ctg       288
Lys Val Thr Asp Gln Asp Pro Ala Asn Pro Asp Asn Val Ile Leu Leu
    55                  60                  65 tac tcg ggc cgc tcg cag ggc aag gac acc aac ggc ggc ggc gcc gac       336
Tyr Ser Gly Arg Ser Gln Gly Lys Asp Thr Asn Gly Gly Gly Ala Asp
70                  75                  80                  85 cag tgg aac cgg gag cac acc tgg gcg aag tcg cac ggc gac ttc ggc       384
Gln Trp Asn Arg Glu His Thr Trp Ala Lys Ser His Gly Asp Phe Gly
                90                  95                  100 acc tcg ccc ggg ccg ggc acc gac gtg cac cac ctg cgc ccg acc gac       432
Thr Ser Pro Gly Pro Gly Thr Asp Val His His Leu Arg Pro Thr Asp
            105                 110                 115 gtc tcg gtc aac tcg gcg cgc ggc aac aag gac ttc gac atg ggc ggc       480
Val Ser Val Asn Ser Ala Arg Gly Asn Lys Asp Phe Asp Met Gly Gly
        120                 125                 130 agc ccg gtc gac gag gcc gag ggc aac ttc acc gac gac gac tcc ttc       528
Ser Pro Val Asp Glu Ala Glu Gly Asn Phe Thr Asp Asp Asp Ser Phe
    135                 140                 145 gag ccc cgc gac gag gtc aag ggc gac gtc gcc cgc atg atc atg tac       576
Glu Pro Arg Asp Glu Val Lys Gly Asp Val Ala Arg Met Ile Met Tyr
150                 155                 160                 165 atg gcg gtg cgc tac gaa ggc gac gac ggc gcc ccc gac ctg gag ctc       624
Met Ala Val Arg Tyr Glu Gly Asp Asp Gly Ala Pro Asp Leu Glu Leu
                170                 175                 180 aac gac cag gtg gac aac ggc agc gcg ccc gcg atg ggc cgc cag tcg       672
Asn Asp Gln Val Asp Asn Gly Ser Ala Pro Ala Met Gly Arg Gln Ser
            185                 190                 195 gtg ctg ctg gag tgg aac gcc cag gac ccg ccg gac gac ttc gag aag       720
Val Leu Leu Glu Trp Asn Ala Gln Asp Pro Pro Asp Asp Phe Glu Lys
        200                 205                 210 aac cgc aac cag gtc atc ttc gac cag ttc cag cac aac cgg aac ccg       768
Asn Arg Asn Gln Val Ile Phe Asp Gln Phe Gln His Asn Arg Asn Pro
    215                 220                 225 ttc atc gac cac ccg gag tgg gcg gcc gac atc tgg ggc tga              810
Phe Ile Asp His Pro Glu Trp Ala Ala Asp Ile Trp Gly
230                 235                 240
```

<210> SEQ ID NO 30
<211> LENGTH: 269
<212> TYPE: PRT
<213> ORGANISM: Saccharopolyspora gregorii

<400> SEQUENCE: 30

```
Met Leu Lys Thr Arg Trp Thr Arg Phe Ala Leu Ala Gly Val Leu Pro
        -25                 -20                 -15

Leu Ala Val Ala Leu Pro Leu Pro Ala Ser Ala Ala Pro Ala Asp Leu
    -10                  -5                  -1   1               5

Gly Gly Thr Asp Arg Pro Val Ala Ala Asp Asp Ser Tyr Tyr Glu Pro
                10                  15                  20

Ala Leu Gly Lys Thr Gly Pro Glu Leu Lys Ala Ala Leu Asn Asp Ile
            25                  30                  35

Ile Ser Ser Ala Asp Gln Leu Thr Tyr Asp Glu Val Trp Asp Ala Leu
        40                  45                  50

Lys Val Thr Asp Gln Asp Pro Ala Asn Pro Asp Asn Val Ile Leu Leu
    55                  60                  65

Tyr Ser Gly Arg Ser Gln Gly Lys Asp Thr Asn Gly Gly Gly Ala Asp
70                  75                  80                  85

Gln Trp Asn Arg Glu His Thr Trp Ala Lys Ser His Gly Asp Phe Gly
                90                  95                  100

Thr Ser Pro Gly Pro Gly Thr Asp Val His His Leu Arg Pro Thr Asp
            105                 110                 115

Val Ser Val Asn Ser Ala Arg Gly Asn Lys Asp Phe Asp Met Gly Gly
        120                 125                 130

Ser Pro Val Asp Glu Ala Glu Gly Asn Phe Thr Asp Asp Asp Ser Phe
    135                 140                 145

Glu Pro Arg Asp Glu Val Lys Gly Asp Val Ala Arg Met Ile Met Tyr
150                 155                 160                 165

Met Ala Val Arg Tyr Glu Gly Asp Asp Gly Ala Pro Asp Leu Glu Leu
                170                 175                 180

Asn Asp Gln Val Asp Asn Gly Ser Ala Pro Ala Met Gly Arg Gln Ser
            185                 190                 195

Val Leu Leu Glu Trp Asn Ala Gln Asp Pro Pro Asp Asp Phe Glu Lys
        200                 205                 210

Asn Arg Asn Gln Val Ile Phe Asp Gln Phe Gln His Asn Arg Asn Pro
    215                 220                 225

Phe Ile Asp His Pro Glu Trp Ala Ala Asp Ile Trp Gly
230                 235                 240

<210> SEQ ID NO 31
<211> LENGTH: 242
<212> TYPE: PRT
<213> ORGANISM: Saccharopolyspora gregorii

<400> SEQUENCE: 31

Ala Pro Ala Asp Leu Gly Gly Thr Asp Arg Pro Val Ala Ala Asp Asp
1               5                   10                  15

Ser Tyr Tyr Glu Pro Ala Leu Gly Lys Thr Gly Pro Glu Leu Lys Ala
                20                  25                  30

Ala Leu Asn Asp Ile Ile Ser Ser Ala Asp Gln Leu Thr Tyr Asp Glu
            35                  40                  45

Val Trp Asp Ala Leu Lys Val Thr Asp Gln Asp Pro Ala Asn Pro Asp
50                  55                  60

Asn Val Ile Leu Leu Tyr Ser Gly Arg Ser Gln Gly Lys Asp Thr Asn
65                  70                  75                  80

Gly Gly Gly Ala Asp Gln Trp Asn Arg Glu His Thr Trp Ala Lys Ser
                85                  90                  95

His Gly Asp Phe Gly Thr Ser Pro Gly Pro Gly Thr Asp Val His His
```

```
                100             105             110
Leu Arg Pro Thr Asp Val Ser Val Asn Ser Ala Arg Gly Asn Lys Asp
            115                 120                 125

Phe Asp Met Gly Gly Ser Pro Val Asp Glu Ala Glu Gly Asn Phe Thr
        130                 135                 140

Asp Asp Asp Ser Phe Glu Pro Arg Asp Glu Val Lys Gly Asp Val Ala
145                 150                 155                 160

Arg Met Ile Met Tyr Met Ala Val Arg Tyr Glu Gly Asp Asp Gly Ala
                165                 170                 175

Pro Asp Leu Glu Leu Asn Asp Gln Val Asp Asn Gly Ser Ala Pro Ala
            180                 185                 190

Met Gly Arg Gln Ser Val Leu Leu Glu Trp Asn Ala Gln Asp Pro Pro
        195                 200                 205

Asp Asp Phe Glu Lys Asn Arg Asn Gln Val Ile Phe Asp Gln Phe Gln
                210                 215                 220

His Asn Arg Asn Pro Phe Ile Asp His Pro Glu Trp Ala Ala Asp Ile
225                 230                 235                 240

Trp Gly
```

```
<210> SEQ ID NO 32
<211> LENGTH: 4
<212> TYPE: PRT
<213> ORGANISM: Artificial Sequence
<220> FEATURE:
<223> OTHER INFORMATION: Bacterial endonuclease 1 ribonuclease motif #1

<400> SEQUENCE: 32

Asn Arg Glu His
1

<210> SEQ ID NO 33
<211> LENGTH: 4
<212> TYPE: PRT
<213> ORGANISM: Artificial Sequence
<220> FEATURE:
<223> OTHER INFORMATION: Bacterial endonuclease 1 ribonuclease motif #2
<220> FEATURE:
<221> NAME/KEY: MISC_FEATURE
<222> LOCATION: (2)..(2)
<223> OTHER INFORMATION: Xaa = A(Ala) or E(Glu) or Q(Gln)

<400> SEQUENCE: 33

Asp Xaa Asp Pro
1

<210> SEQ ID NO 34
<211> LENGTH: 5
<212> TYPE: PRT
<213> ORGANISM: Artificial Sequence
<220> FEATURE:
<223> OTHER INFORMATION: Bacterial endonuclease 1 ribonuclease motif #3

<400> SEQUENCE: 34

Thr Asp Glu Asp Pro
1               5

<210> SEQ ID NO 35
<211> LENGTH: 7
<212> TYPE: PRT
<213> ORGANISM: Artificial Sequence
<220> FEATURE:
<223> OTHER INFORMATION: Bacterial endonuclease 1 ribonuclease motif #4
```

```
<400> SEQUENCE: 35

Asn Arg Glu His Val Trp Ala
1               5

<210> SEQ ID NO 36
<211> LENGTH: 27
<212> TYPE: PRT
<213> ORGANISM: Bacillus clausii

<400> SEQUENCE: 36

Met Lys Lys Pro Leu Gly Lys Ile Val Ala Ser Thr Ala Leu Leu Ile
1               5                   10                  15

Ser Val Ala Phe Ser Ser Ser Ile Ala Ser Ala
            20                  25
```